(12) United States Patent
Leo

(10) Patent No.: US 10,517,320 B2
(45) Date of Patent: Dec. 31, 2019

(54) METHOD TO PRODUCE CONCENTRATED VOLATILES FROM CANNABIS

(71) Applicant: Daniel Michael Leo, Baltimore, MD (US)

(72) Inventor: Daniel Michael Leo, Baltimore, MD (US)

(73) Assignee: INSECTERGY, LLC, Baltimore, MD (US)

(*) Notice: Subject to any disclaimer, the term of this patent is extended or adjusted under 35 U.S.C. 154(b) by 0 days.

(21) Appl. No.: 15/904,044

(22) Filed: Feb. 23, 2018

(65) Prior Publication Data

US 2018/0343901 A1 Dec. 6, 2018

Related U.S. Application Data

(63) Continuation of application No. 15/784,112, filed on Oct. 14, 2017, which is a continuation-in-part of application No. 15/609,472, filed on May 31, 2017.

(51) Int. Cl.

| | |
|---|---|
| *A23L 5/20* | (2016.01) |
| *A23B 7/153* | (2006.01) |
| *A01G 9/02* | (2018.01) |
| *A01H 6/28* | (2018.01) |
| *A23L 7/10* | (2016.01) |
| *A61K 36/185* | (2006.01) |
| *A01H 5/12* | (2018.01) |
| *A01G 7/04* | (2006.01) |
| *A01G 7/02* | (2006.01) |
| *A01G 24/48* | (2018.01) |
| *A01G 24/18* | (2018.01) |
| *A01G 24/23* | (2018.01) |
| *A01G 24/00* | (2018.01) |

(52) U.S. Cl.
CPC .................. *A23L 5/23* (2016.08); *A01G 9/02* (2013.01); *A01H 5/12* (2013.01); *A01H 6/28* (2018.05); *A23B 7/153* (2013.01); *A23L 7/10* (2016.08); *A61K 36/185* (2013.01); *A01G 7/02* (2013.01); *A01G 7/045* (2013.01); *A01G 24/00* (2018.02); *A01G 24/18* (2018.02); *A01G 24/23* (2018.02); *A01G 24/48* (2018.02); *A23V 2002/00* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 7,344,736 B2 * | 3/2008 | Whittle ................ | A61K 31/352 424/725 |
| 9,649,349 B1 * | 5/2017 | Tucker .................... | B01D 3/02 |
| 2010/0060416 A1 * | 3/2010 | Watanabe .......... | G07C 9/00158 340/5.82 |
| 2012/0060416 A1 * | 3/2012 | Brusatore .............. | A01G 31/06 47/62 A |

FOREIGN PATENT DOCUMENTS

WO WO-2017184642 A1 * 10/2017 ........... A61K 36/185

OTHER PUBLICATIONS

Thrive Alive B1 Green product information retrieved from https://www.planetnatural.com/product/thrive-alive-b-1-green/. (Year: 2019).*
Bloom 2-6-6 product information retrieved from https://www.planetnatural.com/product/pura-vida-organics-bloom/. (Year: 2019).*
Salazar, N., BigBudsMag.com, "Marijuana Carbohydrates Boost Growth, Root Function, Bud Size, & THC." (Year: 2015).*

\* cited by examiner

*Primary Examiner* — Michael Barker

(57) ABSTRACT

Variable-scale, modular, easily manufacturable, energy efficient, reliable, and computer-operated farming superstructure systems (FSS) may be used to produce cannabis for human consumption with minimal water and environmental impact. Methods to method to separate volatiles from cannabis are described. Methods to asexually clone a plurality of cannabis plants are also provided.

32 Claims, 27 Drawing Sheets

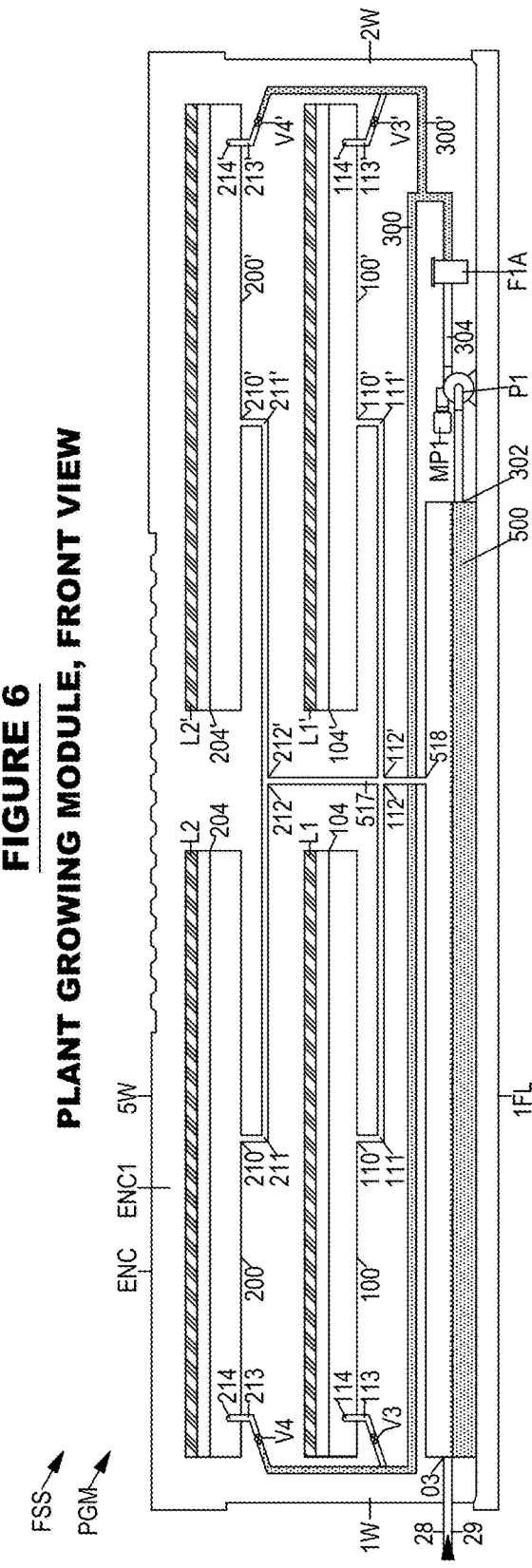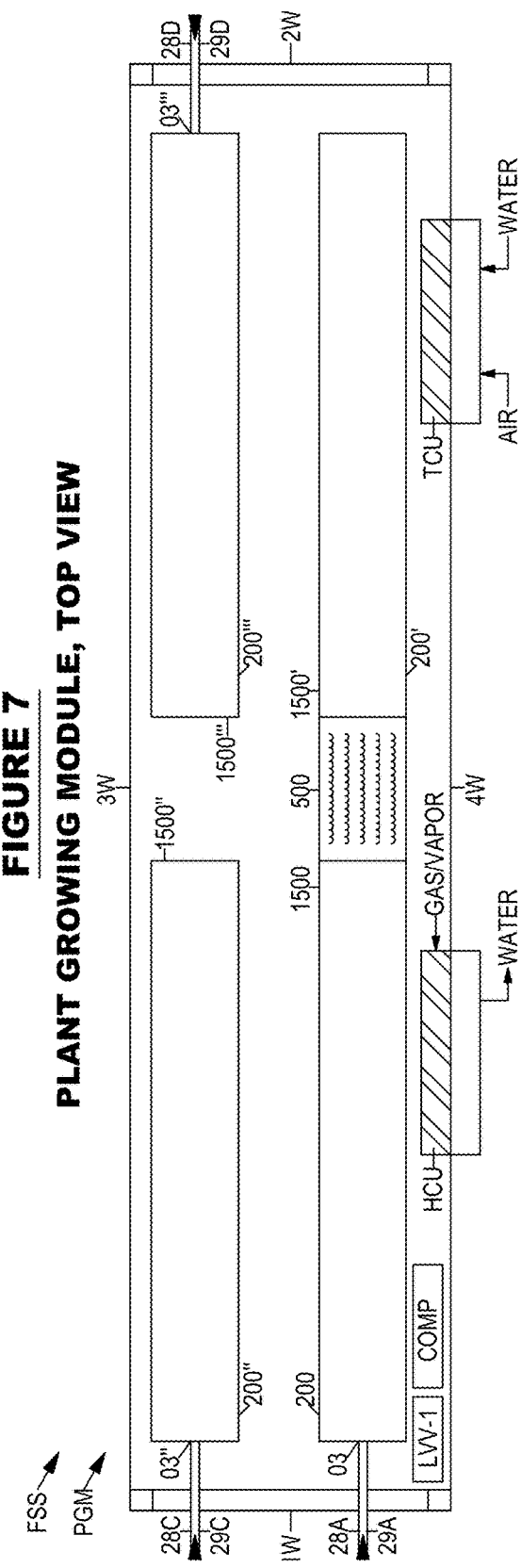

PLANT GROWING MODULE, SIDE VIEW

LIQUID DISTRIBUTION MODULE, FRONT VIEW

SOLUTION MIXING MODULE, TOP VIEW

LIQUID DISTRIBUTION MODULE, SIDE VIEW

CANNABIS TRIMMING

CANNABIS GRINDING

CANNABIS HEATING

VOLATILES SEPARATION

VOLATILES SEPARATION

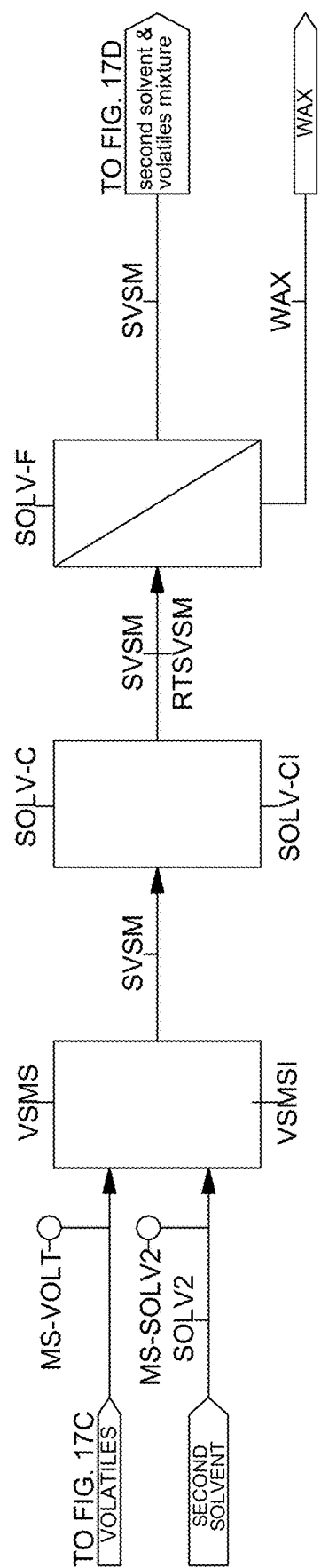

SOLVENT SEPARATION SYSTEM

MULTIFUNCTIONAL COMPOSITION MIXING MODULE

CANNABIS CLONING

METHOD TO PRODUCE CONCENTRATED VOLATILES FROM CANNABIS

RELATED APPLICATIONS

This application is a Continuation of my co-pending patent application Ser. No. 15/784,112, filed on Oct. 14, 2017, which is a Continuation-In-Part of my co-pending patent application Ser. No. 15/609,472, filed on May 31, 2017. The contents of the aforementioned applications are incorporated by reference in their entirety.

TECHNICAL FIELD

The present disclosure relates to improvements to cannabis farming systems and methods. The present disclosure also relates to a new and distinct plant named Grass Weedly Junior characterized by a hybrid between *Cannabis sativa* L. ssp. *sativa* and *Cannabis sativa* L. ssp. *indica* (Lam.) and relevant cannabis farming systems and methods.

BACKGROUND

Efficient, reliable, and consistent, computer-operated cannabis farming systems and methods are needed to meet the cannabis production demands of society. In recent years, there has been an increasing demand for cannabis for medicinal and recreational use. Large-scale cannabis farming systems must be designed carefully to minimize environmental impact, reduce manual labor and human interaction, and automate the system as much as possible while maximizing plant growth. These systems must be precisely sized and situated to be able to provide systematically timed and controlled computer-operated methods to maintain a sufficient amount of water and nutrients for the cannabis at a precise temperature, humidity level, pH, oxygen and/or carbon dioxide level, air velocity, and light wavelength and schedule. A need exists for cannabis farming facilities that maximize plant production on a small physical outlay while providing adequate space for high-density plant growth all at an economically attractive cost.

The ability to grow cannabis with minimal human interaction has been long regarded as desirable and needed to facilitate widespread use for human consumption and for the production of food. It is of importance that large-scale, standardized, modular, easily manufacturable, energy efficient, reliable, computer-operated cannabis farming systems and facilities are extensively deployed to produce cannabis for medicinal and recreation use with minimal water and environmental impact.

There is a need for cannabis farming facilities to employ systems and methods that can clean and decontaminate water from harsh and unpredictable sources and provide a clean water source suitable to feed and grow cannabis. There is a need to re-use old containerized shipping containers to promote the implementation of widespread commercial production of cannabis to promote regional, rural, and urban job opportunities that maximize the quality of living where the cannabis is farmed.

There is a need for a superior blend of *Cannabis sativa* L. ssp. *sativa* and *Cannabis sativa* L. ssp. *indica* (Lam.) that provides improved medicinal benefits, and has a high yield to meet industrial, commercial, recreational, and medicinal demand at a low price and minimal economic and environmental impact. There is a need for a new variety of plant that has a repeatable, predictable, and unique chemical composition that is based upon standardized engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, while having preferred specific *Cannabis sativa* L. ssp. *sativa* and *Cannabis sativa* L. ssp. *indica* (Lam.) weight percentages.

SUMMARY

This Summary is provided merely to introduce certain concepts and not to identify any key or essential features of the claimed subject matter.

Paragraph A. A method to separate volatiles from cannabis, the method includes:
 (a) providing a source of water;
 (b) removing positively charged ions and negatively charged ions and optionally undesirable compounds from the water of step (a);
 (c) mixing the water after step (b) with macro-nutrients, micro-nutrients, or a pH adjustment solution to form a liquid mixture;
 (d) pressurizing the liquid mixture after step (c) to form a pressurized liquid mixture;
 (e) transferring the pressurized liquid mixture of step (d) to the plurality of growing assemblies;
 (f) illuminating the plurality of growing assemblies with a plurality of lights;
 (g) growing cannabis within the plurality of growing assemblies after step (f);
 (h) harvesting the cannabis after growing cannabis in step (g);
 (i) grinding the cannabis after step (h); and
 (j) extracting volatiles from cannabis after step (i) with a first solvent to form a first solvent and volatiles mixture;
wherein:
 the positively charged ions are comprised of one or more from the group consisting of calcium, magnesium, sodium, and iron;
 the negatively charged ions are comprised of one or more from the group consisting of iodine, chloride, and sulfate;
 the undesirable compounds are comprised of one or more from the group consisting of dissolved organic chemicals, viruses, bacteria, and particulates;
 the macro-nutrients are comprised of one or more from the group consisting of nitrogen, phosphorus, potassium, calcium, magnesium, and sulfur;
 the micro-nutrients are comprised of one or more from the group consisting of iron, manganese, boron, molybdenum, copper, zinc, sodium, chlorine, and silicon;
 the pH adjustment solution is comprised of one or more from the group consisting acid, nitric acid, phosphoric acid, potassium hydroxide, sulfuric acid, organic acids, citric acid, and acetic acid;
 the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, and vapor.

Paragraph B. The method according to Paragraph A, further comprising:
 (k) separating at least a portion of the volatiles from the first solvent and volatiles mixture;

(l) mixing the volatiles with a second solvent after step (k) to form a second volatiles and solvent mixture; and (m) evaporating at least a portion of the second solvent from the second volatiles and solvent mixture to create concentrated volatiles that have reduced amount of second solvent relative to the second volatiles and solvent mixture;

wherein:

the second solvent includes one or more from the group consisting of a liquid, acetone, alcohol, oil, and ethanol.

Paragraph C. The method according to Paragraph B, further comprising:

cooling the second volatiles and solvent mixture after step (l); and filtering the second volatiles and solvent mixture before step (m).

Paragraph D. The method according to Paragraph B, further comprising:

in step (j), separating volatiles from cannabis using a method that includes:

(j1) separating terpenes from the cannabis at a first temperature and a first pressure; and (j2) separating oil and wax from the cannabis at a second temperature and a second pressure;

wherein:

the second temperature is greater than the first temperature;

the second pressure is greater than the first pressure;

the terpenes include one or more from the group consisting of limonene, humulene, pinene, linalool, caryophyllene, mycrene, eucalyptol, nerolidol, bisablol, and phytol;

the volatiles include oil, wax, and terpenes.

Paragraph E. The method according to Paragraph A, wherein the cannabis is comprised of a new and distinct hybrid plant named Grass Weedly Junior characterized by a hybrid between *Cannabis sativa* L. ssp. *sativa* and *Cannabis sativa* L. ssp. *indica* (Lam.), within the leaves, seeds, stems, roots, or any reproductive structures, Grass Weedly Junior has:

(a) a cannabidiol content ranging from 0.00001 weight percent to 25 weight percent;

(b) a tetrahydrocannabinol content ranging from 4 weigh percent to 66 weigh percent;

(c) an energy content ranging from between 2,500 British Thermal Units per pound to 65,000 British Thermal Units per pound;

(d) a carbon content ranging from between 15 weight percent to 66 weight percent;

(e) an oxygen content ranging from between 10 weight percent to 60 weight percent;

(f) a hydrogen content ranging from between 2 weight percent to 25 weight percent;

(g) an ash content ranging from between 2 weight percent to 35 weight percent;

(h) a volatiles content ranging from between 20 weight percent to 92 weight percent;

(i) a nitrogen content ranging from between 0.5 weight percent to 20 weight percent;

(j) a sulfur content ranging from between 0.01 weight percent to 10 weight percent;

(k) a chlorine content ranging from 0.01 weight percent to 15 weight percent;

(l) a sodium content ranging from 0.01 weight percent to 20 weight percent;

(m) a potassium content ranging from 0.01 weight percent to 15 weight percent;

(n) an iron content ranging from 0.005 weight percent to 15 weight percent;

(o) a magnesium content ranging from 0.01 weight percent to 11 weight percent;

(p) a phosphorous content ranging from 0.02 weight percent to 14 weight percent;

(q) a calcium content ranging from 0.02 weight percent to 12 weight percent;

(r) a zinc content ranging from 0.01 weight percent to 7 weight percent;

(s) a cellulose content ranging from 15 weight percent to 77 weight percent;

(t) a lignin content ranging from 2 weight percent to 40 weight percent;

(u) a hemicellulose content ranging from 2 weight percent to 36 weight percent;

(v) a fat content ranging from 4 weight percent to 45 weight percent;

(w) a fiber content ranging from 5 weight percent to 75 weight percent; and (x) a protein content ranging from 5 weight percent to 35 weight percent, as illustrated and described herein;

wherein:

the *Cannabis sativa* L. ssp. *sativa* content ranges from 15 weight percent to 85 weight percent;

the *Cannabis sativa* L. ssp. *indica* (Lam.) content ranges from 15 weight percent to 85 weight percent.

Paragraph F. The method according to Paragraph A, further comprising:

adjusting the carbon dioxide concentration above the plurality of growing assemblies to a range between 400 parts per million and 30,000 parts per million.

Paragraph G. The method according to Paragraph A, wherein the plurality of lights includes blue LEDs and red LEDs, further comprising;

(a) illuminating the plurality of growing assemblies at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again;

wherein:

the blue LEDs operate at a wavelength that ranges from 490 nanometers to 455 nanometers;

the red LEDs operate at a wavelength that ranges from 620 nanometers to 780 nanometers.

Paragraph H. The method according to Paragraph A, further comprising:

after step (j), creating a multifunctional composition by mixing at least a portion of the first solvent and volatiles mixture with two or more from the group consisting of a fiber-starch material, a binding agent, a density improving textural supplement, a moisture improving textural supplement, and insects;

wherein:

the fiber-starch materials are comprised of one or more from the group consisting of cereal-grain-based materials, grass-based materials, nut-based materials, powdered fruit materials, root-based materials, tuber-based materials, and vegetable-based materials;

the binding agents are comprised of one or more from the group consisting of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, psyllium husks, sago, sugars, syrups, tapioca, vegetable gums, and xanthan gum;

the density improving textural supplements are comprised of one or more from the group consisting of extracted arrowroot starch, extracted corn starch, extracted lentil starch, extracted potato starch, and extracted tapioca starch;

the moisture improving textural supplements are comprised of one or more from the group consisting of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts;

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil; one or more from the group consisting of:

mixing a fiber-starch material at a fiber-starch mass ratio that ranges from between 100 pounds of fiber-starch material per ton of multifunctional composition to 1800 pounds of fiber-starch material per ton of multifunctional composition, mixing a binding agent at a binding agent mass ratio that ranges from between 10 pounds of binding agent per ton of multifunctional composition to 750 pounds of binding agent per ton of multifunctional composition, mixing a density improving textural supplement at a density improving textural supplement mass ratio that ranges from between 10 pounds of density improving textural supplement per ton of multifunctional composition to 1000 pounds of density improving textural supplement per ton of multifunctional composition, mixing a moisture improving textural supplement at a moisture improving textural supplement mass ratio that ranges from between 10 pounds of moisture improving textural supplement per ton of multifunctional composition to 1000 pounds of moisture improving textural supplement per ton of multifunctional composition, and mixing insects at an insect mass ratio that ranges from between 25 pounds of insects per ton of multifunctional composition to 1500 pounds of insects per ton of multifunctional composition.

Paragraph I. A method to asexually clone a plurality of cannabis plants according to Paragraph A, the method includes:
  (a) providing:
    (a0) a plurality of cannabis plants in step (g);
    (a1) a cutting tool;
    (a2) a liquid, powder, or gel rooting solution, the rooting solution includes one or more from the group consisting of water, carbohydrates, enzymes, vitamins, hormones, and microorganisms;
    (a3) a growing medium, the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene;
    (a4) a plurality of containers configured to accept the rooting solution and the growing medium, the plurality of containers are configured to be positioned within a cloning enclosure;
    (a5) the cloning enclosure has an interior, the cloning enclosure is configured to contain water vapor within the interior to provide a humid environment for cannabis plants within the interior;
  (b) introducing the rooting solution and the growing medium to the plurality of containers;
  (c) using the cutting tool to sever the tips from a plurality of cannabis plants to form a plurality of severed plants;
  (d) inserting the plurality of severed plants of step (c) into the plurality of containers;
  (e) placing the plurality of containers within the interior of the cloning enclosure;
  (f) illuminating the plants after step (e);
  (g) growing the plants for 4 to 20 days or until roots are formed;
wherein:

the carbohydrates are comprised of one or more from the group consisting of sugar, sucrose, molasses, and plant syrups;

the enzymes are comprised of one or more from the group consisting of amino acids, orotidine 5'-phosphate decarboxylase, OMP decarboxylase, glucanase, beta-glucanase, cellulase, xylanase, Hygrozyme®, Cannazyme®, Microzyme®, and Sensizyme®;

the vitamins are comprised of one or more from the group consisting of vitamin B, vitamin C, vitamin D, and vitamin E;

the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotrop archaea, azotobacter vinelandii, clostridium pasteurianu, fungi, arbuscular mycorrhizal fungi, mycorrhiza, glomus aggrefatum, glomus etunicatum, glomus intraradices, rhizophagus irregularis, and glomus mosseae.

Paragraph J. A method to separate volatiles from cannabis, the method includes:
  (a) providing a source of cannabis;
  (b) grinding the cannabis after step (a);
  (c) extracting volatiles from cannabis after step (b) with a first solvent to form a first solvent and volatiles mixture;
  (d) separating at least a portion of the volatiles from the first solvent and volatiles mixture;
  (e) mixing the volatiles with a second solvent after step (d) to form a second volatiles and solvent mixture;
  (f) cooling the second volatiles and solvent mixture after step (e);
  (g) filtering the second volatiles and solvent mixture; and
  (h) evaporating the second solvent from the second volatiles and solvent mixture;
wherein:

the first solvent includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, and vapor;

the second solvent includes one or more from the group consisting of a liquid, acetone, alcohol, oil, and ethanol;

the terpenes include one or more from the group consisting of limonene, humulene, pinene, linalool, caryophyllene, mycrene, eucalyptol, nerolidol, bisablol, and phytol.

Paragraph K. A method to separate volatiles from cannabis, the method includes:
(a) providing a source of water;
(b) removing positively charged ions, negatively charged ions, or undesirable compounds from the water of step (a);
(c) mixing the water after step (b) with macro-nutrients, micro-nutrients, or a pH adjustment solution to form a liquid mixture;
(d) pressurizing the liquid mixture after step (c) to form a pressurized liquid mixture;
(e) transferring the pressurized liquid mixture of step (d) to the plurality of growing assemblies;
(f) illuminating the plurality of growing assemblies with the plurality of lights;
(g) growing cannabis within the plurality of growing assemblies after step (f);
(h) harvesting the cannabis after growing cannabis in step (g);
(i) grinding the cannabis after step (h);
(j) extracting volatiles from cannabis after step (i) with a first solvent to form a first solvent and volatiles mixture;
(k) separating at least a portion of the volatiles from the first solvent and volatiles mixture;
(l) mixing the volatiles with a second solvent after step (k) to form a second volatiles and solvent mixture;
(m) evaporating at least a portion of the second solvent from the second volatiles and solvent mixture to create concentrated volatiles that have reduced amount of second solvent relative to the second volatiles and solvent mixture;
wherein:
the positively charged ions are comprised of one or more from the group consisting of calcium, magnesium, sodium, and iron;
the negatively charged ions are comprised of one or more from the group consisting of iodine, chloride, and sulfate;
the undesirable compounds are comprised of one or more from the group consisting of dissolved organic chemicals, viruses, bacteria, and particulates;
the macro-nutrients are comprised of one or more from the group consisting of nitrogen, phosphorus, potassium, calcium, magnesium, and sulfur;
the micro-nutrients are comprised of one or more from the group consisting of iron, manganese, boron, molybdenum, copper, zinc, sodium, chlorine, and silicon;
the pH adjustment solution is comprised of one or more from the group consisting acid, nitric acid, phosphoric acid, potassium hydroxide, sulfuric acid, organic acids, citric acid, and acetic acid;
the first solvent includes one or more from the group consisting of acetone, alcohol, butane, carbon dioxide, ethanol, gas, gaseous carbon dioxide, hexane, isobutane, isopropanol, liquid carbon dioxide, liquid, naphtha, pentane, propane, R134 refrigerant gas, subcritical carbon dioxide, supercritical carbon dioxide, and vapor;
the second solvent includes one or more from the group consisting of a liquid, acetone, alcohol, oil, and ethanol.

Paragraph L. The method according to Paragraph K, further comprising:

cooling the second volatiles and solvent mixture after step (l); and
filtering the second volatiles and solvent mixture before step (m).

Paragraph M. The method according to Paragraph K, further comprising:
in step (j), separating volatiles from cannabis using a method that includes:
(j1) separating terpenes from the cannabis at a first temperature and a first pressure; and
(j2) separating oil and wax from the cannabis at a second temperature and a second pressure;
wherein:
the second temperature is greater than the first temperature;
the second pressure is greater than the first pressure;
the terpenes include one or more from the group consisting of limonene, humulene, pinene, linalool, caryophyllene, mycrene, eucalyptol, nerolidol, bisablol, and phytol;

Paragraph M. The method according to Paragraph K, wherein the cannabis is comprised of a new and distinct hybrid plant named Grass Weedly Junior characterized by a hybrid between *Cannabis sativa* L. ssp. *sativa* and *Cannabis sativa* L. ssp. *indica* (Lam.), within the leaves, seeds, stems, roots, or any reproductive structures, Grass Weedly Junior has:
(a) a cannabidiol content ranging from 0.00001 weight percent to 25 weight percent;
(b) a tetrahydrocannabinol content ranging from 4 weigh percent to 66 weigh percent;
(c) an energy content ranging from between 2,500 British Thermal Units per pound to 65,000 British Thermal Units per pound;
(d) a carbon content ranging from between 15 weight percent to 66 weight percent;
(e) an oxygen content ranging from between 10 weight percent to 60 weight percent;
(f) a hydrogen content ranging from between 2 weight percent to 25 weight percent;
(g) an ash content ranging from between 2 weight percent to 35 weight percent;
(h) a volatiles content ranging from between 20 weight percent to 92 weight percent;
(i) a nitrogen content ranging from between 0.5 weight percent to 20 weight percent;
(j) a sulfur content ranging from between 0.01 weight percent to 10 weight percent;
(k) a chlorine content ranging from 0.01 weight percent to 15 weight percent;
(l) a sodium content ranging from 0.01 weight percent to 20 weight percent;
(m) a potassium content ranging from 0.01 weight percent to 15 weight percent;
(n) an iron content ranging from 0.005 weight percent to 15 weight percent;
(o) a magnesium content ranging from 0.01 weight percent to 11 weight percent;
(p) a phosphorous content ranging from 0.02 weight percent to 14 weight percent;
(q) a calcium content ranging from 0.02 weight percent to 12 weight percent;
(r) a zinc content ranging from 0.01 weight percent to 7 weight percent;
(s) a cellulose content ranging from 15 weight percent to 77 weight percent;
(t) a lignin content ranging from 2 weight percent to 40 weight percent;

(u) a hemicellulose content ranging from 2 weight percent to 36 weight percent;
(v) a fat content ranging from 4 weight percent to 45 weight percent;
(w) a fiber content ranging from 5 weight percent to 75 weight percent; and
(x) a protein content ranging from 5 weight percent to 35 weight percent, as illustrated and described herein;

wherein:
the *Cannabis sativa* L. ssp. *sativa* content ranges from 15 weight percent to 85 weight percent;
the *Cannabis sativa* L. ssp. *indica* (Lam.) content ranges from 15 weight percent to 85 weight percent.

Paragraph N. The method according to Paragraph K, further comprising:
adjusting the carbon dioxide concentration above the plurality of growing assemblies to a range between 400 parts per million and 30,000 parts per million.

Paragraph O. The method according to Paragraph K, wherein the plurality of lights includes blue LEDs and red LEDs, further comprising:
(a) illuminating the plurality of growing assemblies at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again;

wherein:
the blue LEDs operate at a wavelength that ranges from 490 nanometers to 455 nanometers;
the red LEDs operate at a wavelength that ranges from 620 nanometers to 780 nanometers.

Paragraph P. The method according to Paragraph K, further comprising:
after step (m), creating a multifunctional composition by mixing at least a portion of the concentrated volatiles mixture with one or more from the group consisting of a fiber-starch material, a binding agent, a density improving textural supplement, a moisture improving textural supplement, and insects;

wherein:
the fiber-starch materials are comprised of one or more from the group consisting of cereal-grain-based materials, grass-based materials, nut-based materials, powdered fruit materials, root-based materials, tuber-based materials, and vegetable-based materials;
the binding agents are comprised of one or more from the group consisting of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, psyllium husks, sago, sugars, syrups, tapioca, vegetable gums, and xanthan gum;
the density improving textural supplements are comprised of one or more from the group consisting of extracted arrowroot starch, extracted corn starch, extracted lentil starch, extracted potato starch, and extracted tapioca starch;
the moisture improving textural supplements are comprised of one or more from the group consisting of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts;
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

Paragraph Q. A new and distinct hybrid plant named Grass Weedly Junior characterized by a hybrid between *Cannabis sativa* L. ssp. *sativa* and *Cannabis sativa* L. ssp. *indica* (Lam.), within the leaves, seeds, stems, roots, or any reproductive structures, Grass Weedly Junior has:
(a) a cannabidiol content ranging from 0.00001 weight percent to 25 weight percent;
(b) a tetrahydrocannabinol content ranging from 4 weigh percent to 66 weigh percent;
(c) an energy content ranging from between 2,500 British Thermal Units per pound to 65,000 British Thermal Units per pound;
(d) a carbon content ranging from between 15 weight percent to 66 weight percent;
(e) an oxygen content ranging from between 10 weight percent to 60 weight percent;
(f) a hydrogen content ranging from between 2 weight percent to 25 weight percent;
(g) an ash content ranging from between 2 weight percent to 35 weight percent; and
(h) a volatiles content ranging from between 20 weight percent to 92 weight percent;
(i) a nitrogen content ranging from between 0.5 weight percent to 20 weight percent;
(j) a sulfur content ranging from between 0.01 weight percent to 10 weight percent;
(k) a chlorine content ranging from 0.01 weight percent to 15 weight percent;
(l) a sodium content ranging from 0.01 weight percent to 20 weight percent;
(m) a potassium content ranging from 0.01 weight percent to 15 weight percent;
(n) an iron content ranging from 0.005 weight percent to 15 weight percent;
(o) a magnesium content ranging from 0.01 weight percent to 11 weight percent;
(p) a phosphorous content ranging from 0.02 weight percent to 14 weight percent;
(q) a calcium content ranging from 0.02 weight percent to 12 weight percent;
(r) a zinc content ranging from 0.01 weight percent to 7 weight percent;
(s) a cellulose content ranging from 15 weight percent to 77 weight percent;
(t) a lignin content ranging from 2 weight percent to 40 weight percent;
(u) a hemicellulose content ranging from 2 weight percent to 36 weight percent;
(v) a fat content ranging from 4 weight percent to 45 weight percent;
(w) a fiber content ranging from 5 weight percent to 75 weight percent; and
(x) a protein content ranging from 5 weight percent to 35 weight percent, as illustrated and described herein;

wherein:
the *Cannabis sativa* L. ssp. *sativa* content ranges from 15 weight percent to 85 weight percent;
the *Cannabis sativa* L. ssp. *indica* (Lam.) content ranges from 15 weight percent to 85 weight percent.

DESCRIPTION OF THE DRAWINGS

The accompanying figures show schematic process flowcharts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 6 shows a front view of one embodiment of a plant growing module (PGM) provided inside of a cube container conforming to the International Organization for Standardization (ISO) specifications.

FIG. 7 shows a top view of one embodiment of a plant growing module (PGM) provided inside of a cube container conforming to the International Organization for Standardization (ISO) specifications.

FIG. 17C shows a volatiles and solvent mixing system (VSMS) that is configured to mix the volatiles (VOLT) with a second solvent (SOLV2).

DETAILED DESCRIPTION

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

FIG. 1A

Figure 1A:
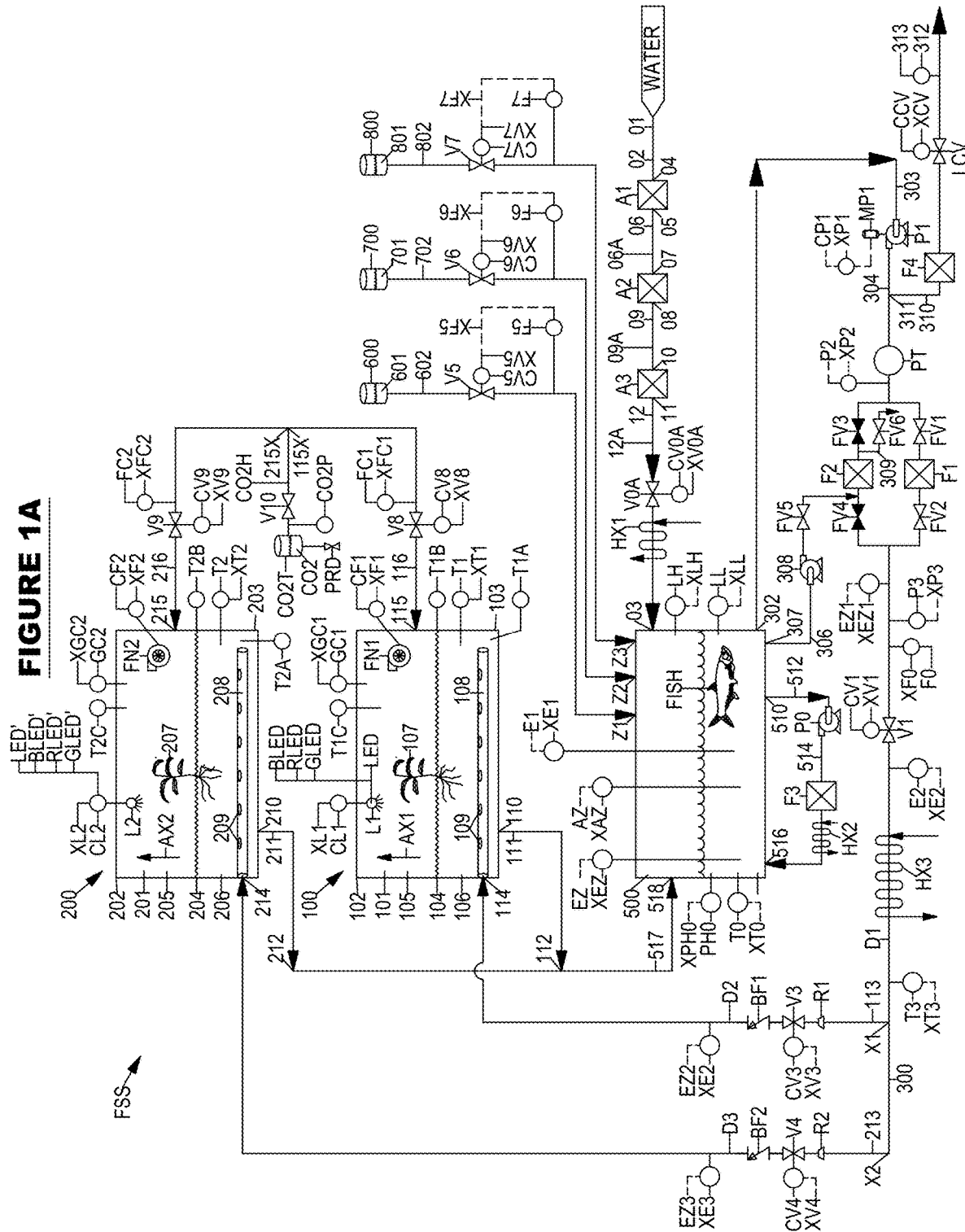
FIG. 1A depicts one non-limiting embodiment of a farming superstructure system (FSS) including a first water treatment unit (A1), a second water treatment unit (A2), a third water treatment unit (A3), a common reservoir (500), a pump (P1), a plurality of vertically stacked growing assemblies (100, 200), a fabric (104, 204) that partitions each growing assembly (100, 200) into an upper-section (105, 205) and a lower-section (106, 206), a plurality of lights (L1, L2) positioned within the upper-section (105, 205) of each growing assembly.

FIG. 1A depicts one non-limiting embodiment of a farming superstructure system (FSS) including a first water treatment unit (A1), a second water treatment unit (A2), a third water treatment unit (A3), a common reservoir (500), a pump (P1), a plurality of vertically stacked growing assemblies (100, 200), a fabric (104, 204) that partitions each growing assembly (100, 200) into an upper-section (105, 205) and a lower-section (106, 206), a plurality of lights (L1, L2) positioned within the upper-section (105, 205) of each growing assembly, a carbon dioxide tank (CO2T), a plurality of fans (FN1, FN2), a plurality of liquid supply conduits (113, 213), a liquid supply header (300), at least one filter (F1, F2), a plurality of valves (V1, V3, V4), a drain port (110, 210), and a computer (COMP).

FIG. 1A discloses a farming superstructure system (FSS). The farming superstructure system (FSS) includes a first growing assembly (100) and a second growing assembly (200) in fluid communication with a common reservoir (500). The common reservoir (500) is provided with a water supply (01) via a water supply conduit (02) and a first water inlet (03). A plurality of water treatment units (A1, A2, A2), along with a contaminant depleted water valve (V0A), and a water heat exchanger (HX1) may be installed on the water supply conduit (02).

A first water treatment unit (A1) may be installed on the water supply conduit (02). The first water treatment unit (A1) has a first input (04) and a first output (05). A water supply (01) may be provided to the first water treatment unit (A1) via a first input (04). Contaminants may be removed by the first water treatment unit (A1) to produce a first contaminant depleted water (06) that is discharged via a first output (05). In embodiments, the first water treatment unit (A1) includes a cation and is configured to remove positively charged ions from water to form a positively charged ion depleted water (06A). The "positively charged ions" include one or more from the group consisting of calcium, magnesium, sodium, and iron. In embodiments, the first contaminant depleted water (06) may be a positively charged ion depleted water (06A). In embodiments, the first water treatment unit (A1) may include a cation, an anion, a membrane, filter, activated carbon, adsorbent, or absorbent. In embodiments, an activated carbon bed may be used to remove chlorine from the water.

A second water treatment unit (A2) may be installed on the water supply conduit (02) after the first water treatment unit (A1). The second water treatment unit (A2) may include a second input (07) and a second output (08). The first contaminant depleted water (06) may be provided to the second water treatment unit (A2) via a second input (07). The first contaminant depleted water (06) may be provided to the second water treatment unit (A2) from the first output (05) of the first water treatment unit (A1). In embodiments, the positively charged ion depleted water (06A) may be provided to the second water treatment unit (A2) via a second input (07). Contaminants may be removed by the second water treatment unit (A2) to produce a second contaminant depleted water (09) that is discharged via a second output (08). In embodiments, the second water treatment unit (A2) includes an anion that is configured to remove negatively charged ions from the positively charged ion depleted water (06A) to form a negatively charged ion depleted water (09A). The "negatively charged ions" include one or more from the group consisting of iodine, chloride, and sulfate. In embodiments, the second contaminant depleted water (09) may be a negatively charged ion depleted water (09A). In embodiments, the second water treatment unit (A2) may include a cation, an anion, a membrane, filter, activated carbon, adsorbent, or absorbent.

A third water treatment unit (A3) may be installed on the water supply conduit (02) after the second water treatment unit (A2). The third water treatment unit (A3) may include a third input (10) and a third output (11). The second contaminant depleted water (09) may be provided to the third water treatment unit (A3) via a third input (10). The second contaminant depleted water (09) may be provided to the third water treatment unit (A3) from the second output (08) of the second water treatment unit (A2). In embodiments, the negatively charged ion depleted water (09A) may be provided to the third water treatment unit (A3) via a third input (10). Contaminants may be removed by the third water treatment unit (A3) to produce a third contaminant depleted water (12) that is discharged via a third output (11). In embodiments, the third water treatment unit (A3) includes a membrane that is configured to remove undesirable compounds from the negatively charged ion depleted water (09A) to form an undesirable compound depleted water (12A). The "undesirable compounds" include one or more from the group consisting of dissolved organic chemicals, viruses, bacteria, and particulates. In embodiments, the third contaminant depleted water (12) may be an undesirable compound depleted water (12A). In embodiments, the third water treatment unit (A3) may include a cation, an anion, a membrane, filter, activated carbon, adsorbent, or absorbent. In embodiments, the (10) the undesirable compounds depleted water (12A) has an electrical conductivity ranging from 0.10 microsiemens to 100 microsiemens.

In embodiments, the first water treatment unit (A1) containing a cation may be a disposable cartridge, portable tank, cylindrical vessel, automatic unit, or a continuous unit. In embodiments, the second water treatment unit (A2) containing an anion may be a disposable cartridge, portable tank, cylindrical vessel, automatic unit, or a continuous unit. In embodiments, the third water treatment unit (A3) containing a membrane may have: a diameter that ranges from 1 inch to 6 inches; and a pore size ranging from 0.0001 microns to 0.5 microns.

The common reservoir (500) is configured to accept a portion of a contaminant depleted water (06A, 09A, 12A) from the at least one water treatment unit (A1, A2, A3). In embodiments, the water treatment units (A1, A2, A3) may be configured to remove solids from the water supply (01). In embodiments, a contaminant depleted water valve (V0A) is installed on the water supply conduit (02) to regulate the amount of water transferred to the common reservoir (500) through the water supply conduit (02) and first water inlet (03). The contaminant depleted water valve (V0A) is equipped with a controller (CV0A) which sends a signal (XV0A) to and from a computer (COMP). In embodiments, a water heat exchanger (HX1) is installed on the water supply conduit (02) to control the temperature of the water transferred to the common reservoir (500) through the water supply conduit (02) and first water inlet (03). In embodiments, the water heat exchanger (HX1) increases the temperature of the water supply (01) introduced to the common reservoir (500). In embodiments, the water heat exchanger (HX1) decreases the temperature of the water supply (01) introduced to the common reservoir (500). In embodiments, the water heat exchanger (HX1) is positioned in between the contaminant depleted water valve (V0A) and the water inlet (03) of the common reservoir (500). So, it is shown that water may be treated with a plurality of water treatment units (A1, A2, A3) before being introduced to the common reservoir (500).

In embodiments, the common reservoir (500) is comprised of metal, plastic, fiberglass, composite materials, or combinations thereof, or any other conceivable material that may contain a liquid within its interior. In embodiments, the common reservoir (500) is configured to accept a water supply (01) from the water supply conduit (02). In embodiments, the common reservoir (500) may be configured to accept any permutation or combination of a water supply (01) either a first contaminant depleted water (06), second contaminant depleted water (09), or third contaminant depleted water (12), that is heated or cooled or not heated or cooled. In embodiments, the common reservoir (500) may be configured to accept any permutation or combination of a water supply (01) either a positively charged ion depleted water (06A), negatively charged ion depleted water (09A), or undesirable compounds depleted water (12A) that is heated or cooled or not heated or cooled. In embodiments, the common reservoir (500) may be configured to accept any permutation or combination of a water supply (01) from any number of water treatment units (A1, A2, A3) that includes at least a cation, an anion, a membrane, a filter, activated carbon, adsorbent, or absorbent.

In embodiments, the common reservoir (500) is equipped with an upper level switch (LH) for detecting a high level and a lower level switch (LL) for detecting a lower level. The upper level switch (LH) is configured to output a signal (XLH) to the computer (COMP) when the upper level switch (LH) is triggered by a high level of liquid within the common reservoir (500). The lower level switch (LL) is configured to output a signal (XLL) to the computer (COMP) when the lower level switch (LL) is triggered by a low level of liquid within the common reservoir (500). In embodiments, when the lower level switch (LL) sends a signal (XLL) to the computer (COMP), the contaminant depleted water valve (V0A) is opened and introduces water into the common reservoir (500) until the upper level switch (LH) is triggered thus sending a signal (XLH) to the computer (COMP) to close the contaminant depleted water valve (V0A). This level control loop including the upper level switch (LH) for detecting a high level and a lower level switch (LL) for detecting a lower level may be coupled to the operation of the contaminant depleted water valve (V0A) for introducing a water supply (01) through the water supply conduit (02) and into the common reservoir (500) via the first water inlet (03).

In embodiments, a pump (P1) is configured to accept, pressurize, and transfer liquid within the common reservoir (500) into a plurality of vertically stacked growing assemblies (100, 200). In embodiments, the pump (P1) is configured to accept, pressurize, and transfer at least a portion of the undesirable compounds depleted water (12A) transferred from the common tank (500T) into a plurality of vertically stacked growing assemblies (100, 200). Each of the plurality of vertically stacked growing assemblies (100, 200) are positioned above the common reservoir (500).

The first growing assembly (100) has an interior (101), a top (102), a bottom (103), and a longitudinal axis (AX1) extending along a height direction of the first growing assembly (100). The first growing assembly (100) has a fabric (104) that partitions the first growing assembly (100) into an upper-section (105) close to the top (102) and a lower-section (106) close to the bottom (103). The fabric (104) is used to provide structure for Grass Weedly Junior (107) to root into. For purposes of simplicity, Grass Weedly Junior (107, 207) may be referred to and is synonymous with the term cannabis (107, 207) for purposes of this disclosure. Obviously, the farming systems and methods disclosed herein pertain to any type of cannabis (107, 207) plant and not only limited to growing Grass Weedly Junior (107, 207). Growing Grass Weedly Junior (107, 207) within the farming superstructure system (FSS) is merely a non-limiting example of any type of the cannabis (107, 207) that can be grown within the farming superstructure system (FSS). In fact, any type of plant (107, 207) may be grown using the farming systems and methods disclosed herein.

Cannabis (107) rooted in the fabric (104) have roots that grow downward and extend into the lower-section (106). The first growing assembly (100) is equipped with a plurality of lights (L1) positioned within the upper-section (105) above the fabric (104). Cannabis (107) rooted in the fabric (104) grow upward extending into the upper-section (105) towards the plurality of lights (L1). The plurality of lights (L1) are configured to be controlled by a computer (COMP) to operate at a wavelength ranging from 400 nm to 700 nm. In embodiments, the lights (L1) have a controller (CL1) that sends a signal (XL1) to and from the computer (COMP). In embodiments, the lights (L1, L2) may be compact fluorescent (CFL), light emitting diode (LED), incandescent lights, fluorescent lights, or halogen lights. In embodiments, light emitting diodes are preferred.

In embodiments, a first plurality of lights (L1) in the first growing assembly (100) include a first plurality of light emitting diodes (LED). In embodiments, the first plurality of light emitting diodes (LED) include blue LEDs (BLED), red LEDS (RLED), and/or green LEDS (GLED). In embodiments, the first plurality of light emitting diodes (LED) in the first growing assembly (100) include one or two or more from the group consisting of blue LEDs (BLED), red LEDS (RLED), and green LEDS (GLED).

In embodiments, a second plurality of lights (L2) in the second growing assembly (200) include a second plurality of light emitting diodes (LED'). In embodiments, the second plurality of light emitting diodes (LED') include blue LEDs (BLED'), red LEDS (RLED'), and/or green LEDS (GLED'). In embodiments, the second plurality of light emitting diodes (LED') in the second growing assembly (200) include one or two or more from the group consisting of blue LEDs (BLED'), red LEDS (RLED'), and green LEDS (GLED').

In embodiments, the blue LEDs (BLED, BLED') operate at a wavelength that ranges from 490 nanometers (nm) to 455 nm. In embodiments, the red LEDs (RLED, RLED') operate at a wavelength that ranges from 620 nm to 780 nm. In embodiments, the green LEDs (GLED, GLED') operate at a wavelength that ranges from 490 nm to 577 nm. In embodiments, the plurality of light emitting diodes (LED) are configured to be controlled by a computer (COMP) to operate at a wavelength ranging from 490 nm to 780 nm. In embodiments, the plurality of light emitting diodes (LED) are configured to be controlled by a computer (COMP) to operate at a wavelength ranging from 400 nm to 700 nm.

In embodiments, the first plurality of light emitting diodes (LED) and second plurality of light emitting diodes (LED") are configured to operate in the following manner:
  (a) illuminating plants with blue LEDs (BLED, BLED) and red LEDs (RLED, RLED); and
  (b) illuminating the plants nanometers with green LEDs (GLED, GLED);
wherein:
  the blue LEDs (BLED, BLED') operate at a wavelength that ranges from 490 nanometers to 455 nanometers;
  the red LEDs (RLED, RLED') operate at a wavelength that ranges from 620 nanometers to 780 nanometers;
  the green LEDs (GLEDGLED') operate at a wavelength that ranges from 490 nanometers to 577 nanometers.

In embodiments, the first plurality of light emitting diodes (LED) and second plurality of light emitting diodes (LED) are configured to operate in the following manner:
  (a) providing:
    (a1) a first growing assembly (100) having a first plurality of light emitting diodes (LED), the first plurality of light emitting diodes (LED) in the first growing assembly (100) include blue LEDs (BLED), red LEDS (RLED), and green LEDS (GLED);
    (a2) a second growing assembly (200) having a second plurality of light emitting diodes (LED), the second plurality of light emitting diodes (LED') in the second growing assembly (200) include blue LEDs (BLED'), red LEDS (RLED'), and green LEDS (GLED');
  (b) illuminating the interiors of the first growing assembly (100) and second growing assembly (200) with green LEDs (GLED, GLED') and optionally with blue LEDs (BLED, BLED') or red LEDs (RLED, RLED'); and
  (c) illuminating the interiors of the first growing assembly (100) and second growing assembly (200) with blue LEDs (BLED, BLED') and red LEDs (RLED, RLED'); and
wherein:
  the blue LEDs (BLED, BLED') operate at a wavelength that ranges from 490 nanometers to 455 nanometers;
  the red LEDs (RLED, RLED') operate at a wavelength that ranges from 620 nanometers to 780 nanometers;
  the green LEDs (GLED, GLED') operate at a wavelength that ranges from 490 nanometers to 577 nanometers.

In embodiments, the disclosure provides for a farming method, including:
  (a) providing a farming superstructure system (FSS), including:
    (a1) a first water treatment unit (A1) including a cation configured to remove positively charged ions from water to form a positively charged ion depleted water (06A), the positively charged ions are comprised of one or more from the group consisting of calcium, magnesium, sodium, and iron;
    (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
    (a3) a first growing assembly (100) having a first plurality of light emitting diodes (LED), the first plurality of light emitting diodes (LED) in the first growing assembly (100) include blue LEDs (BLED) and red LEDS (RLED), and optionally green LEDS (GLED);
    (a4) a second growing assembly (200) having a second plurality of light emitting diodes (LED'), the second plurality of light emitting diodes (LED') in the second growing assembly (200) include blue LEDs (BLED') and red LEDS (RLED'), and optionally green LEDS (GLED');
  (b) providing a source of water;
  (c) removing positively charged ions from the water of step (b) to form a positively charged ion depleted water;
  (d) removing negatively charged ions from the water after step (c) to form a negatively charged ion depleted water;
  (e) mixing the negatively charged ion depleted water after step (d) with one or more from the group consisting of macro-nutrients, micro-nutrients, and a pH adjustment to form a liquid mixture;
  (f) pressurizing the liquid mixture of step (e) to form a pressurized liquid mixture;
  (g) splitting the pressurized liquid mixture into a plurality of pressurized liquid mixtures;
  (h) transferring the plurality of pressurized liquid mixtures to each growing assembly;
  (i) illuminating the interiors of the first growing assembly (100) and second growing assembly (200) with blue LEDs (BLED, BLED') and red LEDs (RLED, RLED'); and
  (j) optionally illuminating the interiors of the first growing assembly (100) and second growing assembly (200) with green LEDs (GLED, GLED');
wherein:
  the blue LEDs (BLED, BLED') operate at a wavelength that ranges from 490 nanometers to 455 nanometers;
  the red LEDs (RLED, RLED') operate at a wavelength that ranges from 620 nanometers to 780 nanometers;
  the green LEDs (GLED, GLED') operate at a wavelength that ranges from 490 nanometers to 577 nanometers;
  the positively charged ions are comprised of one or more from the group consisting of calcium, magnesium, sodium, and iron;
  the negatively charged ions are comprised of one or more from the group consisting of iodine, chloride, and sulfate;
  the macro-nutrients are comprised of one or more from the group consisting of nitrogen, phosphorus, potassium, calcium, magnesium, and sulfur;
  the micro-nutrients are comprised of one or more from the group consisting of iron, manganese, boron, molybdenum, copper, zinc, sodium, chlorine, and silicon;
  the pH adjustment solution is comprised of one or more from the group consisting acid, nitric acid, phosphoric acid, potassium hydroxide, sulfuric acid, organic acids, citric acid, and acetic acid;

the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:
(a) providing a farming superstructure system (FSS), including:
  (a1) a first growing assembly (100) having a first plurality of light emitting diodes (LED), the first plurality of light emitting diodes (LED) in the first growing assembly (100) blue LEDs (BLED) and red LEDS (RLED), and optionally green LEDS (GLED);
  (a2) a second growing assembly (200) having a second plurality of light emitting diodes (LED'), the second plurality of light emitting diodes (LED') in the second growing assembly (200) include blue LEDs (BLED') and red LEDS (RLED'), and optionally green LEDS (GLED');
(b) illuminating the interiors of the first growing assembly (100) and second growing assembly (200) with blue LEDs (BLED, BLED') and red LEDs (RLED, RLED'); and
(c) optionally illuminating the interiors of the first growing assembly (100) and second growing assembly (200) with green LEDs (GLED, GLED');
wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers;
the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:
(a) providing a farming superstructure system (FSS), including:
  (a1) a first growing assembly (100) having a first plurality of light emitting diodes (LED), the first plurality of light emitting diodes (LED) in the first growing assembly (100) blue LEDs (BLED) and red LEDS (RLED), and optionally green LEDS (GLED);
  (a2) a second growing assembly (200) having a second plurality of light emitting diodes (LED'), the second plurality of light emitting diodes (LED') in the second growing assembly (200) include blue LEDs (BLED') and red LEDS (RLED'), and optionally green LEDS (GLED');
  (a3) a carbon dioxide tank (CO2T), at least one carbon dioxide valve (V8, V9, V10), the at least one carbon dioxide valve (V8, V9, V10) is configured to take a pressure drop of greater than 50 pounds per square inch, carbon dioxide is made available to the first growing assembly (100) or second growing assembly (200);
(b) illuminating the interiors of the first growing assembly (100) and second growing assembly (200) with blue LEDs (BLED, BLED') and red LEDs (RLED, RLED'); and
(c) optionally illuminating the interiors of the first growing assembly (100) and second growing assembly (200) with green LEDs (GLED, GLED');
(d) adjusting the carbon dioxide concentration within the first growing assembly (100) or second growing assembly (200) to a range between 400 parts per million and 20,000 parts per million;
wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers;
the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

The second growing assembly (200) has an interior (201), a top (202), a bottom (203), and a longitudinal axis (AX2) extending along a height direction of the first growing assembly (200). The second growing assembly (200) has a fabric (204) that partitions the second growing assembly (200) into an upper-section (205) close to the top (202) and a lower-section (206) close to the bottom (203). The fabric (204) is used to provide structure for cannabis (207) to root into. Cannabis (207) rooted in the fabric (204) have roots that grow downward and extend into the lower-section (206). The second growing assembly (200) is equipped with a plurality of lights (L2) positioned within the upper-section (205) above the fabric (204). Cannabis (207) rooted in the fabric (204) grow upward extending into the upper-section (205) towards the plurality of lights (L2). The plurality of lights (L2) are configured to be controlled by a computer (COMP) to operate at a wavelength ranging from 400 nm to 700 nm. In embodiments, the lights (L2) have a controller (CL2) that sends a signal (XL2) to and from the computer (COMP).

In embodiments, the farming superstructure system (FSS) is equipped with a carbon dioxide tank (CO2T). The carbon dioxide tank (CO2T) contains pressurized carbon dioxide (CO2) and is equipped with a carbon dioxide pressure sensor (CO2P). A carbon dioxide supply header (CO2H) is connected to the carbon dioxide tank (CO2T). A first carbon dioxide supply valve (V10) is installed on the carbon dioxide supply header (CO2H) and is configured to take a pressure drop of greater than 50 pounds per square inch (PSI). The first growing assembly (100) is equipped with a CO2 input (115) that is connected to a CO2 supply conduit (116). The second growing assembly (200) is also equipped with a CO2 input (215) that is connected to a CO2 supply conduit (216).

The CO2 supply conduit (116) of the first growing assembly (100) is connected to the carbon dioxide supply header (CO2H) via a CO2 header connection (115X). The CO2 supply conduit (116) of the first growing assembly (100) is configured to transfer carbon dioxide into the first interior (101) of the first growing assembly (100). In embodiments, a second carbon dioxide supply valve (V8) is installed on the CO2 supply conduit (116) of the first growing assembly (100). The second carbon dioxide supply valve (V8) is equipped with a controller (CV8) that sends a signal (XV8) to and from a computer (COMP). In embodiments, a CO2 flow sensor (FC1) is installed on the CO2 supply conduit (116) of the first growing assembly (100). The CO2 flow sensor (FC1) sends a signal (XFC1) to the computer (COMP). In embodiments, a gas quality sensor (GC1) is installed on the first growing assembly (100) to monitor the concentration of carbon dioxide within the first interior (101). The gas quality sensor (GC1) is equipped to send a signal (XGC1) to the computer (COMP).

The CO2 supply conduit (216) of the second growing assembly (200) is connected to the carbon dioxide supply header (CO2H) via a CO2 header connection (215X). The CO2 supply conduit (216) of the second growing assembly (200) is configured to transfer carbon dioxide into the second interior (201) of the second growing assembly (100). In embodiments, a third carbon dioxide supply valve (V9) is installed on the CO2 supply conduit (216) of the second growing assembly (200). The third carbon dioxide supply valve (V9) is equipped with a controller (CV9) that sends a signal (XV9) to and from a computer (COMP). In embodiments, a CO2 flow sensor (FC2) is installed on the CO2 supply conduit (216) of the second growing assembly (200). The CO2 flow sensor (FC2) sends a signal (XFC2) to the computer (COMP). In embodiments, a gas quality sensor (GC2) is installed on the second growing assembly (200) to monitor the concentration of carbon dioxide within the second interior (201). The gas quality sensor (GC2) is equipped to send a signal (XGC2) to the computer (COMP).

In embodiments, the carbon dioxide concentration in the upper-section (105, 205) of each growing assembly ranges from between greater than 400 parts per million to 30,000 parts per million. In embodiments, the gas quality sensor (GC2) is equipped to send a signal (XGC2) to the computer (COMP) to operate the first, second, or third carbon dioxide supply valves (V10, V8, V9).

At least one fan (FN1) is positioned in the upper-section (105) of the first growing assembly (100). The fan (FN1) is configured to blow air onto the cannabis (107). The fan (FN1) is configured to distribute a mixture of air and CO2 onto the cannabis (107). The fan (FN1) is equipped with a controller (CF1) that sends a signal (XF1) to and from a computer (COMP).

A plurality of fans (FN2) are positioned in the upper-section (205) of the second growing assembly (200). The fans (FN2) are configured to blow air onto the cannabis (207). In embodiments, the fans blow air and the air is comprised of a gas, vapor, and solid particulates. In embodiments, the gas within air may be oxygen, carbon dioxide, or nitrogen. In embodiments, the vapor within the air may be water vapor. In embodiments, the solid particulates within air may be dust, dirt, or pollen. The fans (FN2) are configured to distribute a mixture of air and CO2 onto the cannabis (207). The fans (FN2) are equipped with a controller (CF2) that sends a signal (XF2) to and from a computer (COMP). Each of the fans (FN1, FN2) is configured to operate at a RPM less than 6,000 RPM. In embodiments, it is preferred to operate the fans (FN1, FN2) at a RPM less than 6,000 so that the velocity of air blown onto the cannabis ranges from 0.5 feet per second to 50 feet per second.

Figure 12:
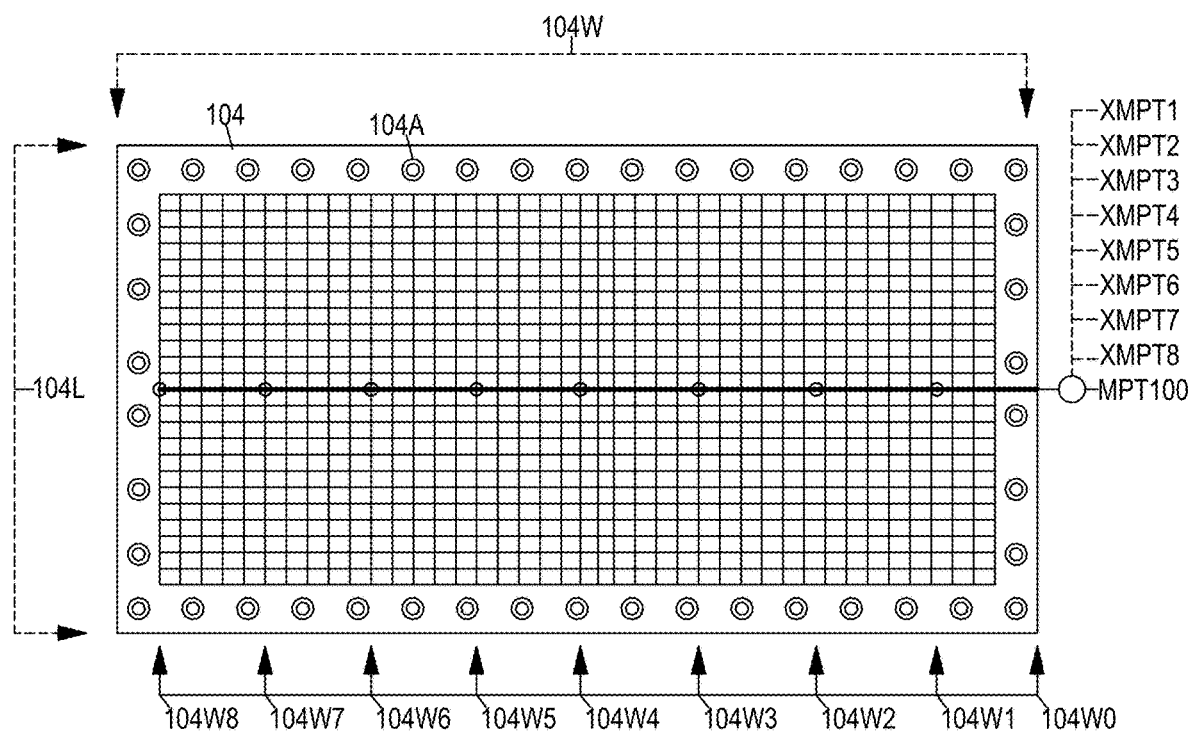
FIG. 12 shows one non-limiting embodiment of a fabric (104) used in a growing assembly (100), the fabric (104) having a multi-point temperature sensor (MPT100) connected thereto for measuring temperatures at various lengths along the sensor's length.
Figure 13:
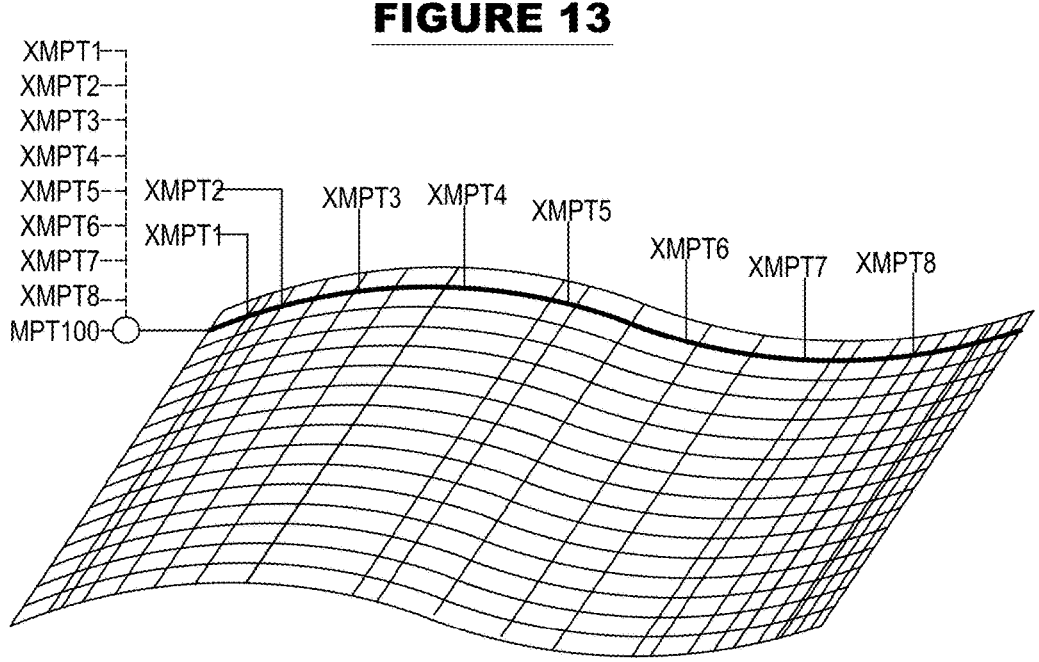
FIG. 13 shows another one non-limiting embodiment of a fabric (104) used in a growing assembly (100).

The first growing assembly (100) is equipped with a temperature sensor (T1) to monitor the temperature within the first interior (101). The temperature sensor (T1) is configured to send a signal (XT1) to the computer (COMP). In embodiments, the temperature sensor (T1) may be a multi-point temperature sensor (MPT100) that is connected to the fabric (104) for measuring temperatures at various lengths along the sensor's length and long the length of the fabric (104), as depicted in FIGS. 12 and 13.

The second growing assembly (200) is equipped with a temperature sensor (T2) to monitor the temperature within the second interior (201). The temperature sensor (T2) is configured to send a signal (XT2) to the computer (COMP). In embodiments, the temperature sensor (T2) may be a multi-point temperature sensor (MPT100) that is connected to the fabric (204) for measuring temperatures at various lengths along the sensor's length and long the length of the fabric (204), as depicted in FIGS. 12 and 13.

In embodiments, each growing assembly (100, 200) is equipped with an upper temperature sensor (T1C, T2C) positioned within the upper-section (105, 205), a partition temperature sensor (T1B, T2B) positioned at the fabric (104), and a lower temperature sensor (T1A, T2A) positioned within the lower-section (106, 206). Preferably the partition temperature sensor (T1B) is a multi-point temperature sensor (MPT100) that is integrated with the fabric (104) as disclosed in FIGS. 12 and 13.

In embodiments, the upper temperature sensor (T1C, T2C) is configured to input a signal (XT1C, XT2C) (not shown) to the computer (COMP). In embodiments, the partition temperature sensor (T1B, T2B) is configured to input a signal (XT1B, XT2B) (not shown) to the computer (COMP). In embodiments, the lower temperature sensor (T1A, T2B) is configured to input a signal (XT1A, XT2A) (not shown) to the computer (COMP). In embodiments, during the day-time, the upper-section (105, 205) has a temperature that is greater than the temperature within lower-section (106, 206). In embodiments, during the night-time, the upper-section (105, 205) has a temperature that is less than the temperature within the lower-section (106, 206).

A first liquid distributor (108) is positioned in the lower-section (106) of the first growing assembly (100) below the fabric (104) and equipped with a plurality of restrictions (109) installed thereon. In embodiments, the restrictions (109) of the first liquid distributor (108) are spray nozzles, spray balls, or apertures. Each restriction (109) is configured to accept pressurized liquid from the pump (P1) and introduce the liquid into the lower-section (106) of the first growing assembly (100) while reducing the pressure of the liquid that passes through each restriction (109). The first liquid distributor (108) is connected to a first liquid supply conduit (113) via a liquid input (114). The first liquid distributor (108) is configured to receive liquid from a first liquid supply conduit (113).

A second liquid distributor (208) is positioned in the lower-section (206) of the second growing assembly (200) below the fabric (204) and equipped with a plurality of restrictions (209) installed thereon. In embodiments, the restrictions (209) of the second liquid distributor (208) are spray nozzles, spray balls, or apertures. Each restriction (209) is configured to accept pressurized liquid from the pump (P1) and introduce the liquid into the lower-section (206) of the second growing assembly (200) while reducing the pressure of the liquid that passes through each restriction (209). The second liquid distributor (208) is connected to a second liquid supply conduit (213) via a liquid input (214). The second liquid distributor (208) is configured to receive liquid from a second liquid supply conduit (213).

The first liquid supply conduit (113) is connected to a liquid supply header (300) via a first connection (X1). The second liquid supply conduit (213) is connected to a liquid supply header (300) via a second connection (X2). The liquid supply header (300) is connected to the pump discharge conduit (304). In embodiments, the liquid supply header (300) has a diameter (D1) that is greater than both the first smaller diameter (D2) of the first liquid supply conduit (113) and the second smaller diameter (D3) of the second liquid supply conduit (213). A first reducer (R1) may be positioned on the first liquid supply conduit (113) in between the first connection (X1) to the liquid supply header (300) and the liquid input (114) to the first growing assembly (100). A second reducer (R2) may be positioned on the second liquid supply conduit (213) in between the second connection (X2) to the liquid supply header (300) and the liquid input (214) to the second growing assembly (200).

A first growing assembly liquid supply valve (V3) may be positioned on the first liquid supply conduit (113) in between the liquid supply header (300) and the first growing assembly (100). The first growing assembly liquid supply valve (V3) has a controller (CV3) that is configured to input and output a signal (XV3) to or from the computer (COMP). A second growing assembly liquid supply valve (V4) may be positioned on the second liquid supply conduit (213) in between the liquid supply header (300) and the second growing assembly (200). The second growing assembly liquid supply valve (V4) has a controller (CV4) that is configured to input and output a signal (XV4) to or from the computer (COMP).

A back-flow prevention valve (BF1) may be positioned on the first liquid supply conduit (113) in between the liquid supply header (300) and the first growing assembly (100). FIG. 1A shows the back-flow prevention valve (BF1) positioned in between the first growing assembly liquid supply valve (V3) and the first growing assembly (100). A back-flow prevention valve (BF2) may be positioned on the second liquid supply conduit (213) in between the liquid supply header (300) and the second growing assembly (200). FIG. 1A shows the back-flow prevention valve (BF2) positioned in between the second growing assembly liquid supply valve (V4) and the second growing assembly (200).

A second oxygen emitter (EZ2) may be positioned on the first liquid supply conduit (113) in between the liquid supply header (300) and the first growing assembly (200). The second oxygen emitter (EZ2) is configured to oxygenate a portion of the liquid that flows through the first liquid supply conduit (113). The second oxygen emitter (EZ2) inputs signal (XEZ3) from a computer (COMP). A third oxygen emitter (EZ3) may be positioned on the second liquid supply conduit (213) in between the liquid supply header (300) and the second growing assembly (200). The third oxygen emitter (EZ3) is configured to oxygenate a portion of the liquid that flows through the second liquid supply conduit (213). The third oxygen emitter (EZ3) inputs signal (XEZ3) from a computer (COMP).

In embodiments, the oxygen emitter is an electrolytic cell configured to produce oxygenated water. In embodiments, oxygenated water produced by the electrolytic cell may have microbubbles and nanobubbles of oxygen suspended within it. In embodiments, the oxygen emitter is an electrolytic cell which generates microbubbles and nanobubbles of oxygen in a liquid, which bubbles are too small to break the surface tension of the liquid, resulting in a liquid that is supersaturated with oxygen. "Supersaturated" means oxygen at a higher concentration than normal calculated oxygen solubility at a particular temperature and pressure. In embodiments, the very small oxygen bubbles remain suspended in the liquid, forming a solution supersaturated in oxygen. The use of supersaturated or oxygenated water for enhancing the growth of cannabis may be incorporated into the FSS. Electrolytic generation of microbubbles or nanobubbles of oxygen for increasing the oxygen content of flowing liquid may be incorporated into the FSS. In embodiments, the production of oxygen and hydrogen by the electrolysis of water may be used to enhance the efficiency of the FSS.

In embodiments, an electrolytic cell is comprised of an anode and a cathode. A current is applied across an anode and a cathode of the electrolytic cell which are immersed in a liquid. Hydrogen gas is produced at the cathode and oxygen gas is produced at the anode. In embodiments, the electrolytic cell tends to deactivate and have a limited life if exposed to the positively charged ions, negatively charged ions, or undesirable compounds. Therefore, a sophisticated water treatment unit is needed for the electrolytic cell to work properly deactivate by unpredictable amounts of positively charged ions, remove negatively charged ions, or undesirable components. The roots of the cannabis in the lower section (106, 206) are healthier when contacted with an oxygenated liquid. Further, oxygenated and/or supersaturated water inhibits the growth of deleterious fungi on the fabric (104, 204). In embodiments, the oxygen emitter may be a sparger for increasing the oxygen content of a liquid by sparging with air or oxygen. In embodiments, the oxygen emitter may be a microbubble generator that achieves a bubble size of about 0.10 millimeters to about 3 millimeters in diameter. In embodiments, the oxygen emitter may be a microbubble generator for producing microbubbles, ranging in size from 0.1 to 100 microns in diameter, by forcing air into the fluid at high pressure through an orifice.

The common reservoir (500) is configured to accept a water supply (01). In embodiments, the common reservoir (500) is configured to accept a water supply (01) that has passed through one or more water treatment units (A1, A2, A3). In embodiments, the common reservoir (500) is configured to accept a portion of the undesirable compounds depleted water (12A).

The common reservoir (500) is configured to accept macro-nutrients (601) from a macro-nutrient supply tank (600), micro-nutrients (701) from a micro-nutrient supply tank (700), and a pH adjustment solution (801) from a pH adjustment solution supply tank (800). In embodiments, the macro-nutrients (601) include one or more from the group consisting of nitrogen, phosphorus, potassium, calcium, magnesium, and sulfur. In embodiments, the micro-nutrients (701) include one or more from the group consisting of iron, manganese, boron, molybdenum, copper, zinc, sodium, chlorine, and silicon. In embodiments, the pH adjustment solution (801) includes one or more from the group consisting acid, nitric acid, phosphoric acid, potassium hydroxide, sulfuric acid, organic acids, citric acid, and acetic acid.

In embodiments, the macro-nutrient supply tank (600) is connected to the common reservoir (500) via a macro-nutrient transfer conduit (602) and a macro-nutrient reservoir input (Z1). A macro-nutrient supply valve (V5) is installed on the macro-nutrient transfer conduit (602). The macro-nutrient supply valve (V5) is equipped with a controller (CV5) that inputs and outputs a signal (XV5) to and from the computer (COMP). A macro-nutrient flow sensor (F5) is installed on the macro-nutrient transfer conduit (602) and configured to output a signal (XF5) to or from a computer (COMP). Macro-nutrients (601) may be transferred to the interior of the common reservoir (500) via a macro-nutrient transfer conduit (602) by operation with a macro-nutrient supply tank (600) load cell (604) to measure the loss-in-mass of the macro-nutrients (601) within the macro-nutrient supply tank (600) or the macro-nutrient transfer conduit (602). Macro-nutrients (601) are introduced into the interior of the common reservoir (500) beneath the liquid level via a diptube (606).

In embodiments, the micro-nutrient supply tank (700) is connected to the common reservoir (500) via a micro-nutrient transfer conduit (702) and a micro-nutrient reservoir input (Z2). A micro-nutrient supply valve (V6) is installed on the micro-nutrient transfer conduit (702). The micro-nutrient supply valve (V6) is equipped with a controller (CV6) that inputs and outputs a signal (XV6) to and from the computer (COMP). A micro-nutrient flow sensor (F6) is installed on the micro-nutrient transfer conduit (702) and configured to output a signal (XF6) to or from a computer (COMP). Micro-nutrients (701) may be transferred to the interior of the common reservoir (500) via a micro-nutrient transfer conduit (702) by operation with a micro-nutrient supply tank (700) load cell (704) to measure the loss-in-mass of the micro-nutrients (701) within the micro-nutrient supply tank (700) or the micro-nutrient transfer conduit (702). Macro-nutrients (601) are introduced into the interior of the common reservoir (500) beneath the liquid level via a diptube (606) (not shown).

In embodiments, the pH adjustment solution supply tank (800) is connected to the common reservoir (500) via a pH adjustment solution transfer conduit (802) and a pH adjustment solution reservoir input (Z3). A pH adjustment solution supply valve (V8) is installed on the pH adjustment solution transfer conduit (802). The pH adjustment solution supply valve (V8) is equipped with a controller (CV8) that inputs and outputs a signal (XV8) to and from the computer (COMP). A pH adjustment solution flow sensor (F7) is installed on the pH adjustment solution transfer conduit (802) and configured to output a signal (XF7) to or from a computer (COMP). A pH adjustment solution (801) may be transferred to the interior of the common reservoir (500) via a pH adjustment solution transfer conduit (802) by operation with a pH adjustment solution supply tank (800) load cell (804) to measure the loss-in-mass of the pH adjustment solution (801) within the pH adjustment solution supply tank (800) or the pH adjustment solution transfer conduit (802). The pH adjustment solution (801) are introduced into the interior of the common reservoir (500) beneath the liquid level via a diptube (806) (not shown).

The common reservoir (500) is configured to accept liquid drained from each growing assembly (100, 200). The common reservoir (500) is configured to accept liquid drained from the first growing assembly (100). A drain port (110) is installed on the lower-section (106) of the first growing assembly (100) and is configured to drain liquid into a common reservoir (500) via a drain conduit (111). In embodiments, the first growing assembly (100) is connected to the common reservoir (500) via a drain conduit (111). The common reservoir (500) is configured to accept liquid drained from the second growing assembly (200). A drain port (210) is installed on the lower-section (206) of the second growing assembly (200) and is configured to drain liquid into a common reservoir (500) via a drain conduit (211). In embodiments, the second growing assembly (200) is connected to the common reservoir (500) via a drain conduit (211). It is preferable to drain liquid from each growing assembly at a velocity less than 3 feet per second.

Figure 8:
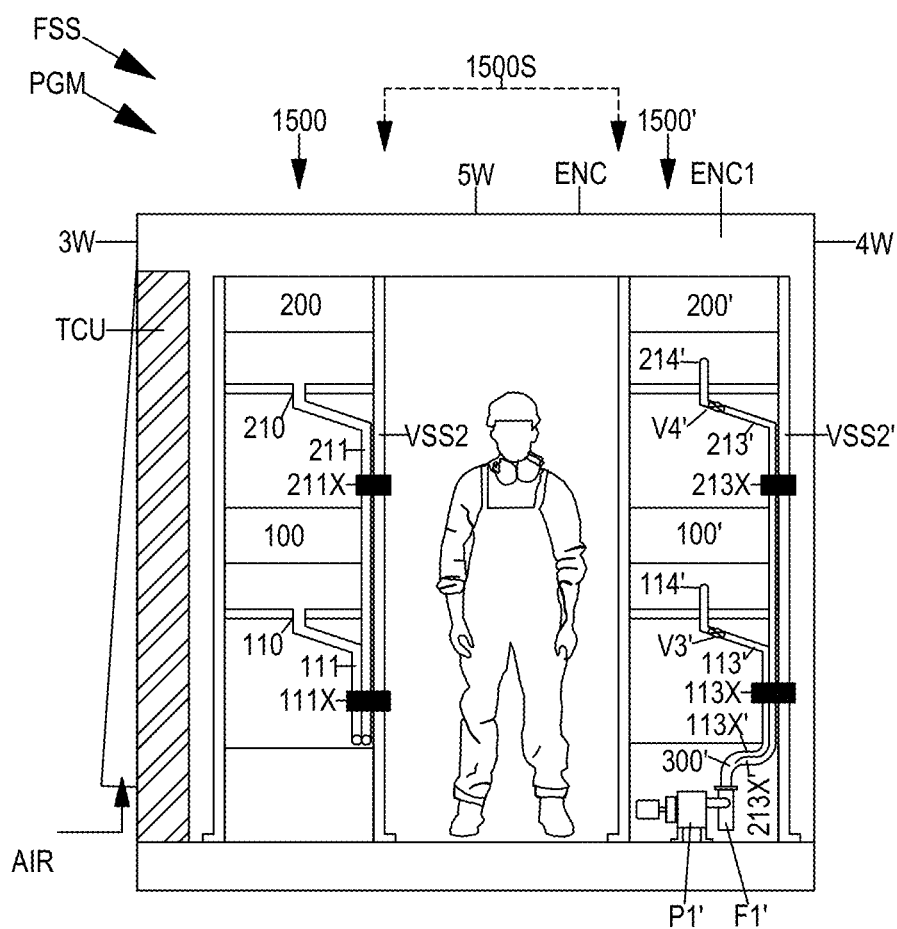
FIG. 8 shows a first side view of one embodiment of a plant growing module (PGM).

In embodiments, the drain conduit (111) is connected at one end to the first growing assembly (100) via a drain port (110) and connected at another end to the common reservoir (500) via a common drain conduit (517). In embodiments, the drain conduit (211) is connected at one end to the second growing assembly (200) via a drain port (210) and connected at another end to the common reservoir (500) via a common drain conduit (517). The common drain conduit (517) is connected at one end to the common reservoir (500) via a drain input (518) and at another end to the first drain conduit (111) via a first drain connection (112). The common drain conduit (517) is connected at one end to the common reservoir (500) via a drain input (518) and at another end to the second drain conduit (211) via a second drain connection (212). In embodiments, the common drain conduit (517) is connected to both drain conduits (111, 211) from both growing assemblies (100, 200) and is configured to combine the liquid contents of both drain conduits (111, 211) prior to introducing them into the common reservoir (500). In embodiments, as shown in FIG. 8, there is no common drain conduit (517) and each drain conduit (111, 211) of the growing assemblies (100, 200) drains directly into the common reservoir (500).

The interior of the common reservoir (500) is configured to hold water, macro-nutrients (601), micro-nutrients (701) from a micro-nutrient supply tank (700), and a pH adjustment solution (801). In embodiments, the common reservoir (500) is equipped with a reservoir pH sensor (PH0) that is configured to input a signal (XPH0) to a computer (COMP). In embodiments, the acidity of the water is measured by the reservoir pH sensor (PH0) and adjusted to a desirable range from 5.15 to 6.75. In embodiments, the common reservoir (500) is equipped with a reservoir temperature sensor (T0) that is configured to input a signal (XT0) to a computer (COMP). In embodiments, the common reservoir (500) is equipped with a reservoir oxygen emitter (EZ) that is configured to input a signal (XEZ) to a computer (COMP). In embodiments, the common reservoir (500) is equipped with a reservoir electrical conductivity sensor (E1) that is configured to input a signal (XE1) to a computer (COMP).

In embodiments, the common reservoir (500) is equipped with a reservoir recirculation pump (P0) followed by a reservoir recirculation filter (F3) to remove solids from the common reservoir (500). In embodiments, the common reservoir (500) is equipped with a reservoir heat exchanger (HX2) to maintain a temperature of the liquid contents within the common reservoir (500). In embodiments, the common reservoir (500) is equipped with a reservoir recirculation pump (P0) followed by a reservoir heat exchanger (HX2) to maintain a temperature of the liquid contents within the common reservoir (500). The common reservoir (500) has a reservoir recirculation outlet (510) that is connected to a reservoir recirculation pump suction conduit (512). The reservoir recirculation pump suction conduit (512) is connected to a reservoir recirculation pump (P0). The reservoir recirculation pump (P0) is connected to a reservoir recirculation pump discharge conduit (514) that transfers liquid back to the common reservoir (500) via a reservoir recirculation inlet (516). In embodiments, a reservoir recirculation filter (F3) is installed on the reservoir recirculation pump discharge conduit (514). In embodiments, a reservoir heat exchanger (HX2) is installed on the reservoir recirculation pump discharge conduit (514). In embodiments, a reservoir heat exchanger (HX2) is installed on the reservoir recirculation pump discharge conduit (514) after the reservoir recirculation filter (F3). In embodiments, the reservoir heat exchanger (HX2) may increase the temperature of the liquid passing through it. In embodiments, the reservoir heat exchanger (HX2) may decrease the temperature of the liquid passing through it.

The common reservoir (500) is connected to a pump (P1) via a pump suction conduit (303). The pump suction conduit (303) is connected at one end to the common reservoir (500) via a reservoir transfer outlet (302) and connected at the other end to the pump (P1). The pump (P1) is equipped with a motor (MP1) and a controller (CP1) which is configured to input and output a signal (XP1) to and from a computer (COMP). A pump discharge conduit (304) is connected to the pump (P1). The liquid supply header (300) may be synonymous with the pump discharge conduit (304) in that they both accept a portion of pressurized liquid that was provided by the pump (P1).

In embodiments, a pressure tank (PT) is installed on the pump discharge conduit (304). In embodiments, the pressure tank (PT) may be pressurized by the pump (P1). The pressure tank (PT) serves as a pressure storage reservoir in which a liquid is held under pressure. The pressure tank (PT) enables the system to respond more quickly to a temporary demand, and to smooth out pulsations created by the pump (P1). In embodiments, the pressure tank (PT) serves as accumulator to relieve the pump (P1) from constantly operating. In embodiments, the pressure tank (PT) is a cylindrical tank rated for a maximum pressure of 200 PSI or 600 PSI. In embodiments, the pressure tank (PT) is a cylindrical tank that has a length to diameter ratio ranging from 1.25 to 2.5.

A level control discharge conduit (310) is connected to the pump discharge conduit (304) via a connection (311). The level control discharge conduit (310) is configured to pump the contents of the common reservoir (500) away from the system for any number of reasons. Clean-out, replenishing the liquid within the common reservoir (500) or to bleed off some of the liquid contents within may be some purposes for utilizing the level control discharge conduit (310). A filter (F4) is installed on the level control discharge conduit (310). A level control valve (LCV) is installed on the level control discharge conduit (310) and is equipped with a controller (CCV) that sends a signal (XCV) to or from the computer (COMP). The filter (F4) preferably is installed upstream of the level control valve (LCV) to that solids do not clog the level control valve (LCV). Preferably the connection (311) for the level control discharge conduit (310) is connected as close as possible to the pump (P1) on the pump discharge conduit (304) so that if the filters (F1, F2) on the pump discharge conduit (304) clog, there is still a way to drain liquid from the system. A waste treatment unit (312) may be placed on the level control discharge conduit (310) to destroy any organic molecules, waste, bacteria, protozoa, helminths, or viruses that may be present in the liquid. In embodiments, the waste treatment unit (312) is an ozone unit (313) configured to destroy organic molecules, waste, bacteria, protozoa, helminths, or viruses via oxidation.

At least one filter (F1, F2) may be installed on the pump discharge conduit (304). FIG. 1A shows two filters (F1, F2) configured to operate in a cyclic-batch mode where when one is on-line in a first mode of normal operation, the other is off-line and undergoing a back-flush cycle in a second mode of operation. This is depicted in FIG. 1A wherein the first filter (F1) is on-line and filtering the liquid discharged from the pump (P1) while the second filter (F2) is off-line. The first filter (F1) is shown to have a first filter inlet valve (FV1) and a first filter outlet valve (FV2) both of which are open in FIG. 1. The second filter (F2) is shown to have a second filter inlet valve (FV3) and a second filter outlet valve (FV4) both of which are shown in the closed position as indicted by darkened-in color of the valves (FV3, FV4). The second filter (F2) is shown in the back-flush mode of operation while the first filter (F1) is shown in the normal mode of operation. While in the back-flush mode of operation, the second filter (F2) is shown accepting a source of liquid from the common reservoir (500) via a filter back-flush supply conduit (306).

The common reservoir (500) is equipped with a filter back-flush outlet (307) that is connected to a filter back-flush supply conduit (306). The filter back-flush supply conduit (306) is connected at one end to the common reservoir (500) via a filter back-flush outlet (307) and at another end to the filter back-flush pump (308). The filter back-flush pump (308) is connected to the filter back-flush discharge conduit (309). The filter back-flush discharge conduit (309) has a filter back-flush supply valve (FV5) installed thereon to provide pressurized liquid from the common reservoir (500) to the second filter (F2) operating in the second mode of back-flush operation. The filter back-flush supply valve (FV5) provides liquid to the second filter in between the second filter outlet valve (FV4) and the second filter (F2) to back-flush the second filter (F2). A filter back-flush discharge valve (FV6) is provided in between the second filter and the second filter inlet valve (FV3) to flush solids that have accumulated during the first mode of normal operation.

A filter inlet pressure sensor (P2) is installed on the pump discharge conduit (304) before the filters (F1, F2). The filter inlet pressure sensor (P2) is configured to output a signal (XP2) to the computer (COMP). A filter discharge pressure sensor (P3) is installed on the pump discharge conduit (304) after the filters (F1, F2). The filter discharge pressure sensor (P2) is configured to output a signal (XP3) to the computer (COMP). Then the pressure drop across the filters (F1, F2) reached a threshold predetermined value, the filters (F1, F2) switch modes of operation from first to second and from second to first.

A first oxygen emitter (EZ1) is installed on the pump discharge conduit (304). In embodiments, the first oxygen emitter (EZ1) is installed on the pump discharge conduit (304) after the filters (F1, F2). The first oxygen emitter (EZ1) is configured to output a signal (XEZ1) to the computer (COMP). The first oxygen emitter (EZ1) oxygenates the water passing through the pump discharge conduit (304).

A liquid flow sensor (F0) is installed on the pump discharge conduit (304) after the filters (F1, F2). The liquid flow sensor (F0) is configured to output a signal (XF0) to the computer (COMP). The liquid flow sensor (F0) measures the flow rate of water passing through the pump discharge conduit (304).

A growing assembly liquid supply valve (V1) is installed on the pump discharge conduit (304). In embodiments, the growing assembly liquid supply valve (V1) is installed on the pump discharge conduit (304) after the filters (F1, F2). The growing assembly liquid supply valve (V1) is equipped with a controller (CV1) that sends a signal (XV1) to or from a computer (COMP).

An electrical conductivity sensor (E2) is installed on the pump discharge conduit (304). In embodiments, the electrical conductivity sensor (E2) is installed on the pump discharge conduit (304) after the filters (F1, F2). The electrical conductivity sensor (E2) is configured to output a signal (XE2) to the computer (COMP). The electrical conductivity sensor (E2) measures the electrical conductivity of the water passing through the pump discharge conduit (304).

A liquid heat exchanger (HX3) is installed on the pump discharge conduit (304). In embodiments, the liquid heat exchanger (HX3) is installed on the pump discharge conduit (304) after the filters (F1, F2). The liquid heat exchanger (HX3) is configured increase or decrease the temperature of the water passing through the pump discharge conduit—(304).

A liquid temperature sensor (T3) is installed on the pump discharge conduit (304). In embodiments, the liquid temperature sensor (T3) is installed on the pump discharge conduit (304) after the filters (F1, F2). In embodiments, the liquid temperature sensor (T3) is installed on the pump discharge conduit (304) after the liquid heat exchanger (HX3). The liquid temperature sensor (T3) is configured to input a signal (XT3) to the computer (COMP).

In embodiments, the growing assembly liquid supply valve (V1), first growing assembly liquid supply valve (V3), and/or the second growing assembly liquid supply valve (V4), may continuously be open to permit a continuous flow of liquid into the growing assemblies (100, 200). In embodiments, the growing assembly liquid supply valve (V1), first growing assembly liquid supply valve (V3), and/or second growing assembly liquid supply valve (V4), may be opened and closed by their controllers (CV1, CV3, CV4) and operated by a computer (COMP). In embodiments, the growing assembly liquid supply valve (V1), first growing assembly liquid supply valve (V3), and/or second growing assembly liquid supply valve (V4), may be opened and closed by their controllers (CV1, CV3, CV4) and operated by a computer (COMP) on a timer.

It is preferred to have the valves (V1, V3, V4) operated in a plurality of modes of operation. In embodiments, a first mode of operation includes having the growing assembly liquid supply valve (V1), first growing assembly liquid supply valve (V3), second growing assembly liquid supply valve (V4), all in an open valve position to transfer liquid from the common reservoir (500) into the growing assemblies (100, 200). In embodiments, a second mode of operation includes having the growing assembly liquid supply valve (V1) open, first growing assembly liquid supply valve (V3) closed, and second growing assembly liquid supply valve (V4) closed, to stop the transfer liquid to the growing assemblies (100, 200). In embodiments, a third mode of operation includes having the growing assembly liquid supply valve (V1) open, first growing assembly liquid supply valve (V3) open, second growing assembly liquid supply valve (V4) closed, to transfer liquid to the first growing assembly (100) and not into the second growing assembly (200). In embodiments, a fourth mode of operation includes having the growing assembly liquid supply valve (V1) open, first growing assembly liquid supply valve (V3) closed, second growing assembly liquid supply valve (V4) open, to transfer liquid to the second growing assembly (200) and not into the first growing assembly (100).

In embodiments, the farming superstructure system (FSS) is operated in a manner that switches from one mode of operation to another mode of operation. In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one of the valves (V1, V3, V4) in a cyclical manner to permit to prevent the roots of the cannabis from receiving too much mist or spray.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100) for 5 seconds followed by not transferring water to the first growing assembly (100) for 600 seconds. In embodiments, water is transferred to the second growing assembly (200) for 5 seconds followed by not transferring water to the second growing assembly (200) for 600 seconds. In embodiments, water is transferred to both the first and second growing assemblies (100, 200) for 5 seconds followed by not transferring water to both the first and second growing assemblies (100, 200) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100) for 60 seconds followed by not transferring water to the first growing assembly (100) for 180 seconds. In embodiments, water is transferred to the second growing assembly (200) for 60 seconds followed by not transferring water to the second growing assembly (200) for 180 seconds. 60 divided by 180 is 0.333.

The duration of time when liquid is transferred to at least one growing assembly (100, 200) divided by the duration of time when liquid is not transferred to at least one growing assembly (100, 200) may be considered an open-close ratio. The open-close ratio may be the duration of time when at least one valve (V1, V3, V4) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1, V3, V4) to periodically introduce the pressurized liquid mixture into to each growing assembly with an open-close ratio ranging from between 0.008 to 0.33, the open-close ratio is defined as the duration of time when the valve (V1, V3, V4) is open in seconds divided by the subsequent duration of time when the same valve is closed in seconds before the same valve opens again. The computer (COMP) opens and closes the valves (V1, V3, V4) to periodically introduce the pressurized liquid mixture into to each growing assembly with an open-close ratio ranging from between 0.008 to 0.33.

In embodiments, the open-close ratio varies. The open-close ratio may vary throughout the life of the cannabis contained within the growing assemblies (100, 200). The open-close ratio may vary throughout the stage of development of the cannabis contained within the growing assemblies (100, 200). Stages of development of the cannabis include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

In embodiments, the temperature is greater during flowering and less during pollination. In embodiments, the temperature is greater during pollination and less during fertilization. In embodiments, the temperature is greater during flowering and less during fertilization. In embodiments, the temperature is less during flowering and greater during pollination. In embodiments, the temperature is less during pollination and greater during fertilization. In embodiments, the temperature is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be added to the common reservoir (500). The carbohydrates are comprised of one or more from the group consisting of sugar, sucrose, molasses, and plant syrups. In embodiments, enzymes may be added to the common reservoir (500). The enzymes are comprised of one or more from the group consisting of amino acids, orotidine 5'-phosphate decarboxylase, OMP decarboxylase, glucanase, beta-glucanase, cellulase, xylanase, Hygrozyme®, Cannazyme®, Microzyme®, and Sensizyme®. In embodiments, vitamins may be added to the common reservoir (500). The vitamins are comprised of one or more from the group consisting of vitamin B, vitamin C, vitamin D, and vitamin E. In embodiments, hormones may be added to the common reservoir (500). The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol. In embodiments, microorganisms may be added to the common reservoir (500). The microorganisms are comprised of one or more from the group consisting of bacteria, diazotroph bacteria, diazotrop archaea, azotobacter vinelandii, clostridium pasteurianu, fungi, arbuscular mycorrhizal fungi, glomus aggrefatum, glomus etunicatum, glomus intraradices, rhizophagus irregularis, and glomus mosseae.

In embodiments, an analyzer (AZ) may be incorporated into the farming superstructure system (FSS). In embodiments, the analyzer analyzes the contents within the common reservoir (500) of analyzes the mixture of water, macro-nutrients, micro-nutrients, and a pH adjustment solution to determine the whether any water, macro-nutrients, micro-nutrients, and a pH adjustment need to be added. A signal (XAZ) from the analyzer may be sent to a computer (COMP). From the signal (XAZ) obtained by the computer (COMP), the computer (COMP) may calculate and automate the introduction of water, macro-nutrients, micro-nutrients, and a pH adjustment solution introduced to the system. In embodiments, the analyzer (AZ) may include a mass spectrometer, fourier transform infrared spectroscopy, infrared spectroscopy, potentiometric pH meter, pH meter, electrical conductivity meter, or liquid chromatography.

FIG. 1B

Figure 1B:
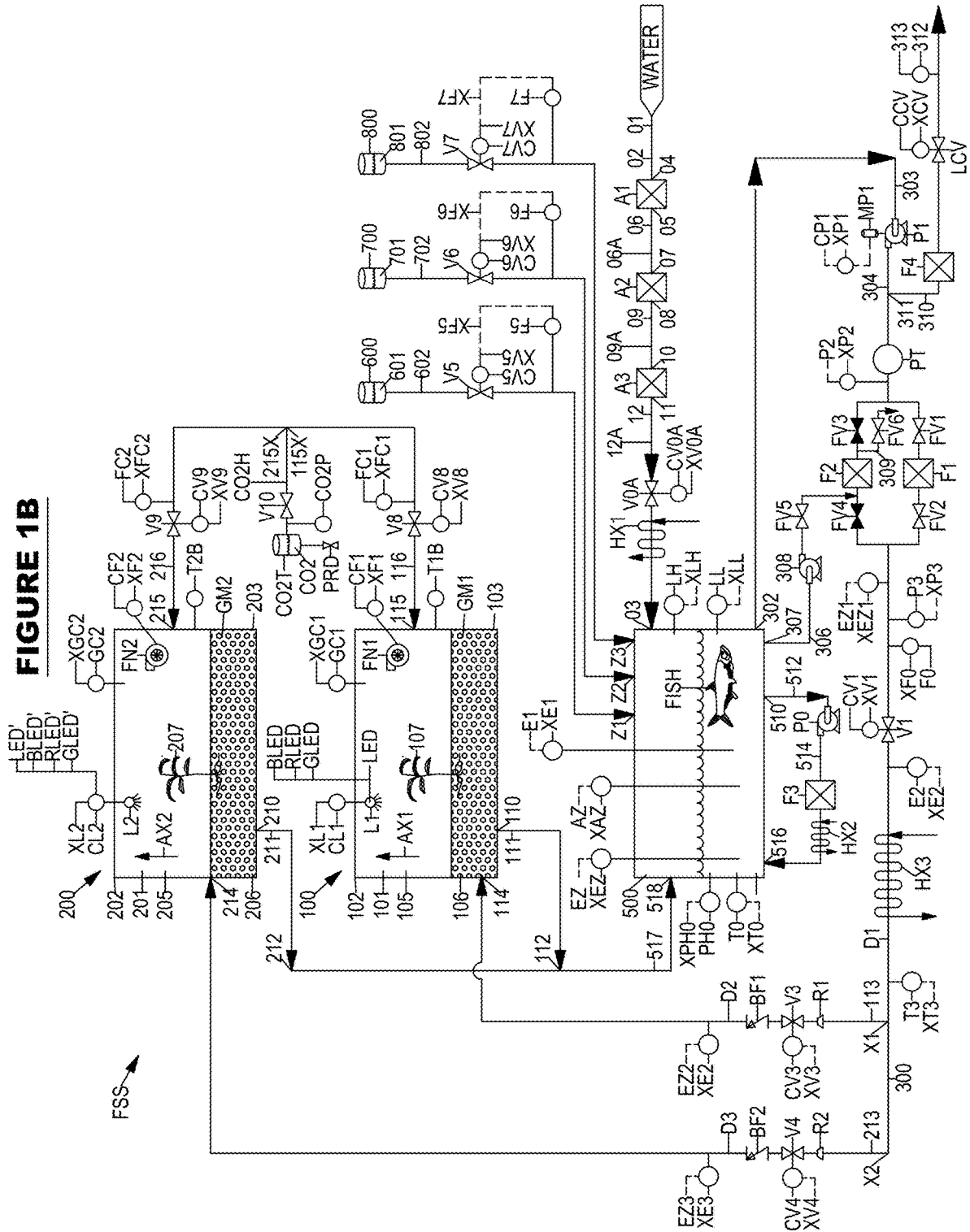
FIG. 1B depicts one non-limiting embodiment of a farming superstructure system (FSS) that includes a first growing assembly (100) having a first growing medium (GM1) and a second growing assembly (200) having a second growing medium (GM2).

FIG. 1B depicts one non-limiting embodiment of a farming superstructure system (FSS) that includes a first growing assembly (100) having a first growing medium (GM1) and a second growing assembly (200) having a second growing medium (GM2).

In embodiments, the first and second growing mediums (GM1, GM2) can be comprised of one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, and quartz. In embodiments, a fungus may be added to the growing medium. In embodiment, the fungus may be mycorrhiza.

FIG. 1B differs from FIG. 1A since a fabric (104, 204) does not partition the growing assembly (100, 200) into an upper-section (105, 205) and a lower-section (106, 206). Instead, the cannabis (107, 207) are in contact with the growing medium (GM1, GM2), and the growing medium (GM1, GM2) partitions each growing assembly (100, 200) into an upper-section (105, 205) and a lower-section (106, 206). Liquid from with pump (P1) is introduced into the interior (101, 201) of each growing assembly (100, 200) via a liquid input (114, 214) where the liquid contacts the growing medium (GM1, GM2). In embodiments, liquid is transferred to the interior (101, 201) of each growing assembly (100, 200) via the liquid input (114, 214) on a periodic basis.

In embodiments, the computer (COMP) controls the lights (L1, L2). In embodiments, the lights (L1, L2) illuminate each growing assembly (100, 200) with an illumination on-off ratio ranging from between 0.5 to 11. The illumination on-off ratio is defined as the duration of time when the lights (L1, L2) are on and illuminate the cannabis (107, 207) in hours divided by the subsequent duration of time when the lights (L1, L2) are off and are not illuminating the cannabis (107, 207) in hours before the lights are turned on again.

In embodiments, the lights (L1, L2) are on and illuminate the cannabis for 18 hours and then are turned off for 6 hours. 18 divided by 6 is 3. In embodiments, an illumination on-off ratio of 3 is contemplated. In embodiments, the lights (L1, L2) are on and illuminate the cannabis for 20 hours and then are turned off for 4 hours. 20 divided by 4 is 5. In embodiments, an illumination on-off ratio of 5 is contemplated. In embodiments, the lights (L1, L2) are on and illuminate the cannabis for 22 hours and then are turned off for 2 hours. 22 divided by 2 is 11. In embodiments, an illumination on-off ratio of 11 is contemplated. In embodiments, the lights (L1, L2) are on and illuminate the cannabis for 8 hours and then are turned off for 16 hours. 8 divided by 16 is 0.5. In embodiments, an illumination on-off ratio of 0.5 is contemplated. In embodiments, the lights (L1, L2) are on and illuminate the cannabis for 12 hours and then are turned off for 12 hours. 12 divided by 12 is 1. In embodiments, an illumination on-off ratio of 1 is contemplated. In embodiments, the is desirable to operate the growing assemblies at an illumination on-off ratio that is greater than 1 and less than 11. In embodiments, the is desirable to operate the growing assemblies at an illumination on-off ratio that is greater than 0.5 and equal to or less than 5.

In embodiments, each growing assembly (100, 200) may include a container that contains a growing medium (GM1, GM2) sufficient to support the roots of the cannabis (107, 207). In embodiments, the growing assembly (100, 200) may be a container that contains a growing medium (GM1, GM2).

FIG. 2

Figure 2:
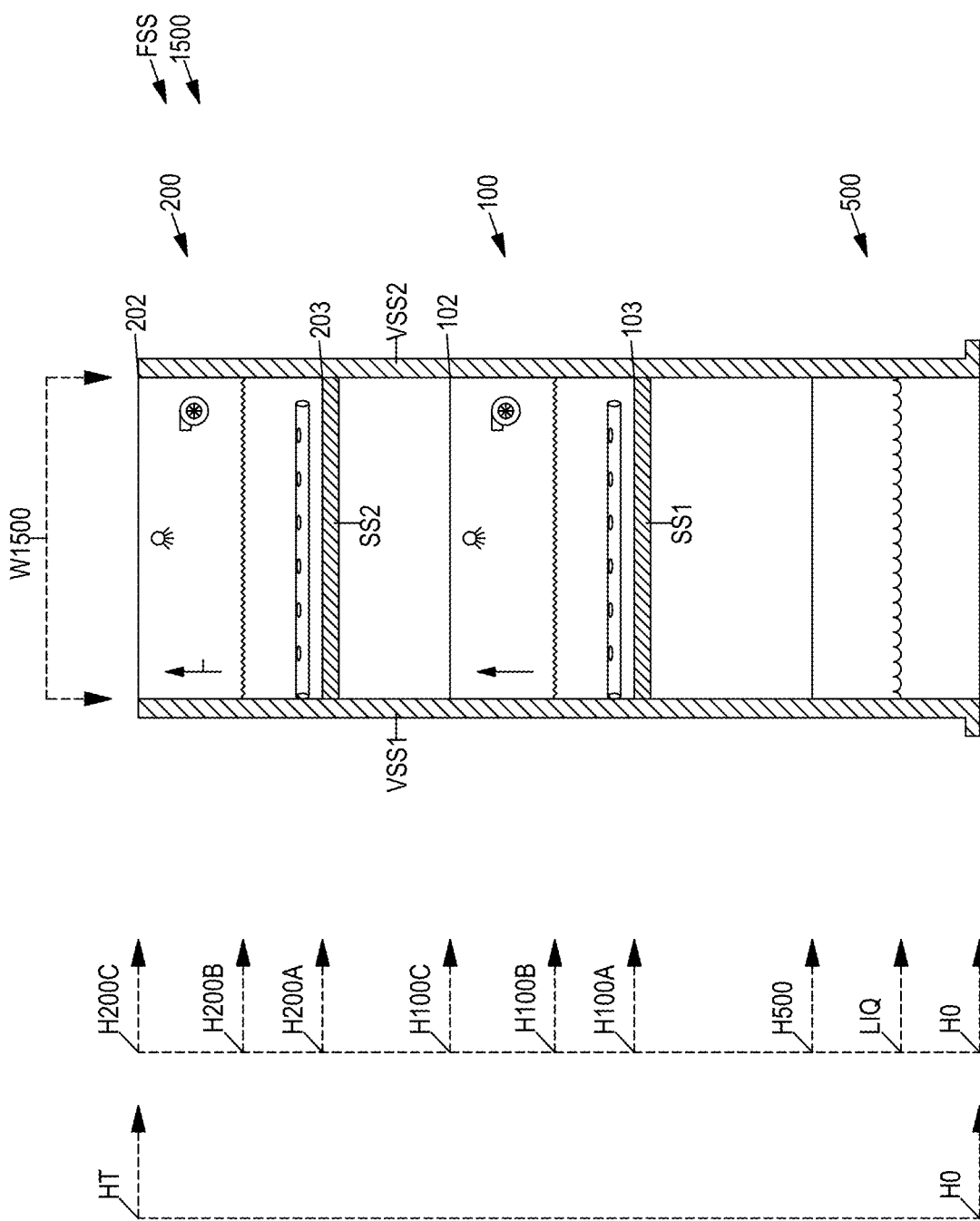
FIG. 2 depicts one non-limiting embodiment of a farming superstructure system (FSS) including a first vertically stacked system (1500) including a plurality of vertically stacked growing assemblies (100, 200) integrated with a first and second vertical support structure (VSS1, VSS2) wherein the first growing assembly (100) is supported by a first horizontal support structure (SS1) and a second growing assembly (200) is supported by a second horizontal support structure (SS2).

FIG. 2 depicts one non-limiting embodiment of a farming superstructure system (FSS) including a first vertically stacked system (1500) including a plurality of vertically stacked growing assemblies (100, 200) integrated with a first and second vertical support structure (VSS1, VSS2) wherein the first growing assembly (100) is supported by a first horizontal support structure (SS1) and a second growing assembly (200) is supported by a second horizontal support structure (SS2).

The first vertically stacked system (1500) shown in FIG. 2 has a base height (H0) located on a floor or support surface. The first vertically stacked system (1500) shown in FIG. 2 has a total height (HT). In embodiments, the total height (HT) may be dictated by the total height of the first and second vertical support structure (VSS1, VSS2). The common reservoir (500) may be positioned on the base height (H0) located on a floor or support surface. The common reservoir (500) has a liquid level (LIQ) that is located below the reservoir height (H500). The reservoir height (H500) is the height of the common reservoir (500).

The bottom (103) of the first growing assembly (100) is located at a first base height (H100A). The first base height (H100A) is the vertical location on the first vertically stacked system (1500) where the first growing assembly (100) is supported by a first horizontal support structure (SS1). The first partition height (H100B) is the vertical location on the first vertically stacked system (1500) of the partition (104) of the first growing assembly (100). The first growing assembly height (H100C) is the vertical location on the first vertically stacked system (1500) where the top (102) of the first growing assembly (100) is located.

The second base height (H200A) is the vertical location on the first vertically stacked system (1500) where the second growing assembly (200) is supported by a second horizontal support structure (SS2). The second partition height (H200B) is the vertical location on the first vertically stacked system (1500) of the partition (204) of the second growing assembly (200). The second growing assembly height (H100C) is the vertical location on the first vertically stacked system (1500) where the top (202) of the second growing assembly (200) is located.

The first vertically stacked system (1500) has a width (W1500). In embodiments, the width (W1500) is greater than the difference between the first growing assembly height (H100C) and the first base height (H100A). In embodiments, the width (W1500) is greater than the difference between the second growing assembly height (H200C) and the second base height (H200A).

FIG. 3

Figure 3:
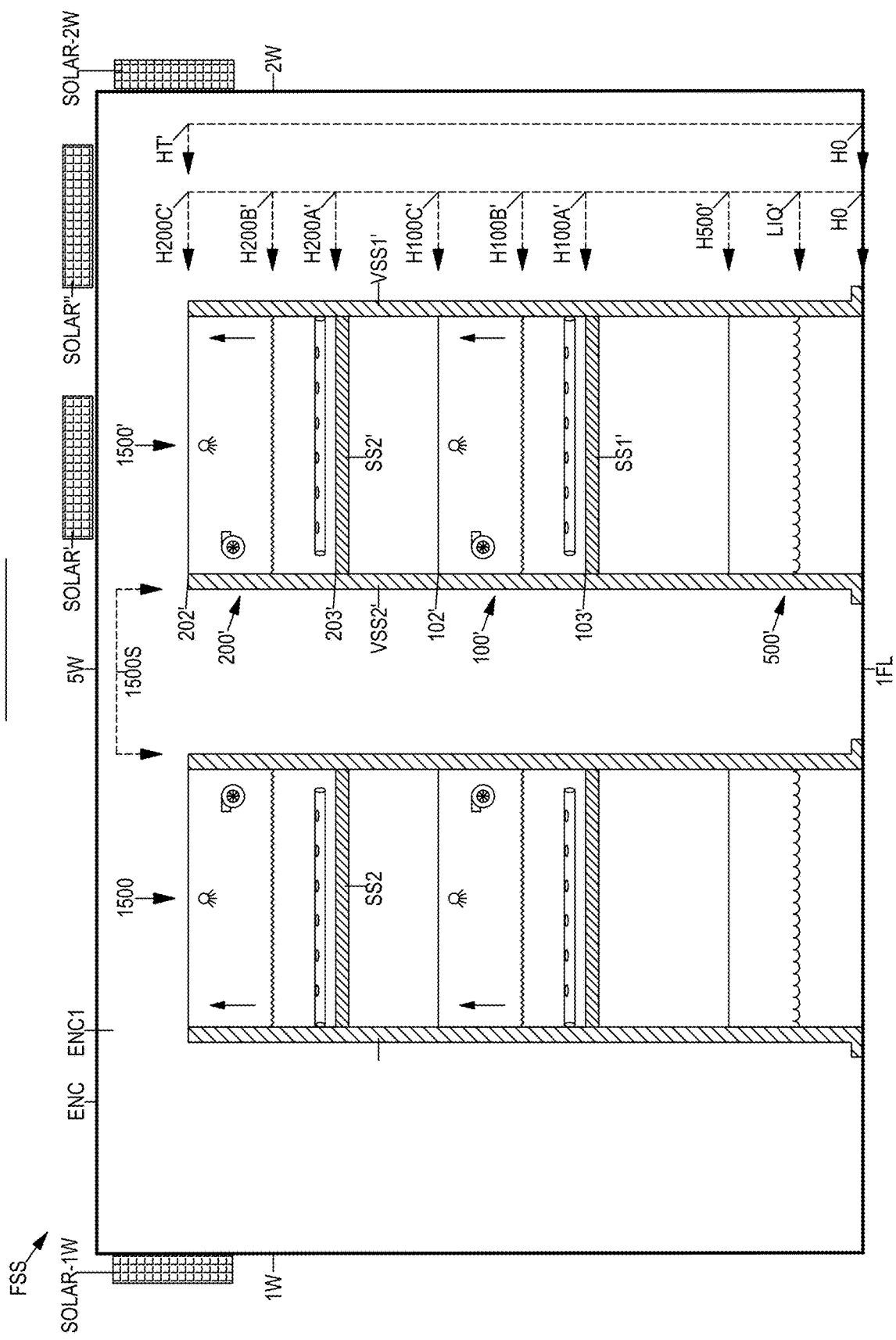
FIG. 3 depicts one non-limiting embodiment of a plurality of vertically stacked systems (1500, 1500') including a first vertically stacked system (1500) and a second vertically stacked system (1500'), the first vertically stacked system (1500) as depicted in FIG. 2, also both vertically stacked systems (1500, 1500') are contained within an enclosure (ENC) having an interior (ENC1).

FIG. 3 depicts one non-limiting embodiment of a plurality of vertically stacked systems (1500, 1500') including a first vertically stacked system (1500) and a second vertically stacked system (1500'), the first vertically stacked system (1500) as depicted in FIG. 2, also both vertically stacked systems (1500, 1500') are contained within an enclosure (ENC) having an interior (ENC1).

The second vertically stacked system (1500') shown in FIG. 3 has a base height (H0) located on a floor or support surface. The second vertically stacked system (1500') shown in FIG. 3 has a total height (HT'). In embodiments, the total height (HT') may be dictated by the total height of the first and second vertical support structure (VSS1', VSS2'). The common reservoir (500') may be positioned on the base height (H0) located on a floor or support surface. The common reservoir (500') has a liquid level (LIQ') that is located below the reservoir height (H500'). The reservoir height (H500') is the height of the common reservoir (500).

The bottom (103') of the first growing assembly (100') is located at a first base height (H100A'). The first base height (H100A') is the vertical location on the second vertically stacked system (1500') where the first growing assembly (100') is supported by a first horizontal support structure (SS1'). The first partition height (H100B') is the vertical location on the second vertically stacked system (1500') of the partition (104') of the first growing assembly (100'). The first growing assembly height (H100C') is the vertical location on the second vertically stacked system (1500') where the top (102') of the first growing assembly (100') is located.

The second base height (H200A') is the vertical location on the second vertically stacked system (1500') where the second growing assembly (200') is supported by a second horizontal support structure (SS2'). The second partition height (H2003) is the vertical location on the second vertically stacked system (1500') of the partition (204') of the second growing assembly (200'). The second growing assembly height (H100C') is the vertical location on the second vertically stacked system (1500') where the top (202') of the second growing assembly (200') is located.

The second vertically stacked system (1500') has a width (W1500'). In embodiments, the width (W1500') is greater than the difference between the first growing assembly height (H100C') and the first base height (H100A'). In embodiments, the width (W1500') is greater than the difference between the second growing assembly height (H200') and the second base height (H200A').

A spacing (1500S) exists between the first vertically stacked system (1500) and the second vertically stacked system (1500'). In embodiments, the spacing (1500S) between the first vertically stacked system (1500) and second vertically stacked system (1500') is less than the width (W1500, W1500) of either of the first vertically stacked system (1500) and second vertically stacked system (1500'). In embodiments, the spacing (1500S) between the first vertically stacked system (1500) and second vertically stacked system (1500') is greater than the width (W1500, W1500) of either of the first vertically stacked system (1500) and second vertically stacked system (1500'). In embodiments, the spacing (1500S) between the first vertically stacked system (1500) and second vertically stacked system (1500') ranges between 3 feet and 12 feet, or 4 feet to 8 feet, or 5 feet to 6 feet.

Figure 4A:
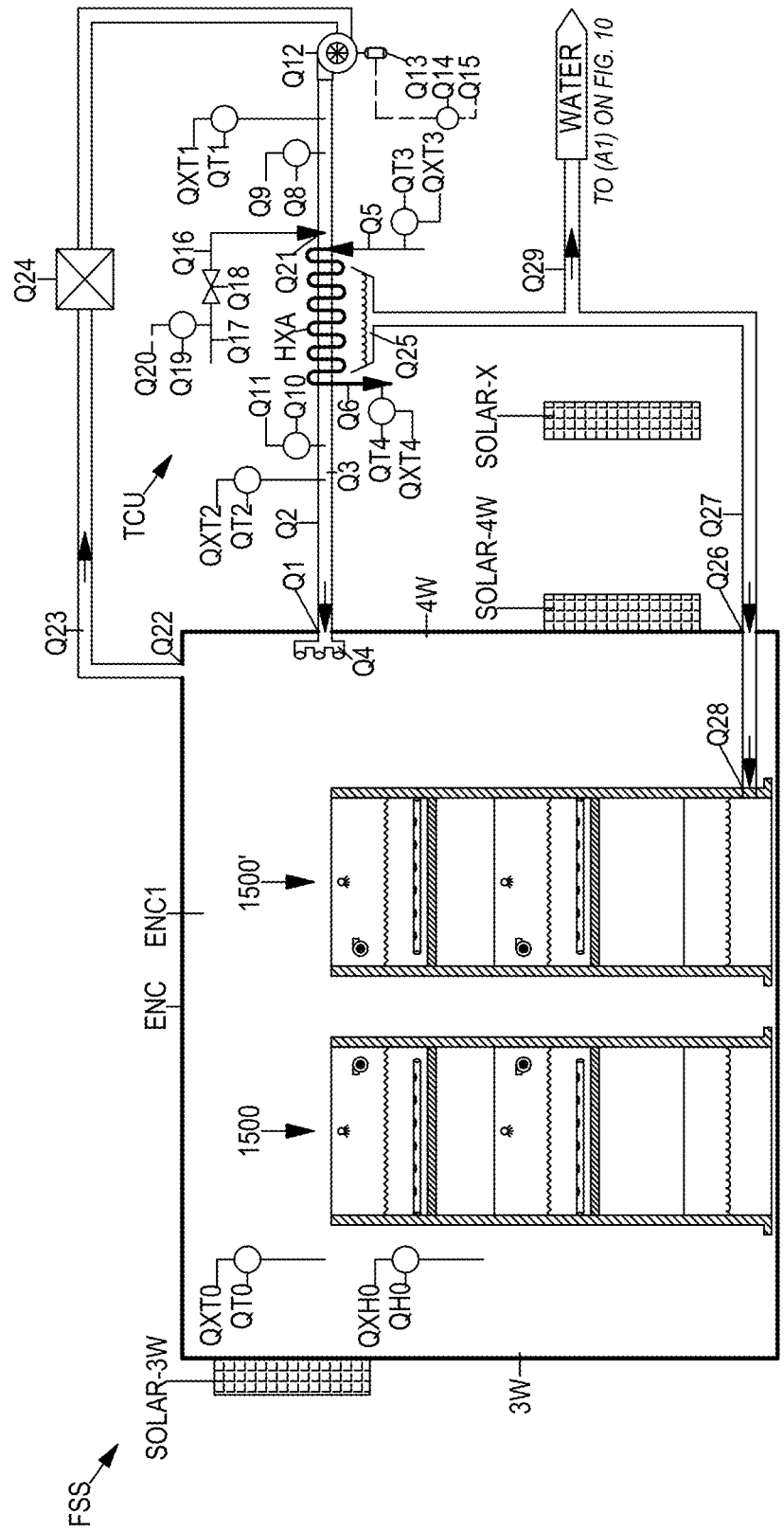
FIG. 4A depicts one non-limiting embodiment of FIG. 3 wherein the enclosure (ENC) is provided with a temperature control unit (TCU) including an air heat exchanger (HXA) that is configured to provide a temperature and/or humidity controlled air supply (Q3) to the interior (ENC1) of the enclosure (ENC) which contains a plurality of vertically stacked systems (1500, 1500').

FIG. 3 shows the first vertically stacked system (1500) and a second vertically stacked system (1500') contained within an enclosure (ENC) having an interior (ENC1). In embodiments, the enclosure may be an area that is sealed off with an artificial or natural barrier. In embodiments, the enclosure may be a building, or a structure with a roof and walls. In embodiments, the enclosure may be a cube container conforming to the International Organization for Standardization (ISO) specifications. FIG. 3 shows the enclosure (ENC) having a first side wall (1W), second side wall (2W), top (5W), and a floor (1FL). For completeness, FIG. 4A shows the enclosure (ENC) of FIG. 3 with a third side wall (3W) and a fourth side wall (4W).

In embodiments, the top (5W), may be comprised of one or more from the group consisting of thatch, overlapping layers, shingles, ceramic tiles, membrane, fabric, plastic, metal, concrete, cement, solar panels, wood, a membrane, tar paper, shale, tile, asphalt, polycarbonate, plastic, cement, and composite materials.

In embodiments, one or more solar panels (SOLAR', SOLAR") may be positioned on top (5W) of the enclosure (ENC) may be used to provide electricity for the farming superstructure system (FSS). In embodiments, one or more solar panels (SOLAR-1W, SOLAR-2W, SOLAR-3W, SOLAR-4W) may be positioned on one or more walls (1W, 2W, 3W, 4W) of the enclosure (ENC) may be used to provide electricity for the farming superstructure system (FSS). In embodiments, one or more solar panels (SOLAR-X) not positioned on the top (5W) one or more walls (1W, 2W, 3W, 4W) of the enclosure (ENC) may be used to provide electricity for the farming superstructure system (FSS).

In embodiments, electricity from at least one of the solar panels (SOLAR', SOLAR", (SOLAR-1W, SOLAR-2W, SOLAR-3W, SOLAR-4W, SOLAR-X) may be used to provide electricity for one or more from the group consisting of: any motor within the farming superstructure system (FSS); any controller within the farming superstructure system (FSS); any conveyor within the farming superstructure system (FSS); a first plurality of lights (L1) in the first growing assembly (100); a first plurality of light emitting diodes (LED) in the first growing assembly (100); a second plurality of lights (L2) in the second growing assembly (200); a second plurality of light emitting diodes (LED') in the second growing assembly (200); blue LEDs (BLED) within the first growing assembly (100); red LEDS (RLED) within the first growing assembly (100); green LEDS (GLED) within the first growing assembly (100); blue LEDs (BLED') within the second growing assembly (200); red LEDS (RLED') within the second growing assembly (200); and green LEDS (GLED') within the second growing assembly (200).

In embodiments, the walls (1W, 2W, 3W, 4W) may be comprised of one or more from the group consisting of metal, concrete, cement, wood, plastic, brick, stone, composite materials, insulation, rockwool, mineral wool, fiberglass, clay, and ceramic. In embodiments, the top (5W) and walls (1W, 2W, 3W, 4W) may form one unitary structure such as a dome, semi-spherical shape, semi-cylindrical, or a greenhouse. In embodiments, the top (5W) and walls (1W, 2W, 3W, 4W) may be clear, translucent, transparent, or clear.

FIG. 4A

FIG. 4A depicts one non-limiting embodiment of FIG. 3 wherein the enclosure (ENC) is provided with a temperature control unit (TCU) including an air heat exchanger (HXA) that is configured to provide a temperature and/or humidity controlled air supply (Q3) to the interior (ENC1) of the enclosure (ENC) which contains a plurality of vertically stacked systems (1500, 1500').

The interior (ENC1) of the enclosure (ENC) has an enclosure temperature sensor (QT0) that is configured to output a signal (QXT0) to a computer (COMP). The interior (ENC1) of the enclosure (ENC) has an enclosure humidity sensor (QH0) that is configured to output a signal (QXH0) to a computer (COMP). An air input (Q1) is configured to permit an air supply (Q3) to be transferred to the interior (ENC1) of the enclosure (ENC) via an air supply entry conduit (Q2). An optional inlet distributor (Q4) may be positioned to be in fluid communication with the air supply entry conduit (Q2) to distribute the air supply (Q3) within the interior (ENC1) of enclosure (ENC). In embodiments, the air heater (HXA) provides a heated air supply (Q3) to the interior (ENC1) of the enclosure (ENC) via said air supply entry conduit (Q2) and said air input (Q1). In embodiments, the air heater (HXA) provides a cooled air supply (Q3) to the interior (ENC1) of the enclosure (ENC) via said air supply entry conduit (Q2) and said air input (Q1).

FIG. 4A shows a temperature control unit (TCU) including an air supply fan (Q12) and air heater (HXA) integrated with the interior (ENC1) of the enclosure (ENC). The air supply fan (Q12) is connected to the interior (ENC1) of the enclosure (ENC) via the air supply entry conduit (Q2). The air supply fan (Q12) is equipped with an air supply fan motor (Q13) and controller (Q14) is configured to input and output a signal (Q15) to the computer (COMP). An air heater (HXA) may be interposed in the air supply entry conduit (Q2) in between the air supply fan (Q12) and the enclosure (ENC). In embodiments, the air heater (HXA) may be interposed in the air supply entry conduit (Q2) in between the enclosure (ENC) and the air supply fan (Q12) and interposed on the air discharge exit conduit (Q23).

Water (Q16) in the form of liquid or vapor may be introduced to the air supply entry conduit (Q2) via a water transfer conduit (Q17). A water input valve (Q18), and a water flow sensor (Q19) may also be installed on the water transfer conduit (Q17). The water flow sensor (Q19) is configured to input a signal (Q20) to the computer (COMP).

The air supply (Q3) may be mixed with the water (Q16) in a water and gas mixing section (Q21) of the air supply entry conduit (Q2). FIG. 4A shows the water and gas mixing section (Q21) upstream of the air heater (HXA) but it may alternately also be placed downstream. The air heater (HXA) may be electric, operated by natural gas, combustion, solar energy, fuel cell, heat pipes, or it may be a heat transfer device that uses a working heat transfer medium, such as steam or any other heat transfer medium known to persons having an ordinary skill in the art to which it pertains.

FIG. 4A shows the air heater (HXA) to have a heat transfer medium input (Q5) and a heat transfer medium output (Q6). In embodiments, heat transfer medium input (Q5) of the air heater (HXA) is equipped with a heat exchanger heat transfer medium inlet temperature (QT3) that is configured to input a signal (QXT3) to the computer (COMP). In embodiments, heat transfer medium output (Q6) of the air heater (HXA) is equipped with a heat exchanger heat transfer medium outlet temperature (QT4) that is configured to input a signal (QXT4) to the computer (COMP).

A first humidity sensor (Q8) is positioned on the discharge of the air supply fan (Q12) upstream of the water and gas mixing section (Q21). The first humidity sensor (Q8) is configured to input a signal (Q9) to the computer (COMP). A heat exchanger inlet gas temperature sensor (QT1) may be positioned on the discharge of the air supply fan (Q12) upstream of the air heater (HXA). The heat exchanger inlet gas temperature sensor (QT1) is configured to input a signal (QXT1) to the computer (COMP).

A second humidity sensor (Q10) is positioned on the discharge of the air heater (HXA) upstream of the air input (Q1) to the interior (ENC1) of the enclosure (ENC). The second humidity sensor (Q10) is configured to input a signal (Q11) to the computer (COMP). A heat exchanger outlet gas temperature sensor (QT2) is positioned on the discharge of the air heater (HXA) upstream of the air input (Q1) to the interior (ENC1) of the enclosure (ENC). The heat exchanger outlet gas temperature sensor (QT2) is configured to input a signal (QXT2) to the computer (COMP).

In embodiments, the air supply fan (Q12), air heater (HXA), and air supply (Q2), permit computer automation while integrated with the heat exchanger inlet gas temperature sensor (QT1), heat exchanger outlet gas temperature sensor (QT2), and enclosure temperature sensor (QT0), to operate under a wide variety of automated temperature operating conditions including varying the temperature range in the interior (ENC1) of the enclosure (ENC) from between 30 degrees to 90 degrees Fahrenheit. In embodiments, the interior (ENC1) of the enclosure (ENC) may be maintained within a temperature ranging from between 65 degrees Fahrenheit to 85 degrees Fahrenheit.

In embodiments, the air supply fan (Q12), air heater (HXA), air supply (Q2), and water (Q17) permit the computer automation while integrated with the first humidity sensor (Q8), second humidity sensor (Q10), and enclosure humidity sensor (QH0), to operate under a wide variety of automated operating humidity conditions including varying the humidity range in the growing assembly (100, 200) from between 5 percent humidity to 100 percent humidity. In embodiments, it is preferred to operate from between 25 percent humidity to 75 percent humidity. In embodiments, it is preferred to operate from between 40 percent humidity to 60 percent humidity. In embodiments, it is preferred to operate from between 44 percent humidity to 46 percent humidity.

In embodiments, the air supply fan (Q12) accepts an air supply (Q3) from the interior (ENC1) of the enclosure (ENC) via an air discharge exit conduit (Q23). The air discharge exit conduit (Q23) is connected at one end to the enclosure (ENC) via an air output (Q22) and at another end to the air supply fan (Q12). An air filter (Q24) may be installed on the air discharge exit conduit (Q23) in between the enclosure (ENC) and the air supply fan (Q12) to remove particles prior to entering the air supply fan (Q12) for recycle back to the enclosure (ENC). In embodiments, the air filter (Q24) filters out particulates from the interior (ENC1) of the enclosure (ENC) and the air supply fan (Q12) recycles the filtered air back to the interior (ENC1) of the enclosure (ENC). The filtered air may be cooled or heated prior to being recycled to the interior (ENC1) of the enclosure (ENC).

Figure 4B:
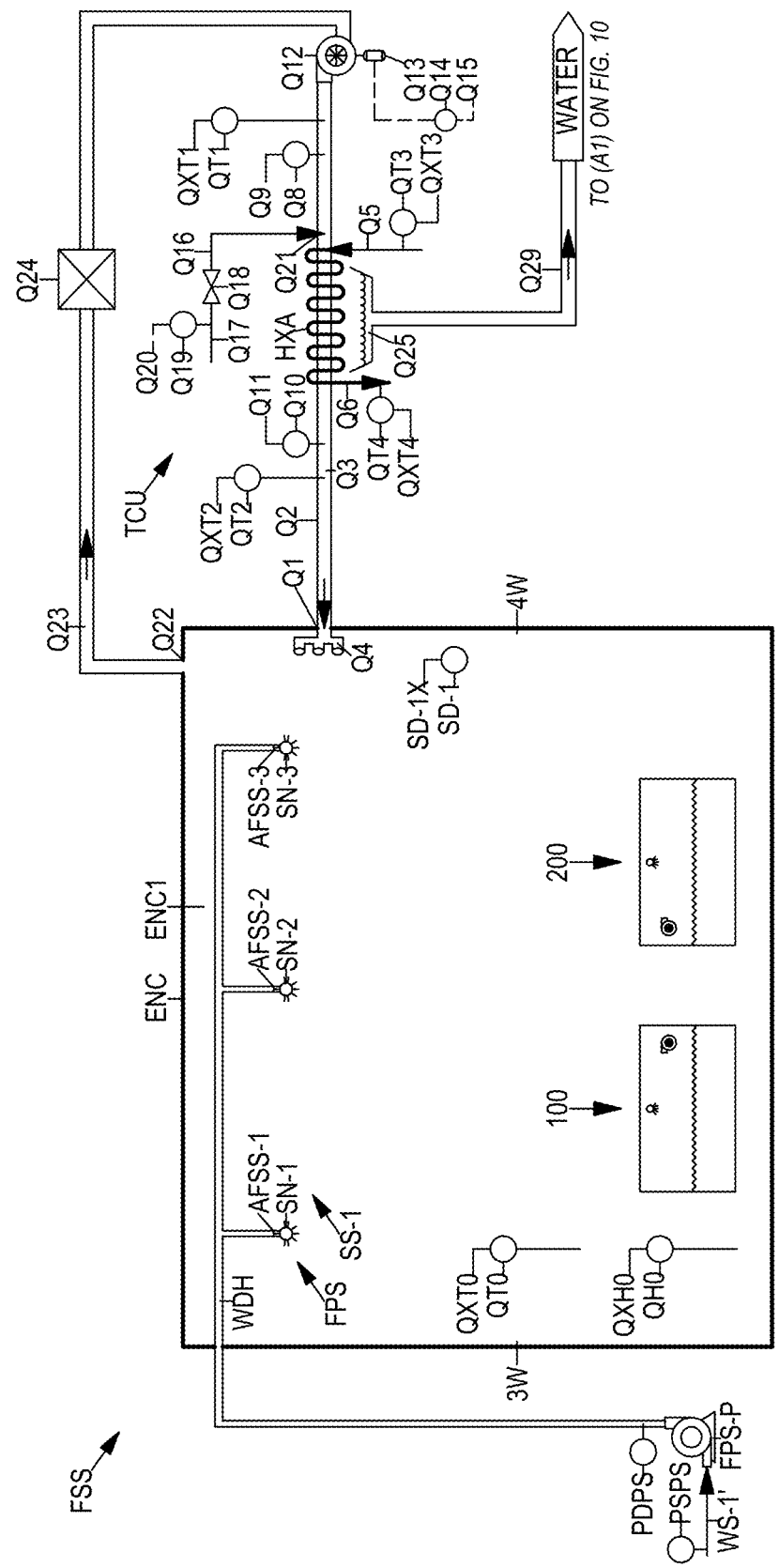
FIG. 4B depicts one non-limiting embodiment of FIG. 1B and FIG. 4A wherein the enclosure (ENC) is provided with a temperature control unit (TCU) including an air heat exchanger (HXA) that is configured to provide a temperature and/or humidity controlled air supply (Q3) to the interior (ENC1) of the enclosure (ENC) which contains a plurality of growing assemblies (100, 200).
Figure 5A:
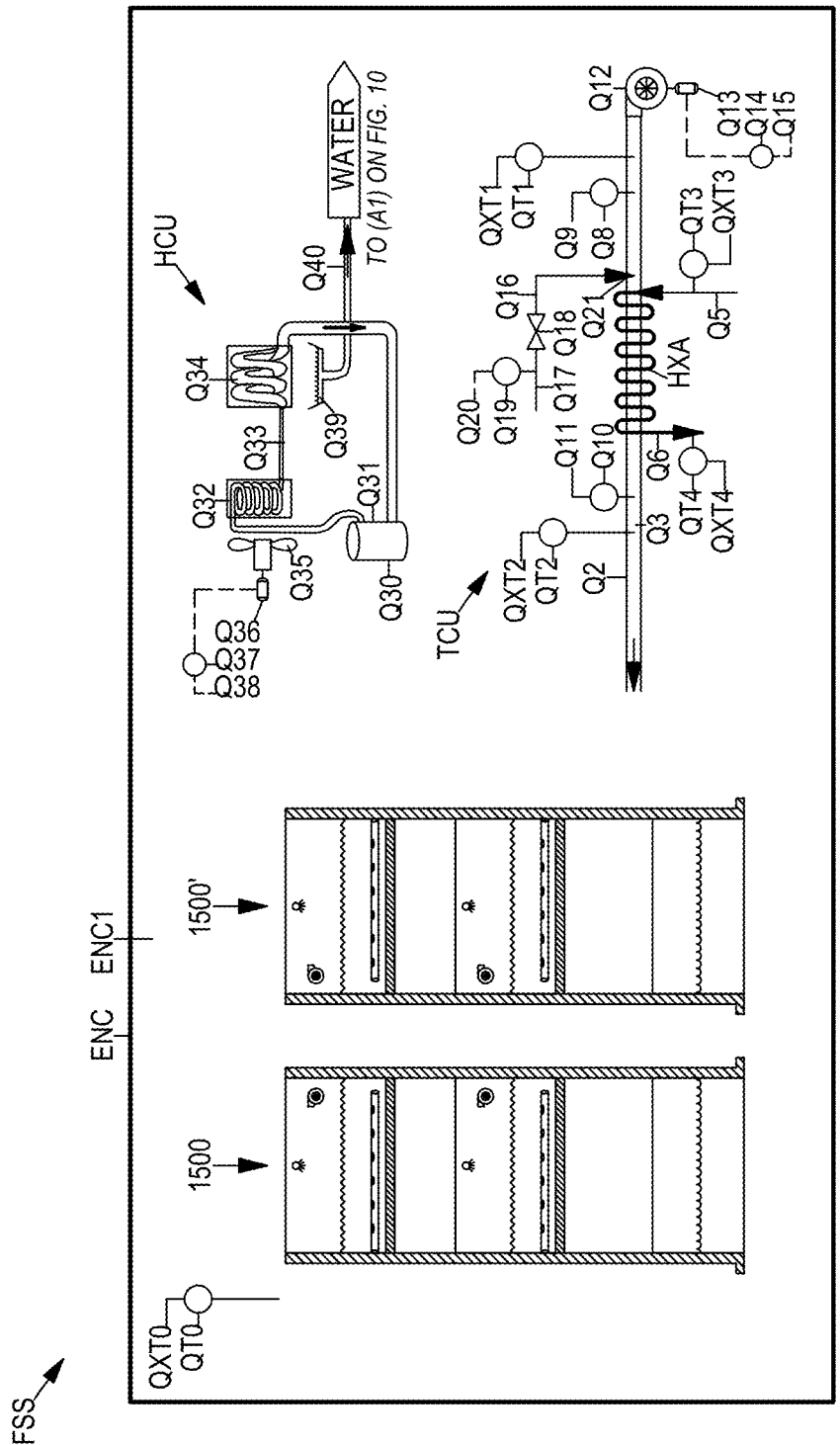
FIG. 5A depicts one non-limiting embodiment of FIG. 4A wherein the temperature control unit (TCU) of FIG. 4A is contained within the interior (ENC1) of the enclosure (ENC) and coupled with a humidity control unit (HCU).
Figure 10:
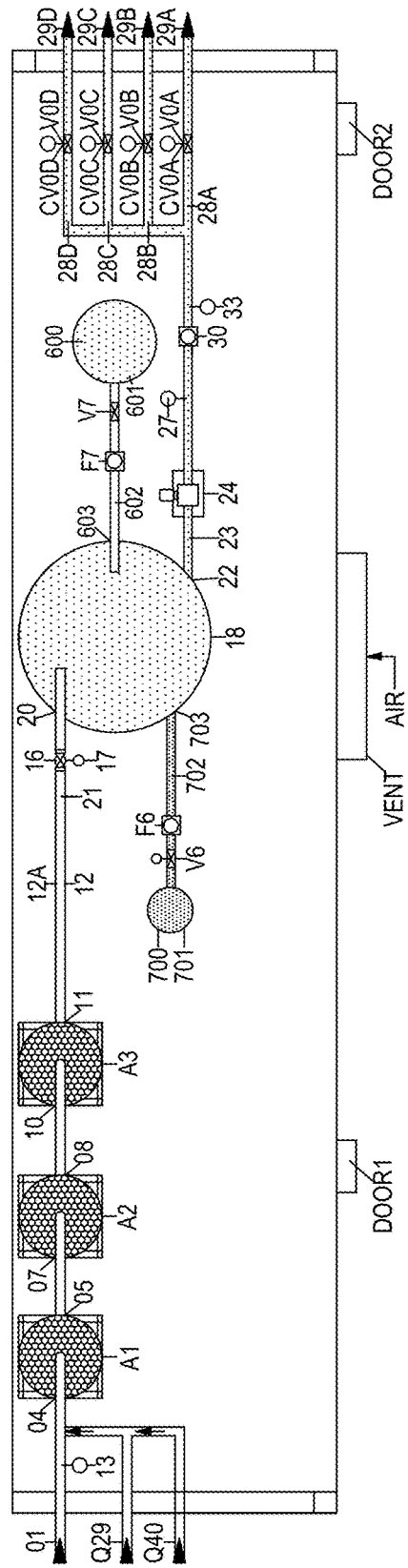
FIG. 10 shows a top view of one embodiment of a liquid distribution module (LDM) provided inside of a cube container conforming to the International Organization for Standardization (ISO) specifications and that is configured to provide a source of liquid to a plurality of plant growing modules (PGM).

In embodiments, the air heater (HXA) adds heat to the interior (ENC1) of the enclosure (ENC). In embodiments, the air heater (HXA) removes heat from the interior (ENC1) of the enclosure (ENC) and as a result may condense water from the air supply (Q3) provided from the from the interior (ENC1) of the enclosure (ENC). In embodiments, where the air heater (HXA) removes heat from the interior (ENC1) of the enclosure (ENC) water is collected in the form of condensate (Q25). In embodiments, the condensate (Q25) may in turn be provided to the enclosure (ENC) via an enclosure condensate input (Q26) and a condensate conduit (Q27). The condensate (Q25) provided to the enclosure (ENC) via an enclosure condensate input (Q26) may be provided to at least one common reservoir (500, 500') via a common tank condensate input (Q28). In embodiments, the condensate (Q25) may contain undesirable compounds (especially viruses and bacteria) and in turn may be provided to the input to the first water treatment unit (A1) as shown in FIG. 10 as a first undesirable compounds-laden condensate (Q29).
FIG. 4B FIG. 4B depicts one non-limiting embodiment of FIG. 1B and FIG. 4A wherein the enclosure (ENC) is provided with a temperature control unit (TCU) including an air heat exchanger (HXA) that is configured to provide a temperature and/or humidity controlled air supply (Q3) to the interior (ENC1) of the enclosure (ENC) which contains a plurality of growing assemblies (100, 200).
FIG. 5A FIG. 5A depicts one non-limiting embodiment of FIG. 4A wherein the temperature control unit (TCU) of FIG. 4A is contained within the interior (ENC1) of the enclosure (ENC) and coupled with a humidity control unit (HCU), FIG. 5A shows the temperature control unit (TCU) of FIG. 4A but contained within the interior (ENC1) of the enclosure (ENC). FIG. 5A also shows a non-limiting embodiment of a humidity control unit (HCU) positioned within the interior (ENC1) of the enclosure (ENC). A portion of the humidity control unit (HCU) may be positioned exterior to the enclosure (ENC) and not positioned within the interior (ENC1).

In embodiments, the humidity control unit (HCU) may include a compressor (Q30), a condenser (Q32), a metering device (Q33), an evaporator (Q34), and a fan (Q35). The fan (Q35) may be equipped with a motor (Q36) and a controller (Q37) that is configured to input or output a signal (Q38) to a computer (COMP).

The compressor (Q31) is connected to the condenser (Q32), the condenser (Q32) is connected to the metering device (Q33), the metering device (Q33) is connected to an evaporator (Q34), and the evaporator (Q34) is connected to the compressor (Q31) to form a closed-loop refrigeration circuit configured to contain a refrigerant (Q31). The metering device (Q33) includes one or more from the group consisting of a restriction, orifice, valve, tube, capillary, and capillary tube. The refrigerant (Q31) is conveyed from the compressor to the condenser, from the condenser to the evaporator through the metering device, and from the evaporator to the compressor. The evaporator (Q34) is positioned within the interior (ENC1) of the enclosure (ENC) and is configured to evaporate refrigerant (Q31) within the evaporator (Q34) by removing heat from the interior (ENC1) of the enclosure (ENC). In embodiments, the evaporator (Q34) is contained within the interior (ENC1) of the enclosure (ENC). In embodiments, the condenser (Q32) is not contained within the interior (ENC1) of the enclosure (ENC). The fan (Q35) is configured to blow air from within the interior (ENC1) of the enclosure (ENC) over at least a portion of the humidity control unit (HCU).

The humidity control unit (HCU) is configured to selectively operate the system in a plurality of modes of operation, the modes of operation including at least:

(1) a first mode of operation in which compression of a refrigerant (Q31) takes place within the compressor (Q30), and the refrigerant (Q31) leaves the compressor (Q30) as a superheated vapor at a temperature above the condensing point of the refrigerant (Q31);

(2) a second mode of operation in which condensation of refrigerant (Q31) takes place within the condenser (Q32), heat is rejected and the refrigerant (Q31) condenses from a superheated vapor into a liquid, and the liquid is cooled to a temperature below the boiling temperature of the refrigerant (Q31); and (3) a third mode of operation in which evaporation of the refrigerant (Q31) takes place, and the liquid phase refrigerant (Q31) boils in evaporator (Q34) to form a vapor or a superheated vapor while absorbing heat from the interior (ENC1) of the enclosure (ENC).

Figure 5B:
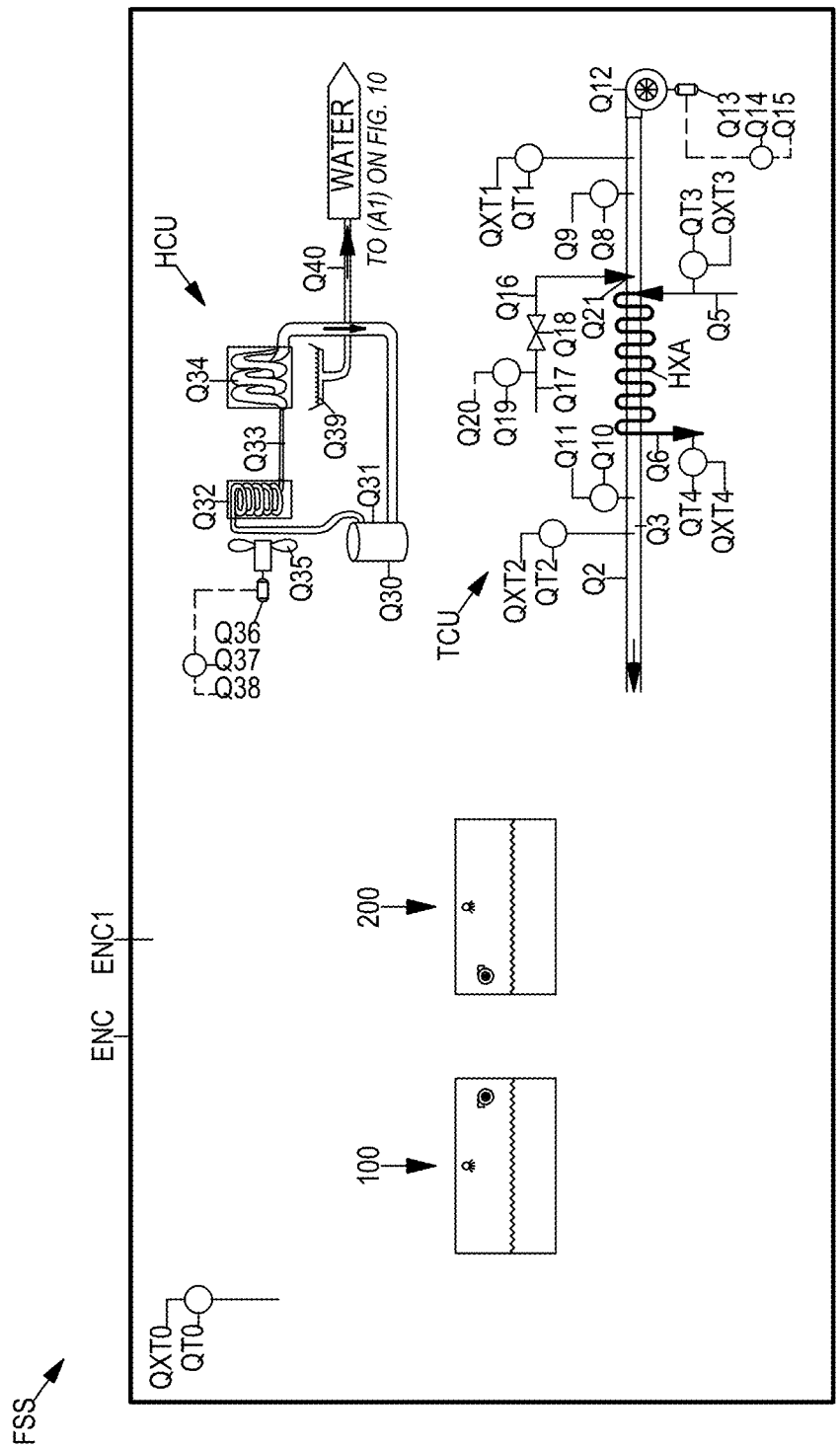
FIG. 5B depicts one non-limiting embodiment of FIG. 4B and FIG. 5A wherein the temperature control unit (TCU) of FIG. 4B is contained within the interior (ENC1) of the enclosure (ENC) and coupled with a humidity control unit (HCU).

The evaporator (Q34) is configured to evaporate the refrigerant (Q31) to absorb heat from the interior (ENC1) of an enclosure (ENC). As a result, the evaporator (Q34) may condense water from the interior (ENC1) of the enclosure (ENC). In embodiments, the evaporator (Q34) condenses water vapor from the interior (ENC1) of an enclosure (ENC) and forms condensate (Q39). In embodiments, the condensate (Q39) may contain undesirable compounds (especially viruses and bacteria) and in turn may be provided to the input to the first water treatment unit (A1) as shown in FIG. 10 as a second undesirable compounds-laden condensate (Q40).
FIG. 5B FIG. 5B depicts one non-limiting embodiment of FIG. 4B and FIG. 5A wherein the temperature control unit (TCU) of FIG. 4B is contained within the interior (ENC1) of the enclosure (ENC) and coupled with a humidity control unit (HCU).
FIG. 6

FIG. 6 shows a front view of one embodiment of a plant growing module (PGM) provided inside of a cube container conforming to the International Organization for Standardization (ISO) specifications.

FIG. 6 shows a portion of the farming superstructure system (FSS) including a front view of one embodiment of a plant growing module (PGM) provided inside of a cube container conforming to the International Organization for Standardization (ISO) specifications.

The front view shows four growing assemblies (100, 100', 200, 200') including two first growing assemblies (100, 100') and two second growing assembly (200, 200') contained within an interior (ENC1) of an enclosure (ENC). FIG. 6 shows the two first growing assemblies (100, 100') and two second growing assembly (200, 200') each equipped with drain ports (110, 110') and drain conduits (111, 111') for draining liquid from each growing assembly (100, 100', 200, 200') into a common reservoir (500) via a common drain conduit (517) and drain input (518).

FIG. 6 shows one pump (P1) pulling liquid from one common reservoir (500) and transferring a pressurized liquid through a filter (F1A) into a plurality of liquid supply headers (300, 300') which are in turn then provided to a plurality of first liquid supply conduits (113, 113') and a plurality of second liquid supply conduit (213, 213'). Four liquid supply conduits (113, 113', 213, 213') are provided from two liquid supply headers (300, 300') which is provided with pressurized water through one filter (F1A) by one pump (P1) pulling liquid from one common reservoir (500).

Figure 9:
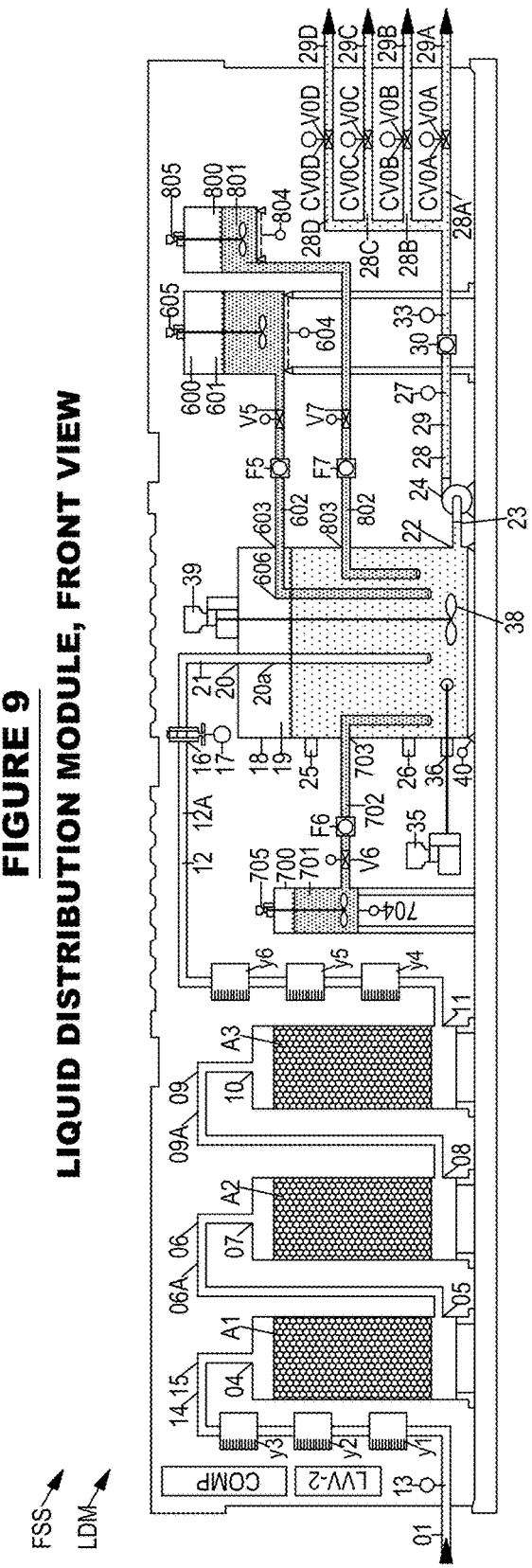
FIG. 9 shows a front view of one embodiment of a liquid distribution module (LDM) provided inside of a cube container conforming to the International Organization for Standardization (ISO) specifications and that is configured to provide a source of liquid to a plurality of plant growing modules (PGM).

The common reservoir (500) of FIG. 6 is provided with a pressurized liquid (29) through a pressurized liquid transfer conduit (28) that enters the common reservoir (500) via a first water inlet (03). FIGS. 9 and 10 describe a liquid distribution module (LDM) that provides the pressurized liquid (29) and transfers it to the plant growing module (PGM) via a pressurized liquid transfer conduit (28).

As depicted in FIG. 6 and FIG. 7, one common reservoir (500) is provided for a first vertically stacked system (1500) and a second vertically stacked system (1500') that contain a total of two first growing assemblies (100, 100') and two second growing assembly (200, 200').

The enclosure (ENC) of FIG. 6 is shown to have a first side wall (1W), second side wall (2W), top (5W), and A floor (1FL). For completeness, the top view of the enclosure (ENC) of FIG. 6 is shown in FIG. 7 and is shown to have a first side wall (1W), second side wall (2W), third side wall (3W), and fourth side wall (4W).

FIG. 7

FIG. 7 shows a top view of one embodiment of a plant growing module (PGM) provided inside of a cube container conforming to the International Organization for Standardization (ISO) specifications.

The enclosure (ENC) of FIG. 7 is shown to have a low voltage shut-off switch (LVV-1), a humidity control unit (HCU) (as described in FIG. 5), and a temperature control unit (TCU) (as described in FIGS. 4A&B). FIG. 7 also shows the first vertically stacked system (1500) and second vertically stacked system (1500') with one common reservoir (500). FIG. 7 also shows a third vertically stacked system (1500") and a fourth vertically stacked system (1500''') each equipped with their own source of pressurized liquid (29C, 29D) provided by a plurality of pressurized liquid transfer conduits (28C, 28D) as described in detail in FIGS. 9 and 10.

FIG. 8

FIG. 8 shows a first side view of one embodiment of a plant growing module (PGM). The enclosure (ENC) of FIG. 8 is shown to have a humidity control unit (HCU) (as described in FIG. 5), and a temperature control unit (TCU) (as described in FIGS. 4A&B). FIG. 8 shows a first vertically stacked system (1500) on the left-hand-side and a second vertically stacked system (1500') on the right-hand-side.

The first vertically stacked system (1500) is shown to have a second growing assembly (200) located above a first growing assembly (100). The second growing assembly (200) has a drain port (210) and a drain conduit (211) that directly drains into a common reservoir (500) located below both growing assemblies (100, 200). The drain conduit (211) from the second growing assembly (200) is secured to the second vertical support structure (VSS2) via a support connection (211X). In embodiments, the drain conduit (211) from the second growing assembly (200) may be secured to the first vertical support structure (VSS1), or alternately to the first horizontal support structure (SS1), or second horizontal support structure (SS2)

The first growing assembly (100) has a drain port (110) and a drain conduit (111) that directly drains into a common reservoir (500) located below both growing assemblies (100, 200). The drain conduit (111) from the first growing assembly (200) is secured to the second vertical support structure (VSS2) via a support connection (111X). In embodiments, the drain conduit (111) from the first growing assembly (100) may be secured to the first vertical support structure (VSS1), or alternately to the first horizontal support structure (SS1).

The second vertically stacked system (1500') is shown to have a second growing assembly (200') located above a first growing assembly (100'). The second growing assembly (200') is configured to receive liquid from the pump (P1) via a second liquid supply conduit (213') and a liquid input (214'). The second liquid supply conduit (213') for the second growing assembly (200') is secured to the second vertical support structure (VSS2') via a support connection (213X'). In embodiments, the second liquid supply conduit (213') for the second growing assembly (200') may be secured to the first vertical support structure (VSS1'), or alternately to the first horizontal support structure (SS1'), or second horizontal support structure (SS2').

The first growing assembly (100') is configured to receive liquid from the pump (P1) via a first liquid supply conduit (113') and a liquid input (114'). The first liquid supply conduit (113') for the first growing assembly (100') is secured to the second vertical support structure (VSS2') via a support connection (113X'). In embodiments, the first liquid supply conduit (113') for the first growing assembly (100') may be secured to the first vertical support structure (VSS1'), or alternately to the first horizontal support structure (SS1'). The spacing (1500S) between the vertically stacked systems (1500, 1500') in FIG. 8 ranges from 3 feet to 5 feet.

FIG. 9

FIG. 9 shows a front view of one embodiment of a liquid distribution module (LDM) provided inside of a cube container conforming to the International Organization for Standardization (ISO) specifications and that is configured to provide a source of liquid to a plurality of plant growing modules (PGM).

FIG. 9 shows one non-limiting embodiment of a liquid distribution module (LDM) to provide a source of liquid to a plurality of plant growing modules (PGM). The liquid distribution module (LDM) of FIGS. 9 and 10 include a first water treatment unit (A1), a second water treatment unit (A2), and a third water treatment unit (A3), that provide a third contaminant depleted water (12) to the interior (19) of a solution tank (18).

The solution tank (18) mixes a water supply (01) with macro-nutrients (601), micro-nutrients (701), and/or a pH adjustment solution (801) to form a mixed solution prior to pumping the mixed solution to at least one common reservoir (500) of at least one plant growing modules (PGM). FIG. 9 depicts the first water treatment unit (A1) to include a cation, a second water treatment unit (A2) to include an anion, and a third water treatment unit (A3) to include a membrane.

A first water pressure sensor (13) is positioned on the water input conduit (14) that is introduced to the first input (04) to the first water treatment unit (A1). In embodiments, a filter (y1), activated carbon (y2), and adsorbent (y3), are positioned on the water input conduit (14) prior to introducing the water supply (01) to the first water treatment unit (A1). The water supply (01) may be considered a contaminant-laden water (15) that includes positively charged ions, negatively charged ions, and undesirable compounds. A first contaminant depleted water (06) is discharged by the first water treatment unit (A1) by a first output (05). The first contaminant depleted water (06) may be a positively charged ion depleted water (06A). The first contaminant depleted water (06) is then transferred to the second water treatment unit (A2) via a second input (07). A second contaminant depleted water (09) is discharged by the second water treatment unit (A2) by a second output (08). The second contaminant depleted water (09) may be a negatively charged ion depleted water (09A). The second contaminant depleted water (09) is then transferred to the third water treatment unit (A3) via a third input (10). A third contaminant depleted water (12) is discharged by the third water treatment unit (A3) by a third output (11). The third contaminant depleted water (12) may be an undesirable compounds depleted water (12A). The third contaminant depleted water (12) is then transferred to the interior (19) of a solution tank (18) via a water supply conduit (21) and water input (20).

Within the interior (19) of the solution tank (18), the third contaminant depleted water (12) may be mixed with macro-nutrients (601) from a macro-nutrient supply tank (600), micro-nutrients (701) from a micro-nutrient supply tank (700), and/or a pH adjustment solution (801) from a micro-nutrient supply tank (700). In embodiments, a cation (y4), an anion (y5), and a polishing unit (y6), are positioned on the water supply conduit (21) in between the third water treatment unit (A3) and the water input (20) of the solution tank (18). The polishing unit (y6) may be any type of conceivable device to improve the water quality such as an ultraviolet unit, ozone unit, microwave unit, or the like.

In embodiments, water supply valve (16) is positioned on the water supply conduit (21) in between the third water treatment unit (A3) and the water input (20) of the solution tank (18). The water supply valve (16) is equipped with a controller (17) that inputs or outputs a signal from a computer (COMP). In embodiments, the solution tank (18) is equipped with a high-level sensor (25) and a low-level sensor (26). The high-level sensor (25) is used for detecting a high level and the low-level sensor (26) is used for detecting a low level. The high-level sensor (25) is configured to output a signal to the computer (COMP) when the high-level sensor (25) is triggered by a high level of liquid within the solution tank (18). The low-level sensor (26) is configured to output a signal to the computer (COMP) when the low-level sensor (26) is triggered by a low level of liquid within the solution tank (18). In embodiments, when the low-level sensor (26) sends a signal to the computer (COMP), the water supply valve (16) on the water supply conduit (21) is opened and introduces water into the solution tank (18) until the high-level sensor (25) is triggered thus sending a signal to the computer (COMP) to close the water supply valve (16). This level control loop including the high-level sensor (25) for detecting a high level and a low-level sensor (26) for detecting a lower level may be coupled to the operation of the water supply valve (16) for introducing a water supply (01) through a first water treatment unit (A1), a second water treatment unit (A2), and a third water treatment unit (A3), to provide a third contaminant depleted water (12) to the interior (19) of a solution tank (18). The liquid distribution module (LDM) is equipped with a low voltage shut-off switch (LVV-2).

The interior (19) of the solution tank (18) is equipped with an oxygen emitter (35) for oxygenating the water within. The oxygen emitter (35) is connected to the interior (19) of the solution tank (18) via an oxygen emitter connection (36) which protrudes the solution tank (18). The solution tank (18) may be placed on a load cell (40) for measuring the mass of the tank. The solution tank (18) may be equipped with a mixer (38) for mixing water with macro-nutrients (601), micro-nutrients (701), and/or a pH adjustment solution (801). The mixer (38) may be of an auger or blade type that is equipped with a motor (39).

The solution tank (18) has a water output (22) that is connected to a water discharge conduit (23). The water discharge conduit (23) is connected at one end to the water output (22) of the solution tank (18) and at another end to a water supply pump (24). The water supply pump (24) provides a source of pressurized liquid (29) via a pressurized liquid transfer conduit (28).

A second water pressure sensor (27) is positioned on the pressurized liquid transfer conduit (28). A flow sensor (30) and a water quality sensor (33) may be positioned on the pressurized liquid transfer conduit (28). The water quality sensor (33) can measure electrical conductivity or resistivity. The pressurized liquid transfer conduit (28) can be split into a plurality of streams for providing to a plurality of plant growing modules (PGM) having a plurality of common reservoirs (500, 500', 500", 500''').

The pressurized liquid transfer conduit (28) can be split into a plurality of streams including a first pressurized liquid transfer conduit (28A) for sending to a common tank (500) for the first vertically stacked system (1500) and second vertically stacked system (1500') of FIG. 6, a second pressurized liquid transfer conduit (28B) as a back-up water source to the common tank (500) of FIG. 6, a third pressurized liquid transfer conduit (28C) for the common tank (500") for the third vertically stacked system (1500") of FIG. 6, and a fourth pressurized liquid transfer conduit (28D) for the common tank (500''') for the fourth vertically stacked system (1500''') of FIG. 6.

FIG. 10

FIG. 10 shows a top view of one embodiment of a liquid distribution module (LDM) provided inside of a cube container conforming to the International Organization for Standardization (ISO) specifications and that is configured to provide a source of liquid to a plurality of plant growing modules (PGM).

FIG. 11

Figure 11:
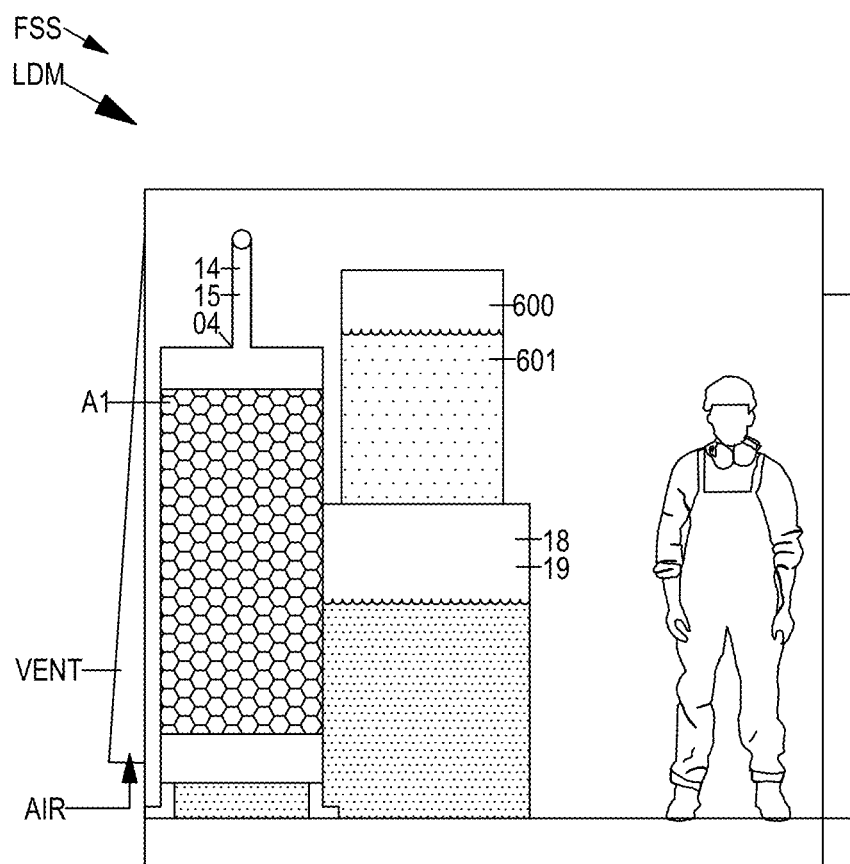
FIG. 11 shows a first side view of one embodiment of a liquid distribution module (LDM).

FIG. 11 shows a first side view of one embodiment of a liquid distribution module (LDM).

FIG. 12

FIG. 12 shows one non-limiting embodiment of a fabric (104) used in a growing assembly (100), the fabric (104)

having a multi-point temperature sensor (MPT100) connected thereto for measuring temperatures at various lengths along the sensor's length.

FIGS. 12 and 13 disclose a fabric (104) that includes a multi-point temperature sensor (MPT100). The fabric (104) may be used in each of the growing assemblies (100, 200). The fabric has a width (104W) and a length (104L). The multi-point temperature sensor (MPT100) is connected to the fabric (104) and is configured to measure the temperature of the fabric (104) along several points along the width (104W).

FIG. 12 shows the multi-point temperature sensor (MPT100) having 8 temperature sensor elements to measure the temperature across a first distance (104W1), second distance (104W2), third distance (104W), fourth distance (104W4), fifth distance (104W5), sixth distance (104W6), seventh distance (104W7), and eighth distance (104W8). In embodiments, each of the 8 temperature sensor elements is configured to input a signal to the computer (COMP). The temperature element at the first distance (104W1) sends a first signal (XMPT1) to a computer (COMP). The temperature element at the second distance (104W2) sends a second signal (XMPT2) to a computer (COMP). The temperature element at the third distance (104W) sends a third signal (XMPT3) to a computer (COMP). The temperature element at the fourth distance (104W4) sends a fourth signal (XMPT4) to a computer (COMP). The temperature element at the fifth distance (104W5) sends a fifth signal (XMPT5) to a computer (COMP). The temperature element at the sixth distance (104W6) sends a sixth signal (XMPT6) to a computer (COMP). The temperature element at the seventh distance (104W7) sends a seventh signal (XMPT7) to a computer (COMP). The temperature element at the eighth distance (104W8) sends an eighth signal (XMPT8) to a computer (COMP). An average temperature of the fabric (104) may be obtained by averaging at least two of the signals from the multi-point temperature sensor (MPT100).

Each of the distances (104W1, 104W2, 104W3, 104W4, 104W5, 104W6, 104W7, 104W8) is measured relative to the base width (104W0) of the fabric (104). In embodiments, the fabric (104) is comprised of one or more from the group consisting of plastic, polyethylene, high-density polyethylene (HDPE), low-density polyethylene (LDPE), polyethylene terephthalate (PET), polyacrylonitrile, and polypropylene.

In embodiments, the fabric (104) is configured to have a wicking height constant characterized by a wicking height range from 0.4 inches to 1.9 inches. The wicking height constant is a measurement of an ability of the fabric (104) to absorb moisture. In embodiments, the fabric (104) is configured to have an absorbance constant characterized by an absorbance range from 0.001 lb/in2 to 0.005 lb/in 2. In embodiments, the absorbance constant is a measurement of moisture the fabric retains. In embodiments, the moisture that the fabric (104) retains may be provided by a liquid, mist, spray, water, mixture of water with macro-nutrients, micro-nutrients, pH adjustment solution, carbohydrates, enzymes, vitamins, hormones.

FIG. 13

FIG. 13 shows another one non-limiting embodiment of a fabric (104) used in a growing assembly (100).

FIG. 14

Figure 14:
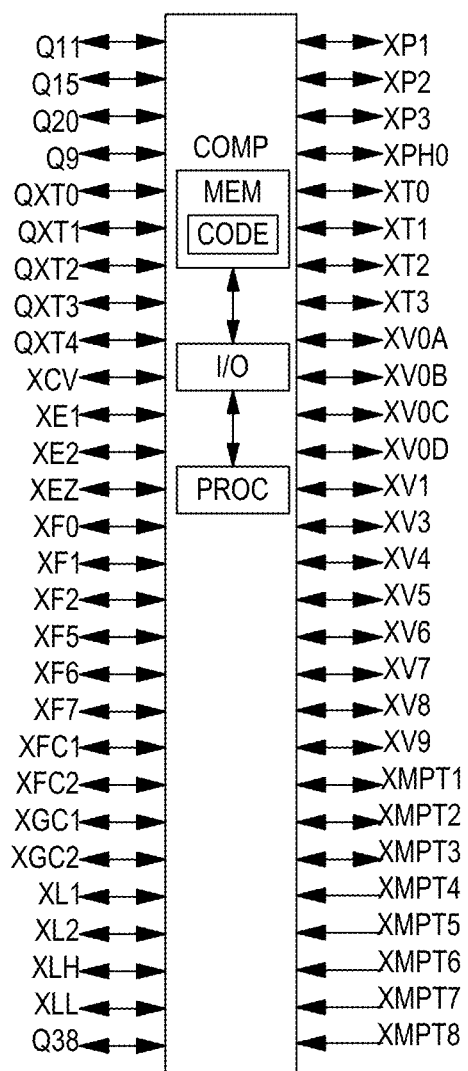
FIG. 14 depicts a computer (COMP) that is configured to input and output signals listed in FIGS. 1-13.

FIG. 14 depicts a computer (COMP) that is configured to input and output signals listed in FIGS. 1-13.

FIG. 15

Figure 15:
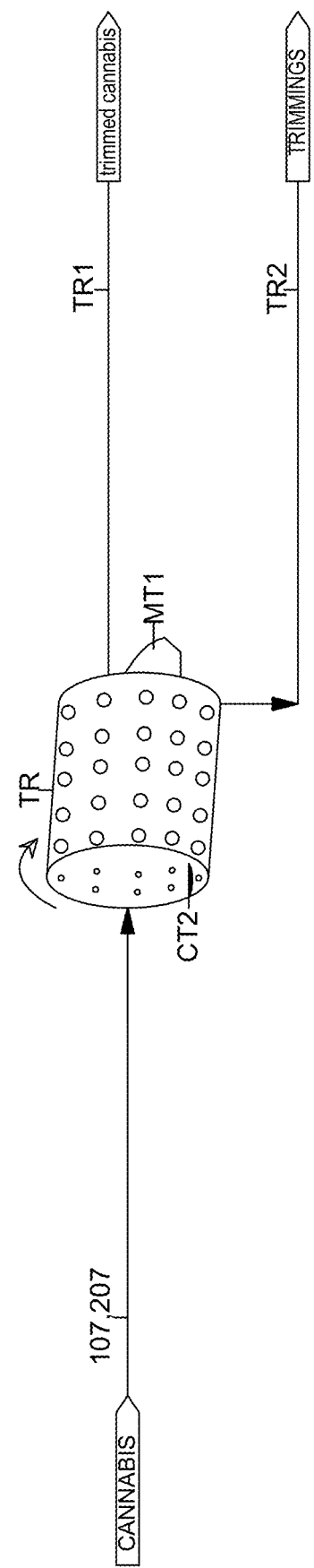
FIG. 15 shows a trimmer (TR) that is configured to trim at least a portion of Grass Weedly Junior (107, 207) that was growing in each growing assembly (100, 200).

FIG. 15 shows a trimmer (TR) that is configured to trim at least a portion of the cannabis (107, 207) that was growing in each growing assembly (100, 200).

Once the cannabis (107, 207) is harvested from each growing assembly (100, 200), the cannabis (107, 207) may be trimmed by use of a trimmer (TR). In embodiments, trimming the cannabis (107, 207) is necessary to obtain a final product for medicinal or recreational use. Trimming the cannabis (107, 207) may be done for several reasons including improving appearance, taste, and tetrahydrocannabinol (THC) concentration.

Cannabis (107, 207) consists of the leaves, seeds, stems, roots, or any reproductive structures. In embodiments, the reproductive structures may be flower. In embodiments, a flower may be a reproductive structure. In embodiments, the reproductive structures may be buds. In embodiments, a bud may be a reproductive structure. In embodiments, trimming removes at least a portion of the leaves and stems from the reproductive structures. In embodiments, cannabis (107, 207) is harvested from each growing assembly (100, 200) by severing the plants with a cutting tool. In embodiments, the roots of the cannabis (107, 207) are not introduced to the trimmer (TR). In embodiments, cannabis (107, 207) comprising leaves, seeds, stems, and reproductive structures (buds) are introduced to the trimmer (TR). In embodiments, cannabis (107, 207) comprising leaves, seeds, stems, roots, and reproductive structures (buds) are introduced to the trimmer (TR).

In embodiments, the trimmer (TR) separates the leaves and/or stems from the buds. In embodiments, the trimmer (TR) separates the buds from the leaves and stems. In embodiments, the trimmer (TR) separates the buds from the leaves and stems by applying using a rotational motion provided by a motor (MT1). In embodiments, the trimmer (TR) imparts a rotational motion upon the cannabis (107, 207). In embodiments, the trimmer (TR) moves the cannabis (107, 207) from one location to the another. In embodiments, a rotational motion cannabis (107, 207) passes the cannabis (107, 207) across a blade (CT2), the blade is configured to separate the leaves or stems from the buds, to provide trimmed cannabis that is depleted of leaves or stems. In embodiments, the trimmer (TR) moves the cannabis (107, 207) across a blade (CT2), the blade is configured to separate the leaves or stems from the buds, to provide trimmed cannabis that is depleted of leaves or stems.

FIG. 15 displays the trimmer (TR) accepting a source of cannabis (107, 207) and trims leaves and/or stems from the reproductive structures (buds) to produce trimmed cannabis (TR1) and trimmings (TR2).

FIG. 16

Figure 16:
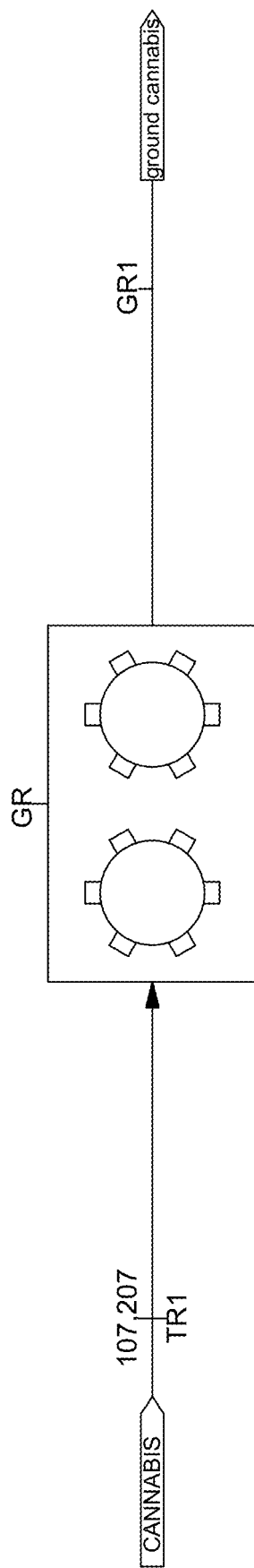
FIG. 16 shows a grinder (GR) that is configured to grind at least a portion of Grass Weedly Junior (107, 207) that was growing in each growing assembly (100, 200).

FIG. 16 shows a grinder (TR) that is configured to grind at least a portion of the cannabis (107, 207) that was growing in each growing assembly (100, 200). FIG. 16 also shows a grinder (TR) that is configured to grind at least a portion of the trimmed cannabis (TR1) that was trimmed by the trimmer (TR) as shown in FIG. 15.

A grinder (GR) generates a ground cannabis (GR1). The grinder may be used to grind (i) a portion of the cannabis (107, 207) harvested from each growing assembly (100, 200) or (ii) a portion of the trimmed cannabis (TR1) that is trimmed by the trimmer (TR) to produce ground cannabis (GR1). In embodiments, grinding of the cannabis is required for creating food products including a multifunctional composition.

FIG. 17

Figure 17:
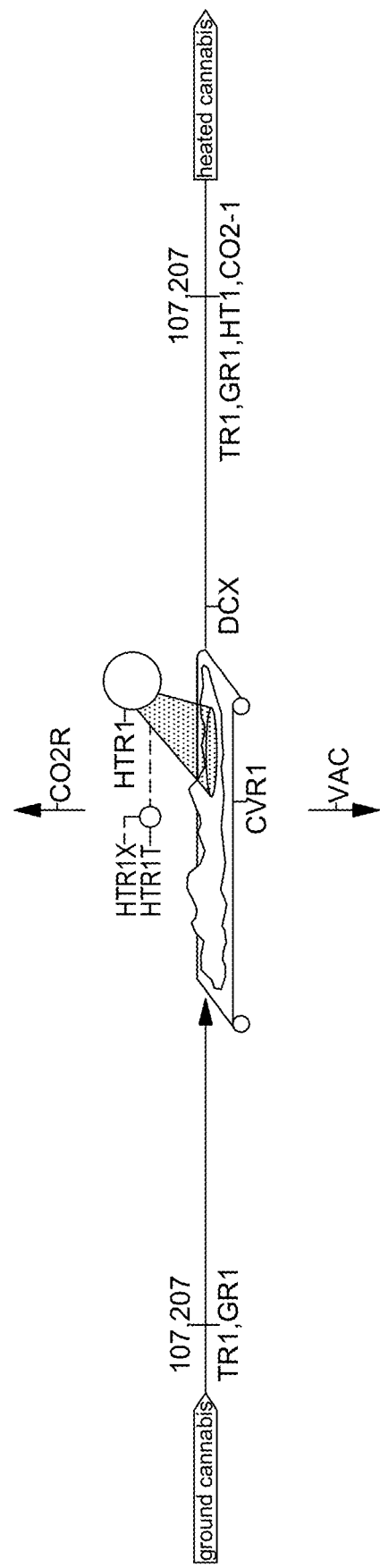
FIG. 17 shows a heater (HTR1) that is configured to heat at least a portion of Grass Weedly Junior (107, 207) that was growing in each growing assembly (100, 200).

FIG. 17 shows a heater (HTR1) that is configured to heat at least a portion of Grass Weedly Junior (107, 207) that was growing in each growing assembly (100, 200). In embodiments, heating the cannabis is required for creating food products including a multifunctional composition.

FIG. 17 shows a heating unit (HTR1) that is configured to heat at least a portion of Grass Weedly Junior (107, 207) that was growing in each growing assembly (100, 200). FIG. 17 shows a heater (HTR1) that is configured to heat at least a portion of the cannabis (107, 207) that was growing in each growing assembly (100, 200). FIG. 17 also shows a heater (HTR1) that is configured to heat at least a portion of the trimmed cannabis (TR1) that was trimmed by the trimmer (TR) as shown in FIG. 15. FIG. 17 also shows a heater (HTR1) that is configured to heat at least a portion of the ground cannabis (GR1) that was ground by the grinder (GR) as shown in FIG. 16. The heater (HTR1) may be used to heat (i) a portion of the cannabis (107, 207) harvested from each growing assembly (100, 200), (ii) a portion of the trimmed cannabis (TR1) that is trimmed by the trimmer (TR), or (ii) a portion of the ground cannabis (GR1) that is ground by the cannabis (GR1).

The heater (HTR1) generates a heated cannabis (HT1). The heater (HTR1) is configured to heat the cannabis (107, 207). In embodiments, the heater (HTR1) is configured to heat the cannabis (107, 207) as the cannabis (107, 207) passes through the heater (HTR1) via a conveyor (CVR1).

In embodiments, heating the cannabis (107, 207) removes carbon dioxide (CO2R) from the cannabis (107, 207) to form a carbon dioxide depleted cannabis (CO2-1). In embodiments, the carbon dioxide depleted cannabis (CO2-1) is synonymous with the heated cannabis (HT1).

In embodiments, heating the cannabis (107, 207) decarboxylates the cannabis (107, 207) to produce a decarboxylated cannabis (DCX). In embodiments, heating the cannabis (107, 207) decarboxylates the tetrahydrocannabinolic acid (THCA) within the cannabis (107, 207) to form active tetrahydrocannabinol. In embodiments, decarboxylation is a chemical reaction that removes a carboxyl group and releases carbon dioxide (CO2R). In embodiments, heating the cannabis (107, 207) removes carbon dioxide form the cannabis (107, 207) to form a carbon dioxide depleted cannabis (CO2-1).

The heater (HTR1) is equipped with a heater temperature sensor (HTR1T) that sends a signal (HTR1X) to the computer (COMP). In embodiments, the heater (HTR1) is operated within a temperature ranging from 185 degrees F. to 280 degrees F. In embodiments, the heater (HTR1) is operated within a temperature ranging from 205 degrees F. to 250 degrees F. In embodiments, the heater (HTR1) produces a heated cannabis (HT1) that has a temperature ranging from 185 degrees F. to 280 degrees F. In embodiments, the heater (HTR1) produces a heated cannabis (HT1) that has a temperature ranging from 205 degrees F. to 250 degrees F.

In embodiments, a vacuum (VAC) is pulled on cannabis (107, 207) while the heater (HTR1) is heating the cannabis (107, 207) to aide in carbon dioxide removal. In embodiments, a vacuum (VAC) is pulled on the cannabis (107, 207) while the heater (HTR1) is heating the cannabis (107, 207) to a pressure that ranges from 0.5 inches of water to 30 inches of water. In embodiments, a vacuum (VAC) is pulled on the cannabis (107, 207) while the heater (HTR1) is heating the cannabis (107, 207) to a pressure that ranges from 5 inches of water to 90 inches of water. In embodiments, a vacuum (VAC) is pulled on the cannabis (107, 207) while the heater (HTR1) is heating the cannabis (107, 207) to a pressure that ranges from 2 pounds per square inch absolute to 14.69 pounds per square inch absolute. In embodiments, the cannabis (107, 207) is heated by the heater (HTR1) for a duration of 45 minutes to 2 hours. In embodiments, the cannabis (107, 207) is heated by the heater (HTR1) for a duration of 1 hour to 3 hours. In embodiments, the cannabis (107, 207) is heated by the heater (HTR1) for a duration of 2 hour to 24 hours.

FIG. 17A

Figure 17A:
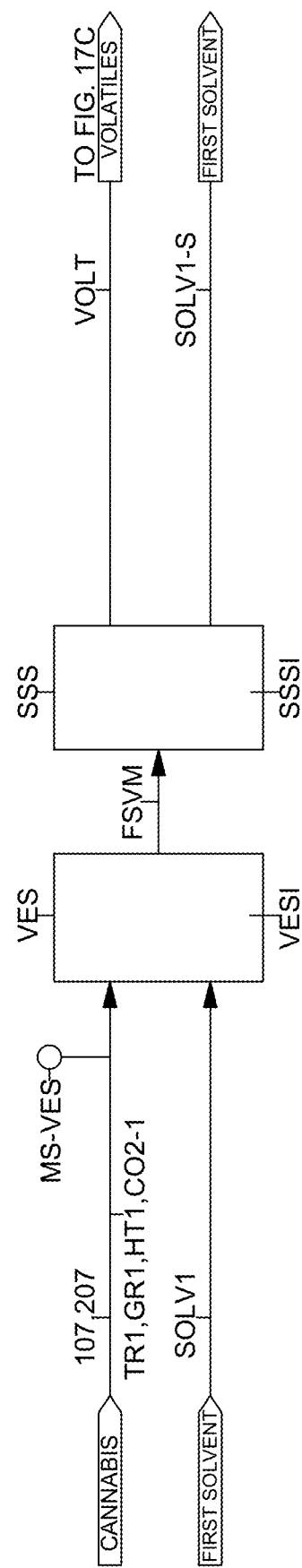
FIG. 17A shows one non-limiting embodiment of a volatiles extraction system (VES) that is configured to extract volatiles from cannabis (107, 207) with a first solvent (SOLV1).

FIG. 17A shows one non-limiting embodiment of a volatiles extraction system (VES) that is configured to extract volatiles from cannabis (107, 207) with a first solvent (SOLV1). The volatiles extraction system (VES) is configured to separate volatiles (VOLT) from cannabis (107, 207). The volatiles extraction system (VES) is configured to accept cannabis (107, 207), or heated cannabis (HT1), ground cannabis (GR1), trimmed cannabis (TR1), or combinations thereof. In embodiments, the cannabis (107, 207), heated cannabis (HT1), ground cannabis (GR1), and/or trimmed cannabis (TR1) may be weighed with a mass sensor (MS-VES) prior to being introduced to the volatiles extraction system (VES).

The volatiles (VOLT) include one or more from the group consisting of oil, wax, terpenes. The terpenes include one or more from the group consisting of limonene, humulene, pinene, linalool, caryophyllene, mycrene, eucalyptol, nerolidol, bisablol, and phytol. In embodiments, the terpenes include at least one organic carbon containing chemical compound. In embodiments, the terpenes include one or more from the group consisting of limonene, humulene, pinene, linalool, caryophyllene, mycrene, eucalyptol, nerolidol, bisablol, and phytol. In embodiments, limonene includes 1-Methyl-4-(1-methylethenyl)-cyclohexene. In embodiments, humulene includes 2,6,6,9-Tetramethyl-1,4-8-cycloundecatriene. In embodiments, pinene includes (1S, 5S)-2,6,6-trimethylbicyclo[3.1.1]hept-2-ene. In embodiments, linalool includes 3,7-Dimethylocta-1,6-dien-3-ol. In embodiments, caryophyllene includes (1R,4E,9S)-4,11,11-Trimethyl-8-methylidenebicyclo[7.2.0]undec-4-ene. In embodiments, mycrene includes 7-Methyl-3-methylene-1,6-octadiene. In embodiments, eucalyptol includes 1,3,3-Trimethyl-2-oxabicyclo[2,2,2]octane. In embodiments, nerolidol includes 3,7,11-Trimethyl-1,6,10-dodecatrien-3-ol. In embodiments, bisablol includes 6-methyl-2-(4-methylcyclohex-3-en-1-yl)hept-5-en-2-ol. In embodiments, phytol includes (2E,7R,11R)-3,7,11,15-tetramethyl-2-hexadecen-1-ol.

The volatiles extraction system (VES) extracts volatiles (VOLT) from cannabis with use of a first solvent (SOLV1). The first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, and vapor.

The volatiles extraction system (VES) has an interior (VESI) that is configured to mix cannabis (107, 207), heated cannabis (HT1), ground cannabis (GR1), and/or trimmed cannabis (TR1) with a first solvent (SOLV1). The volatiles extraction system (VES) is configured to accept a first solvent (SOLV1). The first solvent (SOLV1) is configured to contact the cannabis (107, 207), heated cannabis (HT1), ground cannabis (GR1), and/or trimmed cannabis (TR1) within the interior (VEST) of the volatiles extraction system (VES).

An output of the volatiles extraction system (VES) is a first solvent and volatiles mixture (FSVM). The first solvent and volatiles mixture (FSVM) is at least a mixture of volatiles (VOLT) and the first solvent (SOLV1). In embodiments, the first solvent and volatiles mixture (FSVM) is a mixture of oil, wax, terpenes and first solvent (SOLV1). In embodiments, the first solvent and volatiles mixture (FSVM) is a mixture of oil, wax, and first solvent (SOLV1). In embodiments, the first solvent and volatiles mixture (FSVM) is a mixture of oil and first solvent (SOLV1). The first solvent and volatiles mixture (FSVM) is transferred from the volatiles extraction system (VES) to the first solvent separation system (SSS).

The first solvent separation system (SSS) is configured to separate the volatiles (VOLT) from the first solvent and volatiles mixture (FSVM). The first solvent separation system (SSS) has an interior (SSSI). The first solvent and volatiles mixture (FSVM) is transferred from the interior (VESI) of the volatiles extraction system (VES) to the interior (SSSI) of the first solvent separation system (SSS).

In embodiments, the pressure within the interior (VESI) of the volatiles extraction system (VES) is greater than the pressure within the interior (SSSI) of the first solvent separation system (SSS). In embodiments, the pressure within the interior (VESI) of the volatiles extraction system (VES) is less than the pressure within the interior (SSSI) of the first solvent separation system (SSS). In embodiments, the pressure within the interior (VEST) of the volatiles extraction system (VES) is equal to the pressure within the interior (SSSI) of the first solvent separation system (SSS).

The first solvent separation system (SSS) outputs a volatiles (VOLT) and a separated first solvent (SOLV1-S). The volatiles (VOLT) may be then mixed with a second solvent (SOLV2) as described in FIG. 17C. The volatiles (VOLT) may alternately by mixed with insects which include one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

Figure 17B:
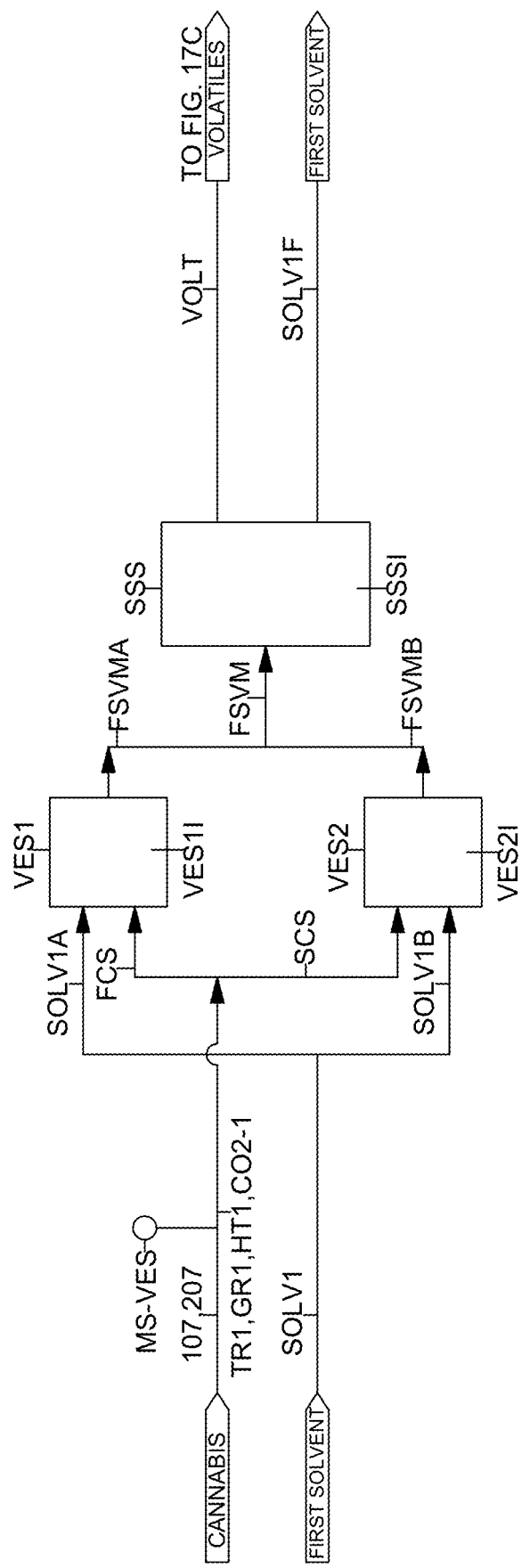
FIG. 17B shows a plurality of volatiles extraction systems (VES1, VES2) equipped with one first solvent separation system (SSS).

The volatiles extraction system (VES) is configured to operate in a plurality of modes of operation. In a first mode of operation, the volatiles extraction system (VES) separates terpenes from the cannabis. The first mode of operation may take place at a first temperature and a first pressure. In a second mode of operation, the volatiles extraction system (VES) separates other volatiles (VOLT) from the cannabis. The second mode of operation may take place at a second temperature and a first pressure. In embodiments, the second temperature is greater than the first temperature. In embodiments, the second pressure is greater than the first pressure.
FIG. 17B FIG. 17B shows a plurality of volatiles extraction systems (VES1, VES2) equipped with one first solvent separation system (SSS). The first volatiles extraction system (VES1) has an interior (VES1I) that is configured to mix cannabis (107, 207), heated cannabis (HT1), ground cannabis (GR1), or trimmed cannabis (TR1) with a first solvent (SOLV1). The second volatiles extraction system (VES2) has an interior (VES1I) that is configured to mix cannabis (107, 207), heated cannabis (HT1), ground cannabis (GR1), or trimmed cannabis (TR1) with a first solvent (SOLV1).

FIG. 17B shows a first cannabis portion (FCS) introduced to the first volatiles extraction system (VES1) and a second cannabis portion (SCS) introduced to the second volatiles extraction system (VES2). The first cannabis portion (FCS) may be weighed prior to being introduced to the first volatiles extraction system (VES1). The second cannabis portion (SCS) may be weighed prior to being introduced to the second volatiles extraction system (VES2). The first cannabis portion (FCS) and/or the second cannabis portion (SCS) may be either cannabis (107, 207), or heated cannabis (HT1), ground cannabis (GR1), trimmed cannabis (TR1), or combinations thereof.

A primary first solvent and volatiles mixture (FSVMA) is discharged from the first volatiles extraction system (VES1). A secondary first solvent and volatiles mixture (FSVMB) is discharged from the second volatiles extraction system (VES1). The primary first solvent and volatiles mixture (FSVMA) and secondary first solvent and volatiles mixture (FSVMB) are combined and introduced to the first solvent separation system (SSS).
FIG. 17C FIG. 17C shows a volatiles and solvent mixing system (VSMS) that is configured to mix the volatiles (VOLT) with a second solvent (SOLV2). The volatiles (VOLT) that are introduced to the interior (VSMSI) of the volatiles and solvent mixing system (VSMS) are transferred from the volatiles extraction systems (VES, VES1, VES2) via the first solvent separation system (SSS) as shown in FIGS. 17A and 17B.

In embodiments, the second solvent (SOLV2) includes one or more from the group consisting of a liquid, acetone, alcohol, oil, ethanol. The second solvent (SOLV2) can be weighed with a mass sensor (MS-SOLV2) prior to being introduced to the interior (VSMSI) of the volatiles and solvent mixing system (VSMS). The volatiles (VOLT) may also be weighed with a mass sensor (MS-VOLT) prior to being introduced to the interior (VSMSI) of the volatiles and solvent mixing system (VSMS). The second solvent (SOLV2) and volatiles (VOLT) are mixed within the interior (VSMSI) of the volatiles and solvent mixing system (VSMS).

The volatiles (VOLT) and second solvent (SOLV2) may be are mixed at varying mass ratios. The volatiles (VOLT) to second solvent (SOLV2) mixing mass ratio is the pounds of volatiles (VOLT) per pounds of second solvent (SOLV2). In embodiments, the mixing mass ratio of volatiles (VOLT) to the second solvent (SOLV2) ranges from 1 pound of volatiles (VOLT) per 1 pound of second solvent (SOLV2), so this would be a mixing mass ratio of 1/1 or 1; In embodiments, the mixing mass ratio of volatiles (VOLT) to the second solvent (SOLV2) ranges from 1 pound of volatiles (VOLT) per 2 pounds of second solvent (SOLV2), so this would be a mixing mass ratio of 1/2 or 0.5; In embodiments, the mixing mass ratio of volatiles (VOLT) to the second solvent (SOLV2) ranges from 1 pound of volatiles (VOLT) per 3 pounds of second solvent (SOLV2), so this would be a mixing mass ratio of 1/3 or 0.33; In embodiments, the mixing mass ratio of volatiles (VOLT) to the second solvent (SOLV2) ranges from 1 pound of volatiles (VOLT) per 4 pounds of second solvent (SOLV2), so this would be a mixing mass ratio of 1/4 or 0.25; In embodiments, the mixing mass ratio of volatiles (VOLT) to the second solvent (SOLV2) ranges from 1 pound of volatiles (VOLT) per 5 pounds of second solvent (SOLV2), so this would be a mixing mass ratio of 1/5 or 0.2; In embodiments, the mixing mass ratio of volatiles (VOLT) to the second solvent (SOLV2) ranges from 1 pound of volatiles (VOLT) per 6 pounds of second solvent (SOLV2), so this would be a mixing mass ratio of 1/6 or 0.16; In embodiments, the mixing mass ratio of volatiles (VOLT) to the second solvent (SOLV2) ranges from 1 pound of volatiles (VOLT) per 7 pounds of second solvent (SOLV2), so this would be a mixing mass ratio of 1/7 or 0.14; In embodiments, the mixing mass ratio of volatiles (VOLT) to the second solvent (SOLV2) ranges from 1 pound of volatiles (VOLT) per 8 pounds of second solvent (SOLV2), so this would be a mixing mass ratio of 1/8 or 0.125; In embodiments, the mixing mass ratio of volatiles (VOLT) to the second solvent (SOLV2) ranges from 1 pound of volatiles (VOLT) per 9 pounds of second solvent (SOLV2), so this would be a mixing mass ratio of 1/9 or 0.11; In embodiments, the mixing mass ratio of volatiles (VOLT) to the second solvent (SOLV2) ranges from 1 pound of volatiles (VOLT) per 10 pounds of second solvent (SOLV2), so this would be a mixing mass ratio of 1/10 or 0.1; In embodiments, the mixing mass ratio of volatiles (VOLT) to the second solvent (SOLV2) ranges from 1 pound of volatiles (VOLT) per 12 pounds of second solvent (SOLV2), so this would be a mixing mass ratio of 1/12 or 0.08; In embodiments, the mixing mass ratio of volatiles (VOLT) to the second solvent (SOLV2) ranges from 1 pound of volatiles (VOLT) per 14 pounds of second solvent (SOLV2), so this would be a mixing mass ratio of 1/14 or 0.07; In embodiments, the mixing mass ratio of volatiles (VOLT) to the second solvent (SOLV2) ranges from 1 pound of volatiles (VOLT) per 16 pounds of second solvent (SOLV2), so this would be a mixing mass ratio of 1/16 or 0.06; In embodiments, the mixing mass ratio of volatiles (VOLT) to the second solvent (SOLV2) ranges from 1 pound of volatiles (VOLT) per 20 pounds of second solvent (SOLV2), so this would be a mixing mass ratio of 1/20 or 0.05; In embodiments, the mixing mass ratio of volatiles (VOLT) to the second solvent (SOLV2) ranges from 1 pound of volatiles (VOLT) per 60 pounds of second solvent (SOLV2), so this would be a mixing mass ratio of 1/60 or 0.016; In embodiments, the mixing mass ratio of volatiles (VOLT) to the second solvent (SOLV2) ranges from 1 pound of volatiles (VOLT) per 100 pounds of second solvent (SOLV2), so this would be a mixing mass ratio of 1/100 or 0.01. In embodiments, the mixing mass ratio of pounds of volatiles (VOLT) per pounds of second solvent (SOLV2) ranges from 0.01 to 1.

Figure 17D:
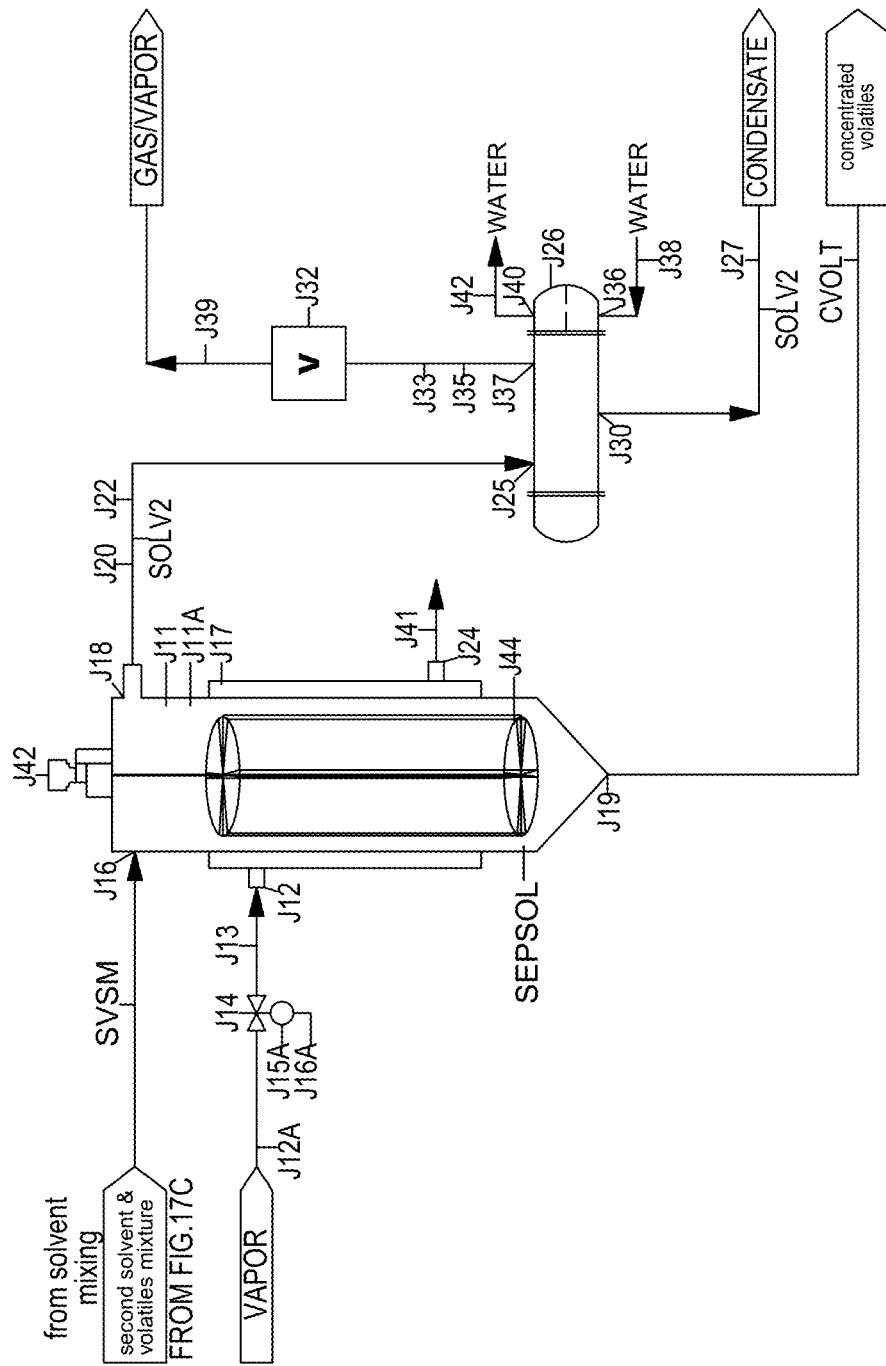
FIG. 17D shows a second solvent separation system (SEPSOL) that is configured to separate at least a portion of the second solvent (SOLV2) from the second volatiles and solvent mixture (SVSM) to produce concentrated volatiles (CVOLT).

A second volatiles and solvent mixture (SVSM) is discharged from the interior (VSMSI) of the volatiles and solvent mixing system (VSMS). FIG. 17D shows one non-limiting embodiment of the second solvent separation system (SEPSOL). The second solvent separation system (SEPSOL) is configured to separate the second solvent (SOLV2) from the second volatiles and solvent mixture (SVSM). The second solvent separation system (SEPSOL) is configured to evaporate at least a portion of the second solvent (SOLV2) from the second volatiles and solvent mixture (SVSM) to create concentrated volatiles (CVOLT). Concentrated volatiles (CVOLT) have a reduced amount of second solvent (SOLV2) relative to the second volatiles and solvent mixture (SVSM). The second solvent separation system (SEPSOL) is configured to separate the second solvent (SOLV2) from the second volatiles and solvent mixture (SVSM) to concentrate the volatiles (VOLT).

The second solvent separation system (SEPSOL) is configured to separate the second solvent (SOLV2) from the second volatiles and solvent mixture (SVSM) by evaporation, distillation, vacuum flashing, or wiped film evaporation. In embodiments, a vacuum may be pulled on the second solvent separation system (SEPSOL) to aide in evaporation of the second solvent (SOLV2) from the second volatiles and solvent mixture (SVSM), as shown in FIG. 17D.

In embodiments, the second solvent (SOLV2) and volatiles (VOLT) are miscible. In embodiments, the second solvent (SOLV2) and oil within the volatiles (VOLT) are miscible. In embodiments, the second solvent (SOLV2) and terpenes within the volatiles (VOLT) are miscible. In embodiments, the second solvent (SOLV2) and wax within the volatiles (VOLT) are miscible. In embodiments, the second solvent (SOLV2) and wax within the volatiles (VOLT) are immiscible.

In instances where the second solvent (SOLV2) and wax within the volatiles (VOLT) are immiscible, a solvent cooler (SOLV-C) is provided to cool the second volatiles and solvent mixture (SVSM) that is evacuated from the interior (VSMSI) of the volatiles and solvent mixing system (VSMS). The solvent cooler (SOLV-C) lowers the temperature of the second volatiles and solvent mixture (SVSM) to permit phase separation of the wax from the volatiles (VOLT). The second volatiles and solvent mixture (SVSM) is a reduced temperature second volatiles and solvent mixture (RTSVSM) as it is leaves the solvent cooler (SOLV-C).

In embodiments, the solvent cooler (SOLV-C) operates at a temperature less than 50 degrees F. In embodiments, the solvent cooler (SOLV-C) operates at a temperature less than 40 degrees F. In embodiments, the solvent cooler (SOLV-C) operates at a temperature less than 30 degrees F. In embodiments, the solvent cooler (SOLV-C) operates at a temperature less than 20 degrees F. In embodiments, the solvent cooler (SOLV-C) operates at a temperature less than 10 degrees F. In embodiments, the solvent cooler (SOLV-C) operates at a temperature less than 00 degrees F. In embodiments, the reduced temperature second volatiles and solvent mixture (RTSVSM) leaves the solvent cooler (SOLV-C) at a temperature including one or more from the group consisting of: less than 50 degrees F., less than 40 degrees F., less than 30 degrees F., less than 20 degrees F., less than 10 degrees F., and less than 0 degrees F.

In embodiments, a solvent filter (SOLV-F) is configured to accept at least a portion of the second volatiles and solvent mixture (SVSM). In embodiments, a solvent filter (SOLV-F) is configured to accept at least a portion of the reduced temperature second volatiles and solvent mixture (RTSVSM). In embodiments, the solvent filter (SOLV-F) is configured to separate wax (WAX) from the second volatiles and solvent mixture (SVSM). In embodiments, the solvent filter (SOLV-F) is configured to separate wax (WAX) from the reduced temperature second volatiles and solvent mixture (RTSVSM). The solvent filter (SOLV-F) discharges a second volatiles and solvent mixture (SVSM) which may then be routed to the second solvent separation system (SEPSOL) of FIG. 17D.

FIG. 17D

FIG. 17D shows a second solvent separation system (SEPSOL) that is configured to separate at least a portion of the second solvent (SOLV2) from the second volatiles and solvent mixture (SVSM) to produce concentrated volatiles (CVOLT).

In embodiments, the second solvent separation system (SEPSOL) includes an evaporator (J11). FIG. 17D shows at least a portion of the second volatiles and solvent mixture (SVSM) transferred to the second solvent separation system (SEPSOL) from the volatiles and solvent mixing system (VSMS) shown in FIG. 17C. The second volatiles and solvent mixture (SVSM) is transferred from the volatiles and solvent mixing system (VSMS) or from the solvent cooler (SOLV-C) or from the solvent filter (SOLV-F) of FIG. 17C to the second solvent separation system (SEPSOL) of FIG. 17D.

FIG. 17D displays the second solvent separation system (SEPSOL) as an evaporator (J11) which separates or evaporates the second solvent (SOLV2) from the second volatiles and solvent mixture (SVSM) to produce concentrated volatiles (CVOLT). In embodiments, the evaporator (J11) is a wiped-film evaporator (J11A). In embodiments, the evaporator (J11) is comprised of one or more from the group consisting of falling film tubular evaporator, rising/falling film tubular evaporator, rising film tubular evaporator, forced circulation evaporator, internal pump forced circulation evaporator, plate evaporator, evaporative cooler, multiple-effect evaporator, thermal vapor recompression evaporator, mechanical vapor recompression evaporator, flash tank, and a distillation column.

The evaporator (J11) shown in FIG. 17D is that of a wiped-film evaporator (J11A). The evaporator (J11) has a vapor inlet (J12), a separator input (J16), a heating jacket (J17), a first output (J18), and a second output (J19). In embodiments, the evaporator (J11) is electrically heated. In embodiments, the vapor inlet (J12) is provided with a vapor (J12A) such as steam. The vapor inlet is connected to a vapor supply conduit (J13). A vapor supply valve (J14) is positioned on the vapor supply conduit (J13). The vapor supply valve (J14) is equipped with a controller (J15A) that is configured to input and output a signal (J15B) to the computer (COMP). In embodiments, the pressure drop across the vapor supply valve (J14) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI. In embodiments, the vapor supply valve (J14) percent open during normal operation ranges from 10% open to 25% open, 25% open to 35% open, 35% open to 45% open, 45% open to 55% open, 55% open to 65% open, 65% open to 75% open, 75% open to 80% open.

A separated vapor transfer conduit (J20) is connected to the first output (J18) and is configured to transfer vaporized solvent (J22) from the evaporator (J11) to a condenser (J26). In embodiments, the vaporized solvent (J22) is the second solvent (SOLV2) in vapor phase. When the second solvent (SOLV2) is evaporated or vaporized into a vaporized solvent (J22) the concentration of the volatiles (VOLT) within the second volatiles and solvent mixture (SVSM) increases to form concentrated volatiles (CVOLT).

The condenser (J26) has a vaporized liquid input (J25) that is configured to transfer the vaporized solvent (J22) or vaporized second solvent (SOLV2) from the separated vapor transfer conduit (J20) to the condenser (J26). The condenser (J26) is configured to accept vaporized solvent (J22) from the evaporator (J11) and condense the liquid into condensate (J27). Condensate (J27) is discharged from the condenser (J26) via a condenser condensate output (J30). The condensate (J27) is the second solvent (SOLV2) which can then be recovered and reused in the volatiles and solvent mixing system (VSMS).

The condenser is connected to a vacuum system (J32) via a gas/vapor transfer conduit (J33). Gas/vapor (J35) is evacuated from the condenser (J27) via a gas/vapor discharge (J37). The gas/vapor (J35) transferred from the condenser to the vacuum system (J32) may be comprised of one or more from the group consisting of second solvent, carbon dioxide, nitrogen, air, steam, water vapor, and non-condensables. The vacuum system (J32) may be any conceivable system configured to draw a vacuum on the condenser (J26). In embodiments, the vacuum system (J32) is that of a liquid-ring vacuum pump. A portion of the gas/vapor (J35) may be in turn condensed within the vacuum system (J26). A portion of the gas/vapor (J35) may be discharged from the vacuum system (J26) via a gas/vapor transfer line (J39).

The condenser (J26) is provided with a cooling water input (J36) and a cooling water output (J40). The cooling water input (J36) is configured to accept a cooling water supply (J38) and the cooling water output (J40) is configured to discharge a cooling water return (J42). The cooling water supply (J38) is configured to reduce the temperature of the vaporized solvent (J22) within the condenser (J26) to convert the vaporized solvent (J22) into a liquid condensate (J27).

The evaporator (J11) has an evaporator condensate output (J24) for evacuating condensate (J41) from the heating jacket (J17). The condensate (J41) discharged via the evaporator condensate output (J24) was provided to the evaporator heating jacket (J17) as the vapor (J12A) or steam. The heating jacket (J17) accepts a source of vapor (J12A), and evaporates second solvent (SOLV2) from the second volatiles and solvent mixture (SVSM) to form vaporized solvent (J22) that is discharged from the evaporator (J11) and sent to the condenser (J26).

The heating jacket (J17) accepts a source of vapor (J12A), and evaporates second solvent (SOLV2) from the second volatiles and solvent mixture (SVSM) to form concentrates volatiles (CVOLT) that has a reduced amount of second solvent (SOLV2) relative to the second volatiles and solvent mixture (SVSM).

In embodiments, the evaporator (J11) takes the form of a wiped-film evaporator (J11A). In embodiments, the wiped-film evaporator (J11A) has a motor (J42) and a wiper (J44). In embodiments, the motor (J42) and wiper (J44) act together to wipe at least one heat transfer surface within the evaporator (J11).

The separator input (J16) is configured to introduce the second volatiles and solvent mixture (SVSM) to the evaporator (J11). In embodiments, the evaporator vaporizes the second solvent (SOLV2) from within the second volatiles and solvent mixture (SVSM) to produce a vaporized solvent (J22) and concentrated volatiles (CVOLT).

In embodiments, the present disclosure describes a method to separate volatiles from cannabis, the method includes:
  (a) providing Grass Weedly Junior or cannabis;
  (b) grinding Grass Weedly Junior or cannabis after step (a);
  (c) extracting volatiles (VOLT) from Grass Weedly Junior or cannabis after step (b) with a first solvent (SOLV1) to form a first solvent and volatiles mixture (FSVM); and
  (d) separating at least a portion of the volatiles (VOLT) from the first solvent and volatiles mixture (FSVM);
wherein:
the volatiles include one or more from the group consisting of oil, wax, terpenes; the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
  (a) providing Grass Weedly Junior or cannabis;
  (b) grinding Grass Weedly Junior or cannabis after step (a);
  (c) extracting volatiles (VOLT) from Grass Weedly Junior or cannabis after step (b) with a first solvent (SOLV1) to form a first solvent and volatiles mixture (FSVM);

(d) separating at least a portion of the volatiles (VOLT) from the first solvent and volatiles mixture (FSVM);
(e) mixing the volatiles with a second solvent (SOLV2) after step (d) to form a second volatiles and solvent mixture (SVSM);
(f) cooling the second volatiles and solvent mixture (SVSM) after step (e);
(g) filtering the second volatiles and solvent mixture (SVSM); and
(h) evaporating the second solvent (SOLV2) from the second volatiles and solvent mixture (SVSM);

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
(a) providing Grass Weedly Junior or cannabis;
(b) grinding Grass Weedly Junior or cannabis after step (a); and
(c) extracting volatiles (VOLT) from Grass Weedly Junior or cannabis after step (b) with a first solvent (SOLV1) to form a first solvent and volatiles mixture (FSVM);
(d) separating at least a portion of the volatiles (VOLT) from the first solvent and volatiles mixture (FSVM);
(e) mixing the volatiles with a second solvent (SOLV2) after step (d) to form a second volatiles and solvent mixture (SVSM);
(f) separating at least a portion of the volatiles (VOLT) from the second solvent (SOLV2);

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
(a) providing Grass Weedly Junior or cannabis;
(b) grinding Grass Weedly Junior or cannabis after step (a);
(c) extracting volatiles (VOLT) from Grass Weedly Junior or cannabis after step (b) with a first solvent (SOLV1) to form a first solvent and volatiles mixture (FSVM);
(d) separating at least a portion of the volatiles (VOLT) from the first solvent and volatiles mixture (FSVM);
(e) mixing a portion of the volatiles (VOLT) after step (d) with insects;

wherein:
the volatiles include one or more from the group consisting of oil, wax, terpenes; the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from cannabis, the method includes:
(a) providing Grass Weedly Junior or cannabis;
(b) grinding Grass Weedly Junior or cannabis after step (a);
(c) extracting volatiles (VOLT) from Grass Weedly Junior or cannabis after step (b) with a first solvent (SOLV1) to form a first solvent and volatiles mixture (FSVM);
(d) separating at least a portion of the volatiles (VOLT) from the first solvent and volatiles mixture (FSVM);
(e) mixing the volatiles (VOLT) with a second solvent (SOLV2) after step (d) to form a second volatiles and solvent mixture (SVSM);
(f) separating at least a portion of the volatiles (VOLT) from the second volatiles and solvent mixture (SVSM);
(g) mixing a portion of the volatiles (VOLT) after step (f) with insects;

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from cannabis, the method includes:
- (a) providing Grass Weedly Junior or cannabis;
- (b) grinding Grass Weedly Junior or cannabis after step (a); and
- (c) extracting volatiles (VOLT) from Grass Weedly Junior or cannabis after step (b) with a first solvent (SOLV1) to form a first solvent and volatiles mixture (FSVM);
- (d) separating at least a portion of the volatiles (VOLT) from the first solvent and volatiles mixture (FSVM);
- (e) mixing the volatiles (VOLT) with a second solvent (SOLV2) after step (d) to form a second volatiles and solvent mixture (SVSM);
- (f) evaporating at least a portion of the second solvent (SOLV2) from the second volatiles and solvent mixture (SVSM) to create concentrated volatiles (CVOLT) that have reduced amount of second solvent relative to the second volatiles and solvent mixture (SVSM);
- (g) mixing a portion of the volatiles (VOLT) after step (f) with insects;

wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.
the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from cannabis, the method includes:
- (a) providing a farming superstructure system (FSS), including:
  - (a1) a first water treatment unit (A1) including a cation configured to remove positively charged ions from water to form a positively charged ion depleted water (06A), the positively charged ions are comprised of one or more from the group consisting of calcium, magnesium, sodium, and iron;
  - (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
  - (a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
  - (a4) an enclosure (ENC) having an interior (ENC1);
  - (a5) a plurality of growing assemblies (100, 200) positioned within the interior (ENC1) of the enclosure (ENC), each growing assembly (100, 200) configured to grow Grass Weedly Junior (107, 207) or cannabis (107, 207);
  - (a6) a plurality of lights (L1, L2) configured to illuminate the interior (ENC1) of the enclosure (ENC);
  - (a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VESI) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VESI) of the volatiles extraction system (VES), the volatiles extraction system (VES) outputs a first solvent and volatiles mixture (FSVM);
  - (a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);
  - (a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
  - (a10) a second solvent separation system (SEPSOL) that is configured to separate at least a portion of the second solvent (SOLV2) from the second volatiles and solvent mixture (SVSM) to produce concentrated volatiles (CVOLT);
- (b) providing a source of water;
- (c) removing positively charged ions and negatively charged ions and optionally undesirable compounds from the water of step (b);
- (d) mixing the water after step (c) with macro-nutrients, micro-nutrients, or a pH adjustment solution to form a liquid mixture;
- (e) pressurizing the liquid mixture after step (d) to form a pressurized liquid mixture;
- (f) transferring the pressurized liquid mixture of step (e) to the plurality of growing assemblies; and
- (g) illuminating the plurality of growing assemblies (100, 200) with the plurality of lights (L1, L2);
- (h) growing Grass Weedly Junior or cannabis within the plurality of growing assemblies after step (g);
- (i) harvesting Grass Weedly Junior or cannabis after growing Grass Weedly Junior or cannabis in step (h);

(j) grinding Grass Weedly Junior or cannabis after step (i); and
(k) extracting volatiles (VOLT) from Grass Weedly Junior or cannabis after step (j) with a first solvent (SOLV1) to form a first solvent and volatiles mixture (FSVM);
(l) separating at least a portion of the volatiles (VOLT) from the first solvent and volatiles mixture (FSVM);
(m) mixing the volatiles (VOLT) with a second solvent (SOLV2) after step (l) to form a second volatiles and solvent mixture (SVSM);
(n) cooling the second volatiles and solvent mixture (SVSM) after step (m);
(o) filtering the second volatiles and solvent mixture (SVSM) after step (n);
(p) evaporating the second solvent (SOLV2) from the second volatiles and solvent mixture (SVSM);
wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
(a) providing a farming superstructure system (FSS), including:
(a1) a cation configured to remove positively charged ions from water to form a positively charged ion depleted water (06A), the positively charged ions are comprised of one or more from the group consisting of calcium, magnesium, sodium, and iron;
(a2) an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
(a4) an enclosure (ENC) having an interior (ENC1);
(a5) a plurality of growing assemblies (100, 200) positioned within the interior (ENC1) of the enclosure (ENC), each growing assembly (100, 200) configured to grow Grass Weedly Junior (107, 207) or cannabis (107, 207);
(a6) a plurality of lights (L1, L2) configured to illuminate the interior (ENC1) of the enclosure (ENC);
(a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VEST) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VEST) of the volatiles extraction system (VES), the volatiles extraction system (VES) outputs a first solvent and volatiles mixture (FSVM);
(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);
(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
(a10) a second solvent separation system (SEPSOL) that is configured to separate at least a portion of the second solvent (SOLV2) from the second volatiles and solvent mixture (SVSM) to produce concentrated volatiles (CVOLT);
(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights (L1, L2);
(h) growing Grass Weedly Junior or cannabis within the plurality of growing assemblies after step (g);
(i) harvesting Grass Weedly Junior or cannabis after growing Grass Weedly Junior or cannabis in step (h);
(j) grinding Grass Weedly Junior or cannabis after step (i); and
(k) extracting volatiles (VOLT) from Grass Weedly Junior or cannabis after step (j) with a first solvent (SOLV1) to form a first solvent and volatiles mixture (FSVM);
(l) separating at least a portion of the volatiles (VOLT) from the first solvent and volatiles mixture (FSVM);
(m) mixing a portion of the volatiles (VOLT) after step (l) with insects;
wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;

the second solvent (SOLV2) includes one or more from the group consisting of a liquid, acetone, alcohol, oil, ethanol;

the terpenes include one or more from the group consisting of limonene, humulene, pinene, linalool, caryophyllene, mycrene, eucalyptol, nerolidol, bisablol, and phytol.

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from cannabis, the method includes:

(a) providing a farming superstructure system (FSS), including:
  (a2) a first water treatment unit (A1) including a cation configured to remove positively charged ions from water to form a positively charged ion depleted water (06A), the positively charged ions are comprised of one or more from the group consisting of calcium, magnesium, sodium, and iron;
  (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
  (a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
  (a4) an enclosure (ENC) having an interior (ENC1);
  (a5) a plurality of growing assemblies (100, 200) positioned within the interior (ENC1) of the enclosure (ENC), each growing assembly (100, 200) configured to grow Grass Weedly Junior (107, 207) or cannabis (107, 207);
  (a6) a plurality of lights (L1, L2) configured to illuminate the interior (ENC1) of the enclosure (ENC);
  (a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VESI) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VEST) of the volatiles extraction system (VES), the volatiles extraction system (VES) outputs a first solvent and volatiles mixture (FSVM);
  (a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);
  (a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
  (a10) a second solvent separation system (SEPSOL) that is configured to separate at least a portion of the second solvent (SOLV2) from the second volatiles and solvent mixture (SVSM) to produce concentrated volatiles (CVOLT);
(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights (L1, L2);
(h) growing Grass Weedly Junior or cannabis within the plurality of growing assemblies after step (g);
(i) harvesting Grass Weedly Junior or cannabis after growing Grass Weedly Junior or cannabis in step (h);
(j) grinding Grass Weedly Junior or cannabis after step (i); and
(k) extracting volatiles (VOLT) from Grass Weedly Junior or cannabis after step (j) with a first solvent (SOLV1) to form a first solvent and volatiles mixture (FSVM);
(l) separating at least a portion of the volatiles (VOLT) from the first solvent and volatiles mixture (FSVM);
(m) mixing the volatiles with a second solvent (SOLV2) after step (l) to form a second volatiles and solvent mixture (SVSM); and
(n) separating at least a portion of the volatiles (VOLT) from the second volatiles and solvent mixture (SVSM);

wherein:

the volatiles include one or more from the group consisting of oil, wax, terpenes;

the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;

the second solvent (SOLV2) includes one or more from the group consisting of a liquid, acetone, alcohol, oil, ethanol;

the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
(a) providing a farming superstructure system (FSS), including:
(a1) a first water treatment unit (A1) including a cation configured to remove positively charged ions from water to form a positively charged ion depleted water (06A), the positively charged ions are comprised of one or more from the group consisting of calcium, magnesium, sodium, and iron;
(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
(a4) an enclosure (ENC) having an interior (ENC1);
(a5) a plurality of growing assemblies (100, 200) positioned within the interior (ENC1) of the enclosure (ENC), each growing assembly (100, 200) configured to grow Grass Weedly Junior (107, 207) or cannabis (107, 207);
(a6) a plurality of lights (L1, L2) configured to illuminate the interior (ENC1) of the enclosure (ENC);
(a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VESI) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VESI) of the volatiles extraction system (VES), the volatiles extraction system (VES) outputs a first solvent and volatiles mixture (FSVM);
(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);
(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);
(a10) a second solvent separation system (SEPSOL) that is configured to separate at least a portion of the second solvent (SOLV2) from the second volatiles and solvent mixture (SVSM) to produce concentrated volatiles (CVOLT);
(b) providing a source of water;
(c) removing positively charged ions and negatively charged ions and optionally undesirable compounds from the water of step (b);
(d) mixing the water after step (c) with macro-nutrients, micro-nutrients, or a pH adjustment solution to form a liquid mixture;
(e) pressurizing the liquid mixture after step (d) to form a pressurized liquid mixture;
(f) transferring the pressurized liquid mixture of step (e) to the plurality of growing assemblies; and
(g) illuminating the plurality of growing assemblies (100, 200) with the plurality of lights (L1, L2);
(h) growing Grass Weedly Junior or cannabis within the plurality of growing assemblies after step (g);
(i) harvesting Grass Weedly Junior or cannabis after growing Grass Weedly Junior or cannabis in step (h);
(j) grinding Grass Weedly Junior or cannabis after step (i); and
(k) extracting volatiles (VOLT) from Grass Weedly Junior or cannabis after step (j) with a first solvent (SOLV1) to form a first solvent and volatiles mixture (FSVM);
(l) separating at least a portion of the volatiles (VOLT) from the first solvent and volatiles mixture (FSVM);
(m) mixing the volatiles with a second solvent (SOLV2) after step (l) to form a second volatiles and solvent mixture (SVSM); and
(n) evaporating at least a portion of the second solvent (SOLV2) from the second volatiles and solvent mixture (SVSM);
wherein:
the volatiles include one or more from the group consisting of oil, wax, terpenes;
the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;
the second solvent (SOLV2) includes one or more from the group consisting of a liquid, acetone, alcohol, oil, ethanol;
the terpenes include one or more from the group consisting of limonene, humulene, pinene, linalool, caryophyllene, mycrene, eucalyptol, nerolidol, bisablol, and phytol.

In embodiments, the present disclosure describes a method to separate volatiles from cannabis, the method includes:
(a) providing a farming superstructure system (FSS), including:
(a1) a first water treatment unit (A1) including a cation configured to remove positively charged ions from water to form a positively charged ion depleted water (06A), the positively charged ions are comprised of one or more from the group consisting of calcium, magnesium, sodium, and iron;
(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow Grass Weedly Junior (107, 207) or cannabis (107, 207);

(a6) a plurality of lights (L1, L2) configured to illuminate the interior (ENC1) of the enclosure (ENC);

(a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VEST) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing Grass Weedly Junior or cannabis within the plurality of growing assemblies after step (g);

(i) harvesting Grass Weedly Junior or cannabis after growing Grass Weedly Junior or cannabis in step (h);

(j) grinding Grass Weedly Junior or cannabis after step (i); and (k) extracting volatiles (VOLT) from Grass Weedly Junior or cannabis after step (j) with a first solvent (SOLV1) to form a first solvent and volatiles mixture (FSVM);

(l) separating at least a portion of the volatiles (VOLT) from the first solvent and volatiles mixture (FSVM);

(m) mixing the volatiles with a second solvent (SOLV2) after step (l) to form a second volatiles and solvent mixture (SVSM);

(n) separating at least a portion of the volatiles (VOLT) from the second volatiles and solvent mixture (SVSM); and (o) mixing a portion of the volatiles (VOLT) after step (n) with insects;

wherein:

the volatiles include one or more from the group consisting of oil, wax, terpenes;

the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;

the second solvent (SOLV2) includes one or more from the group consisting of a liquid, acetone, alcohol, oil, ethanol;

the terpenes include one or more from the group consisting of limonene, humulene, pinene, linalool, caryophyllene, mycrene, eucalyptol, nerolidol, bisablol, and phytol.

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate volatiles from cannabis, the method includes:

(a) providing a farming superstructure system (FSS), including:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow Grass Weedly Junior (107, 207) or cannabis (107, 207);

(a6) a plurality of lights (L1, L2) configured to illuminate the interior (ENC1) of the enclosure (ENC);

(a7) a volatiles extraction system (VES) that is configured to separate volatiles (VOLT) from Grass Weedly Junior (107, 207) or cannabis (107, 207) with use of a first solvent (SOLV1), the volatiles extraction system (VES) has an interior (VEST) that is configured to contain Grass Weedly Junior (107, 207) or cannabis (107, 207), the volatiles extraction system (VES) is configured to accept a first solvent (SOLV1), the first solvent (SOLV1) is configured to contact the Grass Weedly Junior (107, 207) or cannabis (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing Grass Weedly Junior or cannabis within the plurality of growing assemblies after step (g);

(i) harvesting Grass Weedly Junior or cannabis after growing Grass Weedly Junior or cannabis in step (h);

(j) grinding Grass Weedly Junior or cannabis after step (i); and (k) extracting volatiles (VOLT) from Grass Weedly Junior or cannabis after step (j) with a first solvent (SOLV1) to form a first solvent and volatiles mixture (FVSM);

(l) separating at least a portion of the volatiles (VOLT) from the first solvent and volatiles mixture (FVSM); and (m) mixing a portion of the volatiles (VOLT) after step (l) with insects;

wherein:

the first solvent (SOLV1) includes one or more from the group consisting of acetone, alcohol, oil, butane, butter, carbon dioxide, coconut oil, ethanol, gas, gaseous carbon dioxide, hexane, isobutane, isopropanol, liquid carbon dioxide, liquid, naphtha, olive oil, pentane, propane, R134 refrigerant gas, subcritical carbon dioxide, supercritical carbon dioxide, vapor;

the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the present disclosure describes a method to separate and concentrate volatiles from cannabis, the method includes:

(a) providing cannabis;

(b) grinding cannabis after step (a);

(c) separating volatiles (VOLT) from cannabis after step (b) with a first solvent (SOLV1) to form a first solvent and volatiles mixture (FSVM);

(d) separating volatiles (VOLT) from the first solvent and volatiles mixture (FSVM);

(e) mixing the volatiles with a second solvent (SOLV2) after step (d) to form a second volatiles and solvent mixture (SVSM);

(h) separating the second solvent (SOLV2) from the second volatiles and solvent mixture (SVSM);

wherein:

the first solvent (SOLV1) includes one or more from the group consisting of butane, carbon dioxide, gas, gaseous carbon dioxide, hexane, isobutane, isopropanol, liquid carbon dioxide, naphtha, pentane, propane, R134 refrigerant gas, subcritical carbon dioxide, supercritical carbon dioxide, vapor;

the second solvent (SOLV2) includes one or more from the group consisting of a liquid, acetone, alcohol, oil, ethanol.

In embodiments, the method to separate and concentrate volatiles from cannabis, also includes: (e) mixing a portion of the volatiles (VOLT) after step (d) with insects; wherein: the insects are comprised of one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

In embodiments, the method to separate and concentrate volatiles from cannabis, also includes: (f) cooling the second volatiles and solvent mixture (SVSM) after step (e); and (g) filtering the second volatiles and solvent mixture (SVSM).

In embodiments, the method to separate and concentrate volatiles from cannabis, also includes: in step (c), separating volatiles (VOLT) from cannabis using a method that includes: (1) separating terpenes from the cannabis at a first temperature and a first pressure; and (2) separating oil and wax from the cannabis at a second temperature and a second pressure; wherein: the second temperature is greater than the first temperature; the second pressure is greater than the first pressure; the terpenes include one or more from the group consisting of limonene, humulene, pinene, linalool, caryophyllene, mycrene, eucalyptol, nerolidol, bisablol, and phytol; the volatiles include one or more from the group consisting of oil, wax, terpenes.

FIG. 18

Figure 18:
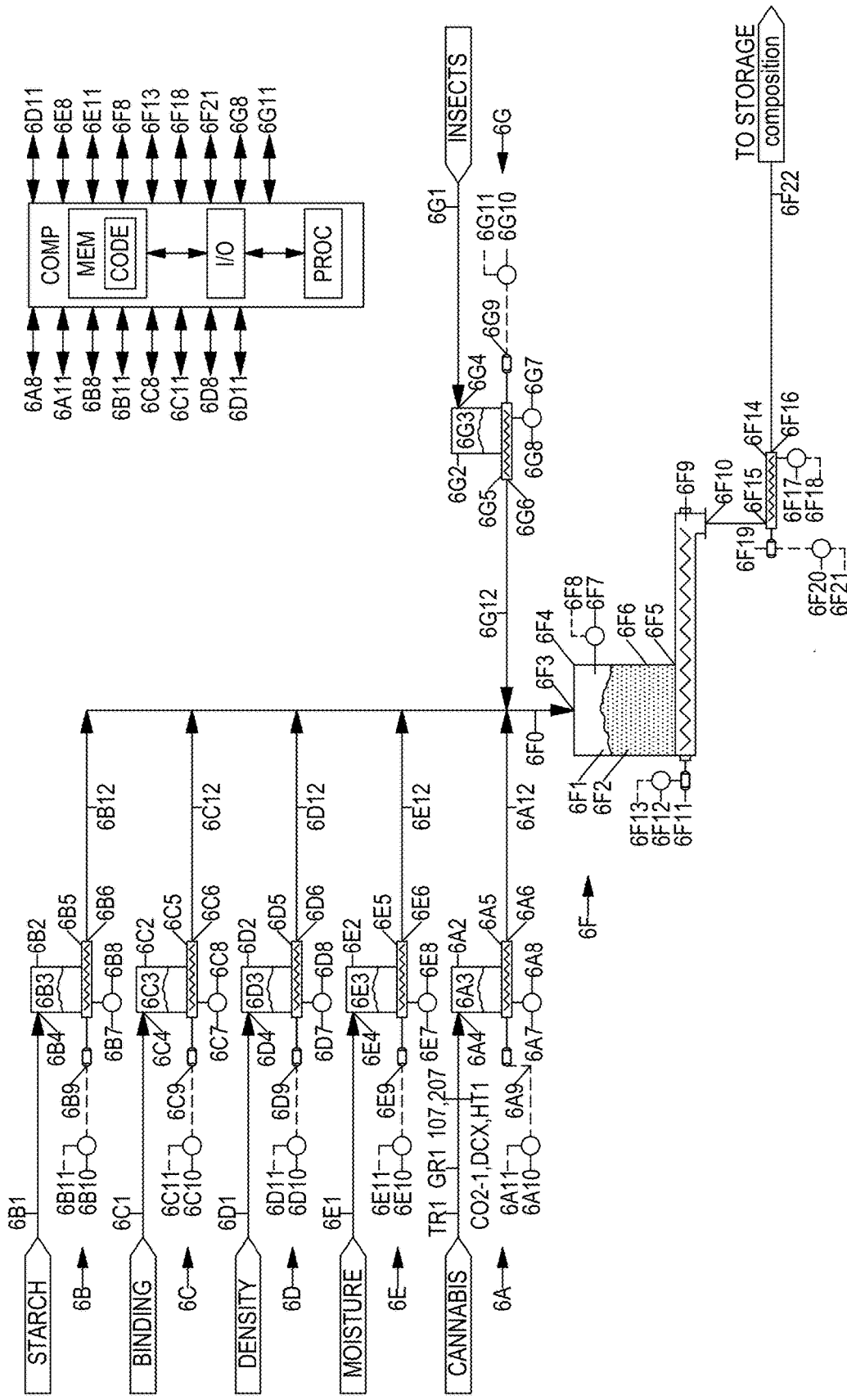
FIG. 18 shows a simplistic diagram illustrating a multifunctional composition mixing module that is configured to generate a multifunctional composition from at least a portion of Grass Weedly Junior (107, 207) that was harvested from each growing assembly (100, 200).

FIG. 18 shows a simplistic diagram illustrating a multi-functional composition mixing module (6000) that is configured to generate a multifunctional composition from at least a portion of the cannabis (107, 207) that was harvested from each growing assembly (100, 200). In embodiments, the cannabis is first trimmed before being mixed with one or more from the group consisting of fiber-starch, binding agent, density improving textural supplement, moisture improving textural supplement, and insects. In embodiments, the cannabis is first trimmed and then grinded before being mixed with one or more from the group consisting of fiber-starch, binding agent, density improving textural supplement, moisture improving textural supplement, and insects.

FIG. 17 displays a cannabis distribution module (6A) including a cannabis tank (6A2) that is configured to accept at least a portion of the cannabis (107, 207) that was harvested from each growing assembly (100, 200). In embodiments, the cannabis is first trimmed before being introduced to the cannabis tank (6A). In embodiments, the cannabis is first trimmed and then grinded before being introduced to the cannabis tank (6A).

The cannabis tank (6A2) has an interior (6A3), a cannabis input (6A4), a cannabis conveyor (6A5), and a cannabis conveyor output (6A6). The cannabis tank (6A2) accepts cannabis to the interior (6A3) and regulates and controls an engineered amount of cannabis (6A1) downstream to be mixed to form a multifunctional composition. In embodiments, the cannabis tank (6A2) accepts trimmed cannabis (TR1) to the interior (6A3). In embodiments, the cannabis tank (6A2) accepts ground cannabis (GR1) to the interior (6A3).

The cannabis conveyor (6A5) has an integrated cannabis mass sensor (6A7) that is configured to input and output a signal (6A8) to the computer (COMP). The cannabis conveyor motor (6A9) has a controller (6A10) that is configured to input and output a signal (6A11) to the computer (COMP). The cannabis mass sensor (6A7), cannabis conveyor (6A5), and cannabis conveyor motor (6A9) are coupled so as to permit the conveyance, distribution, or output of a precise flow of cannabis via a cannabis transfer line (6A12).

FIG. 17 displays a fiber-starch distribution module (6B) including a fiber-starch tank (6B2) that is configured to accept fiber-starch (6B1). The fiber-starch tank (6B2) has an interior (6B3), a fiber-starch input (6B4), a fiber-starch conveyor (6B5), and a fiber-starch conveyor output (6B6). The fiber-starch tank (6B2) accepts fiber-starch (6B1) to the interior (6B3) and regulates and controls an engineered amount of fiber-starch (6B1) downstream to be mixed to form a multifunctional composition. The fiber-starch conveyor (6B5) has an integrated fiber-starch mass sensor (6B7) that is configured to input and output a signal (6B8) to the computer (COMP). The fiber-starch conveyor motor (6B9) has a controller (6B10) that is configured to input and output a signal (6B11) to the computer (COMP). The fiber-starch mass sensor (6B7), fiber-starch conveyor (6B5), and fiber-starch conveyor motor (6B9) are coupled so as to permit the conveyance, distribution, or output of a precise flow of fiber-starch (6B1) via a fiber-starch transfer line (6B12).

FIG. 17 displays a binding agent distribution module (6C) including a binding agent tank (6C2) that is configured to accept a binding agent (6C1). The binding agent tank (6C2) has an interior (6C3), a binding agent input (6C4), a binding agent conveyor (6C5), and a binding agent conveyor output (6C6). The binding agent tank (6C2) accepts binding agent (6C1) to the interior (6C3) and regulates and controls an engineered amount of a binding agent (6C1) downstream to be mixed to form a multifunctional composition. The binding agent conveyor (6C5) has an integrated binding agent mass sensor (6C7) that is configured to input and output a signal (6C8) to the computer (COMP). The binding agent conveyor motor (6C9) has a controller (6C10) that is configured to input and output a signal (6C11) to the computer (COMP). The binding agent mass sensor (6C7), binding agent conveyor (6C5), and binding agent conveyor motor (6C9) are coupled so as to permit the conveyance, distribution, or output of a precise flow of binding agent (6C1) via a binding agent transfer line (6C12).

FIG. 17 displays a density improving textural supplement distribution module (6D) including a density improving textural supplement tank (6D2) that is configured to accept a density improving textural supplement (6D1). The density improving textural supplement tank (6D2) has an interior (6D3), a density improving textural supplement input (6D4), a density improving textural supplement conveyor (6D5), and a density improving textural supplement conveyor output (6D6). The density improving textural supplement tank (6D2) accepts density improving textural supplement (6D1) to the interior (6D3) and regulates and controls an engineered amount of a density improving textural supplement (6D1) downstream to be mixed to form a multifunctional composition. The density improving textural supplement conveyor (6D5) has an integrated density improving textural supplement mass sensor (6D7) that is configured to input and output a signal (6D8) to the computer (COMP). The density improving textural supplement conveyor motor (6D9) has a controller (6D10) that is configured to input and output a signal (6D11) to the computer (COMP). The density improving textural supplement mass sensor (6D7), density improving textural supplement conveyor (6D5), and density improving textural supplement conveyor motor (6D9) are coupled so as to permit the conveyance, distribution, or output of a precise flow of density improving textural supplement (6D1) via a density improving textural supplement transfer line (6D12).

FIG. 17 displays a moisture improving textural supplement distribution module (6E) including a moisture improving textural supplement tank (6E2) that is configured to accept a moisture improving textural supplement (6E1). The moisture improving textural supplement tank (6E2) has an interior (6E3), a moisture improving textural supplement input (6E4), a moisture improving textural supplement conveyor (6E5), and a moisture improving textural supplement conveyor output (6E6). The moisture improving textural supplement tank (6E2) accepts a moisture improving textural supplement (6E1) to the interior (6E3) and regulates and controls an engineered amount of a moisture improving textural supplement (6E1) downstream to be mixed to form a multifunctional composition. The moisture improving textural supplement conveyor (6E5) has an integrated moisture improving textural supplement mass sensor (6E7) that is configured to input and output a signal (6E8) to the computer (COMP). The moisture improving textural supplement conveyor motor (6E9) has a controller (6E10) that is configured to input and output a signal (6E11) to the computer (COMP). The moisture improving textural supplement mass sensor (6E7), moisture improving textural supplement conveyor (6E5), and moisture improving textural supplement conveyor motor (6E9) are coupled so as to permit the conveyance, distribution, or output of a precise flow of moisture improving textural supplement (6E1) via a moisture improving textural supplement transfer line (6E12).

FIG. 17 displays an insect distribution module (6G) including an insect tank (6G2) that is configured to accept insects (6G1). The insect tank (6G2) has an interior (6G3), an insect input (6G4), an insect conveyor (6G5), and an insect conveyor output (6G6). The insect tank (6G2) accepts insects (6G1) to the interior (6G3) and regulates and controls an engineered amount of insects (6G1) downstream to be mixed to form a multifunctional composition. The insect conveyor (6G5) has an integrated insect mass sensor (6G7) that is configured to input and output a signal (6G8) to the computer (COMP). The insect conveyor motor (6G9) has a controller (6G10) that is configured to input and output a signal (6G11) to the computer (COMP). The insect mass sensor (6G7), insect conveyor (6G5), and insect conveyor motor (6G9) are coupled so as to permit the conveyance, distribution, or output of a precise flow of insects (6G1) via an insect transfer line (6G12). In embodiments, the insects may be Orthoptera order of insects including grasshoppers, crickets, cave crickets, Jerusalem crickets, katydids, weta, lubber, acrida, and locusts. However, other orders of insects, such as cicadas, ants, mealworms, agave worms, worms, bees, centipedes, cockroaches, dragonflies, beetles, scorpions, tarantulas, and termites may be used as well.

FIG. 17 displays a multifunctional composition mixing module (6F) including a multifunctional composition tank (6F1) that is configured to accept a mixture including cannabis, fiber-starch (6B1), binding agent (6C1), density improving textural supplement (6D1), moisture improving textural supplement (6E1), and insects (6G1) via a multifunctional composition transfer line (6F0).

The multifunctional composition tank (6F1) has an interior (6F2), a multifunctional composition tank input (6F3), screw conveyor (6F9), multifunctional composition output (6F10). The multifunctional composition tank (6F1) accepts cannabis, fiber-starch (6B1), binding agent (6C1), density improving textural supplement (6D1), moisture improving textural supplement (6E1), and insects (6G1) to the interior (6F2) and mixes, regulates, and outputs a weighed multifunctional composition stream (6F22).

The multifunctional composition tank (6F1) has a top section (6F4), bottom section (6F5), at least one side wall (6F6), with a level sensor (6F7) positioned thereon that is configured to input and output a signal (6F8) to the computer (COMP). The screw conveyor (6F9) has a multifunctional composition conveyor motor (6F11) with a controller (6F12) that is configured to input and output a signal (6F13) to the computer (COMP). From the multifunctional composition output (6F10) of the multifunctional composition tank (6F1) is positioned a multifunctional composition weigh screw (6F14) that is equipped with a multifunctional composition weigh screw input (6F15), a multifunctional composition weigh screw output (6F16), and a mass sensor (6F17) that is configured to input and output a signal (6F18) to the computer (COMP). The multifunctional composition weigh screw (6F14) also has a weigh screw motor (6F19) with a controller (6F20) that is configured to input and output a signal (6F21) to the computer (COMP).

The multifunctional composition mixing module (6000) involves mixing the cannabis with fiber-starch materials, binding agents, density improving textural supplements, moisture improving textural supplements, and optionally insects, to form a multifunctional composition.

The multifunctional composition may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the fiber-starch mass ratio ranges from between about 100 pounds of fiber-starch per ton of multifunctional composition to about 1800 pounds of fiber-starch per ton of multifunctional composition.

In embodiments, the binding agents may be comprised of singular or mixtures of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, psyllium husks, sago, sugars, syrups, tapioca, vegetable gums, or xanthan gum. In embodiments, the binding agent mass ratio ranges from between about 10 pounds of binding agent per ton of multifunctional composition to about 750 pounds of binding agent per ton of multifunctional composition.

In embodiments, the density improving textural supplements may be comprised of singular or mixtures of extracted arrowroot starch, extracted corn starch, extracted lentil starch, extracted potato starch, or extracted tapioca starch. In embodiments, the density improving textural supplement mass ratio ranges from between about 10 pounds of density improving textural supplement per ton of multifunctional composition to about 1000 pounds of density improving textural supplement per ton of multifunctional composition.

In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts. In embodiments, the moisture improving textural supplement mass ratio ranges from between about 10 pounds of moisture improving textural supplement per ton of multifunctional composition to about 1000 pounds of moisture improving textural supplement per ton of multifunctional composition.

In embodiments, insects may be added to the multifunctional composition. In embodiments, the insect mass ratio ranges from between about 25 pounds of insects per ton of multifunctional composition to about 1500 pounds of insects per ton of multifunctional composition.

In embodiments, the cannabis ratio ranges from between about 25 pounds of cannabis per ton of multifunctional composition to about 1800 pounds of cannabis per ton of multifunctional composition.

FIG. 19

Figure 19:
FIG. 19 illustrates a single fully-grown Grass Weedly Junior plant.

FIG. 19 illustrates a single fully-grown Grass Weedly Junior plant.

FIG. 20

Figure 20:
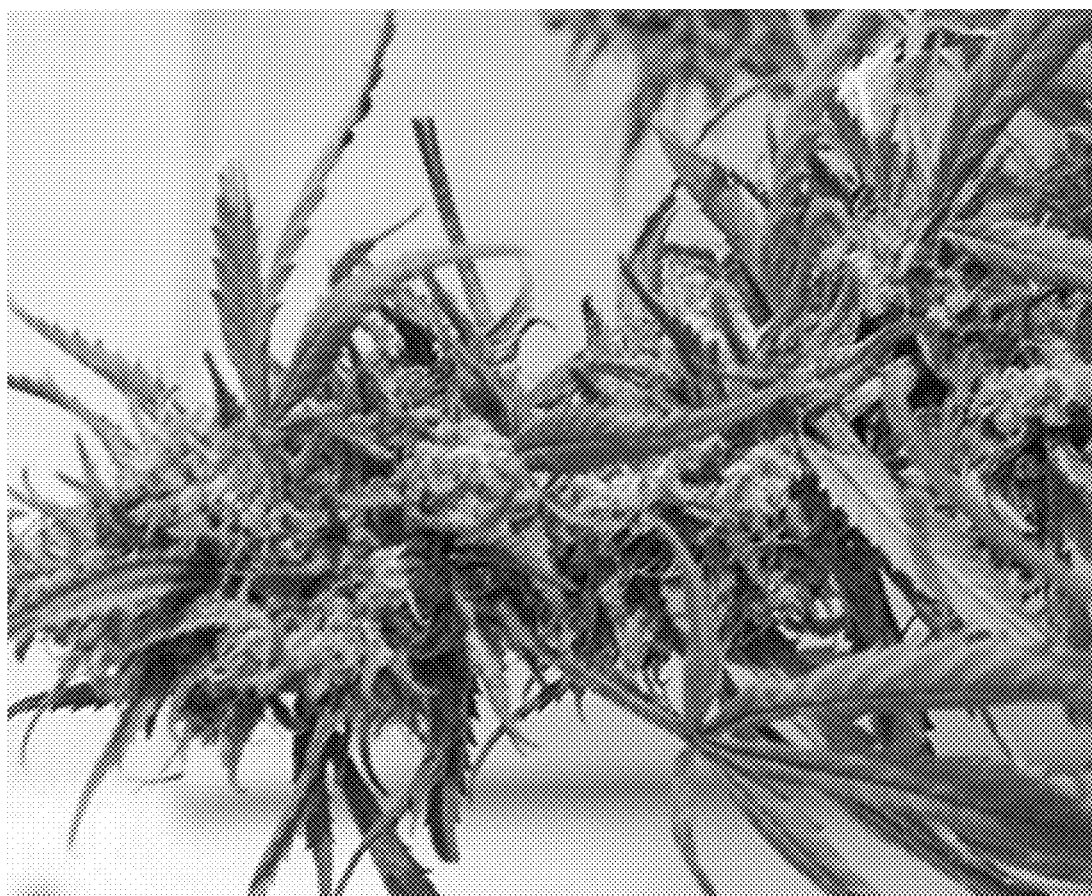
FIG. 20 illustrates zoomed-in view of a budding or flowering plant.

FIG. 20 illustrates zoomed-in view of a budding or flowering plant.

FIG. 21

Figure 21:
FIG. 21 illustrates a single leaf of Grass Weedly Junior.

FIG. 21 illustrates a single leaf of Grass Weedly Junior.

FIG. 22

Figure 22:
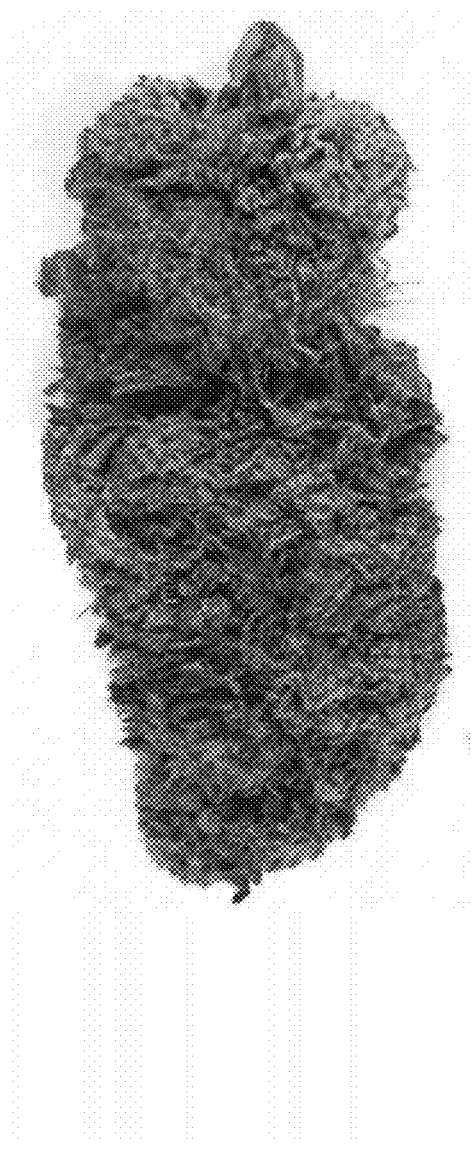
FIG. 22 illustrates a trimmed and dried bud (reproductive structure) of Grass Weedly Junior.
Figure 23:
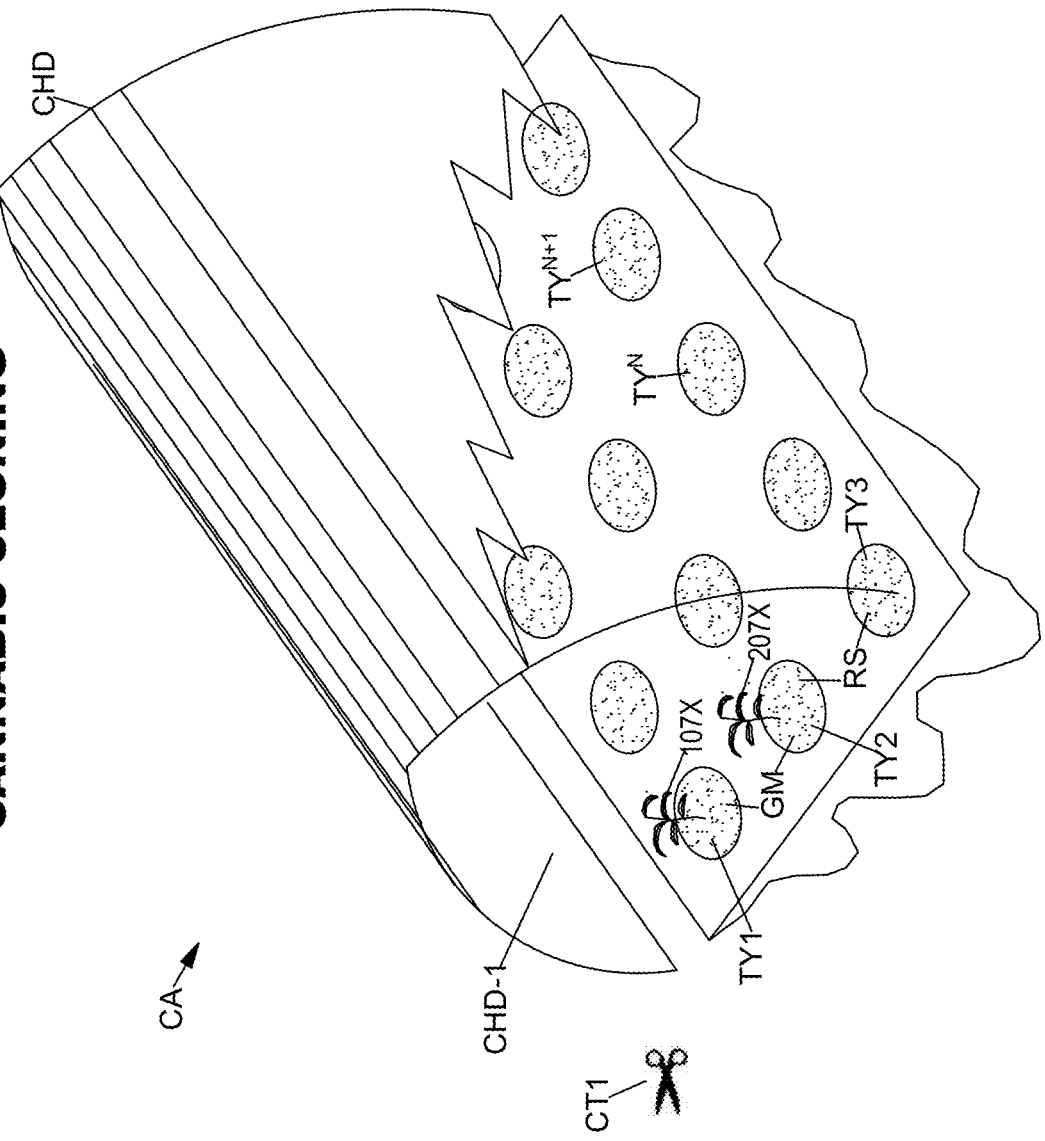
FIG. 23 shows a cannabis cloning assembly (CA) that is configured to clone Grass Weedly Junior (107, 207) that were growing in each growing assembly (100, 200).

FIG. 22 illustrates a trimmed and dried bud (reproductive structure) of Grass Weedly Junior.

FIGS. 19-22 illustrate the overall appearance of the Grass Weedly Junior. These photographs show the colors as true as it is reasonably possible to obtain in reproductions of this type. Colors in the photographs may differ slightly from the color values cited in the detailed botanical description which accurately describe the colors of Grass Weedly Junior.

This disclosure relates to a new and distinct hybrid plant named Grass Weedly Junior characterized by a mixture of *Cannabis sativa* L. ssp. *sativa* X *Cannabis sativa* L. ssp. *indica* (Lam.);

Within the leaves, seeds, stems, roots, or any reproductive structures, Grass Weedly Junior has a:
  (a) a cannabidiol content ranging from 0.00001 weight percent to 25 weight percent;
  (b) a tetrahydrocannabinol content ranging from 4 weigh percent to 66 weigh percent;
  (c) an energy content ranging from between 2,500 British Thermal Units per pound to 65,000 British Thermal Units per pound;
  (d) a carbon content ranging from between 15 weight percent to 66 weight percent;
  (e) an oxygen content ranging from between 10 weight percent to 60 weight percent;
  (f) a hydrogen content ranging from between 2 weight percent to 25 weight percent;
  (g) an ash content ranging from between 2 weight percent to 35 weight percent; and
  (h) volatiles content ranging from between 20 weight percent to 92 weight percent;
  (i) a nitrogen content ranging from between 0.5 weight percent to 20 weight percent;
  (j) a sulfur content ranging from between 0.01 weight percent to 10 weight percent;
  (k) a chlorine content ranging from 0.01 weight percent to 15 weight percent;
  (l) a sodium content ranging from 0.01 weight percent to 20 weight percent;
  (m) a potassium content ranging from 0.01 weight percent to 15 weight percent;
  (n) an iron content ranging from 0.005 weight percent to 15 weight percent;
  (o) a magnesium content ranging from 0.01 weight percent to 11 weight percent;
  (p) a phosphorous content ranging from 0.02 weight percent to 14 weight percent;
  (q) a calcium content ranging from 0.02 weight percent to 12 weight percent;
  (r) a zinc content ranging from 0.01 weight percent to 7 weight percent;
  (s) a cellulose content ranging from 15 weight percent to 77 weight percent;
  (t) a lignin content ranging from 2 weight percent to 40 weight percent;
  (u) a hemicellulose content ranging from 2 weight percent to 36 weight percent;
  (v) a fat content ranging from 4 weight percent to 45 weight percent;
  (w) a fiber content ranging from 5 weight percent to 75 weight percent; and
  (x) a protein content ranging from 5 weight percent to 35 weight percent, as illustrated and described herein;
  wherein:
  the *Cannabis sativa* L. ssp. *sativa* content ranges from 15 weight percent to 85 weight percent;
  the *Cannabis sativa* L. ssp. *indica* (Lam.) content ranges from 15 weight percent to 85 weight percent.

The present plant was developed in the United States. In embodiments, the plant may be propagated from seed. In embodiments, the plant is asexually propagated using stem cuttings especially for large-scale production. The plant may be grown indoors, such as for example in a greenhouse, building, or other suitable indoor growing environment under controlled conditions. In embodiments, the plant is grown outdoors.

Plant

Exposed Plant Structure:

This is an aggressive annual, dioecious plant. The natural height at 6 months old for indoor growth is 40 inches to 120 inches, and, and for outdoor growth is 50 inches to 160 inches. A detailed list of characteristics follows:

Botanical Classification:

Mixture of *Cannabis sativa* L. ssp. *sativa* X *Cannabis sativa* L. ssp. *indica* (Lam.).

Percentages:

*Cannabis sativa* L. ssp. *sativa* content ranges from 15 weight percent to 85 weight percent; *Cannabis sativa* L. ssp. *indica* (Lam.) content ranges from 15 weight percent to 85 weight percent.

Within the leaves, seeds, stems, roots, or any reproductive structures, Grass Weedly Junior has a:
  (a) a cannabidiol content ranging from 0.00001 weight percent to 25 weight percent;
  (b) a tetrahydrocannabinol content ranging from 4 weigh percent to 66 weigh percent;
  (c) an energy content ranging from between 2,500 British Thermal Units per pound to 65,000 British Thermal Units per pound;
  (d) a carbon content ranging from between 15 weight percent to 66 weight percent;
  (e) an oxygen content ranging from between 10 weight percent to 60 weight percent;
  (f) a hydrogen content ranging from between 2 weight percent to 25 weight percent;
  (g) an ash content ranging from between 2 weight percent to 35 weight percent; and
  (h) volatiles content ranging from between 20 weight percent to 92 weight percent;
  (i) a nitrogen content ranging from between 0.5 weight percent to 20 weight percent;
  (j) a sulfur content ranging from between 0.01 weight percent to 10 weight percent;
  (k) a chlorine content ranging from 0.01 weight percent to 15 weight percent;
  (l) a sodium content ranging from 0.01 weight percent to 20 weight percent;

(m) a potassium content ranging from 0.01 weight percent to 15 weight percent;
(n) an iron content ranging from 0.005 weight percent to 15 weight percent;
(o) a magnesium content ranging from 0.01 weight percent to 11 weight percent;
(p) a phosphorous content ranging from 0.02 weight percent to 14 weight percent;
(q) a calcium content ranging from 0.02 weight percent to 12 weight percent;
(r) a zinc content ranging from 0.01 weight percent to 7 weight percent;
(s) a cellulose content ranging from 15 weight percent to 77 weight percent;
(t) a lignin content ranging from 2 weight percent to 40 weight percent;
(u) a hemicellulose content ranging from 2 weight percent to 36 weight percent;
(v) a fat content ranging from 4 weight percent to 45 weight percent;
(w) a fiber content ranging from 5 weight percent to 75 weight percent; and
(x) a protein content ranging from 5 weight percent to 35 weight percent, as illustrated and described herein.

Propagation:

This plant may be perpetuated by stem cuttings. Seed propagation is possible but not preferred due to lack of efficiency when compared to asexual reproduction.

Time to Initiate Roots in Summer:

about 4 to 20 days.

Plant Description:

Annual, dioecious flowering shrub; multi-stemmed; vigorous; freely branching; removal of the terminal bud enhances lateral branch development.

Mature Habit:

Tap-rooted annual, with extensive fibrous root system, upright and much branched aerial portion of plant. The growth form of all cloned plants was highly manipulated by systematic removal of terminal buds, inducing a greater branching habit. Many petiole scars on stems from systematic removal of large shade leaves. In this habit, these are obviously very vigorous annual herbs.

First Year Stems:

Shape: Round. Moderate to fine pubescence.

First year stem strength: Medium to Strong.

First year stem color:

In embodiments, the young stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

In embodiments, the older stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

Stem Diameter:

In embodiments, the stem diameter at the soil line is 1.05 inches to 7.15 inches. In embodiments, the middle of plant average stem diameter is 0.2 inches to 1.5 inches.

In embodiments, the stem diameter at the soil line is 0.75 inches to 4 inches. In embodiments, the middle of plant average stem diameter is 0.2 inches to 1.5 inches.

In embodiments, the stem diameter at the soil line is 0.25 inches to 2 inches. In embodiments, the middle of plant average stem diameter is 0.1 inches to 0.75 inches.

Stem Height:

In embodiments, the stem height is 3 feet to 9 feet. In embodiments, the stem height is 3 feet to 9 feet. In embodiments, the stem height is 1.5 feet to 4.5 feet. In embodiments, the stem height is 5.5 feet to 11.25 feet. In embodiments, the stem height is 10 feet to 20 feet. In embodiments, the stem height is 11 feet to 24.5 feet. In embodiments, the stem height is 18 feet to 32 feet.

Stem Strength:

In embodiments, lateral stems are strong but benefit from being staked during flowering. In embodiments, the stem has a hollow cross-section. In embodiments, the stem is ribbed having ribs that run parallel to the stem. In embodiments, the stem is hollow.

Internode Spacing:

In embodiments, from between 1.15 inches to 2 inches at the top half of the plant. In embodiments, from between 1.15 inches to 3.15 inches at the bottom half of the plant. In embodiments, from between 0.75 inches to 5 inches at the bottom half of the plant. In embodiments, from between 0.35 inches to 3.15 inches at the bottom half of the plant. In embodiments, from between 0.35 inches to 4.15 inches at the bottom half of the plant. In embodiments, from between 1.15 inches to 7.15 inches at the bottom half of the plant. In embodiments, from between 2 inches to 9 inches at the bottom half of the plant. In embodiments, from between 2 inches to 9 inches at the bottom half of the plant.

Foliage Description:

Texture (Upper and Lower Surfaces):

Upper surface scabrid with non-visible stiff hairs; lower surface more or less densely pubescent, covered with sessile glands.

Branch Strength:

Strong to medium to weak.

Branch Description:

In embodiments, branches may be short, dense with short, broad leaflets. In embodiments, branches may be medium length, dense with long, broad or compact leaflets. In embodiments, lateral branches off the main stem may be fine and of medium strength, they contain few leaves with many bud sites extending up the branch. In embodiments, branches may be long and sparse.

Leaf Arrangement:

In embodiments, palmately compound (digitate) leaves with 5 to 9 serrates leaflets per leaf. In embodiments, palmately compound (digitate) leaves with 3 to 7 serrates leaflets per leaf. In embodiments, palmately compound (digitate) leaves with 7 to 11 serrates leaflets per leaf. In embodiments, palmately compound (digitate) leaves with 3 to 11 serrates leaflets per leaf. In embodiments, palmately compound (digitate) leaves with 5 to 11 serrates leaflets per leaf. In embodiments, the bottom two leaflets may be angled upwards at about a 45-degree angle towards the middle leaflet. In embodiments, the bottom two leaflets extend out from the petiole at approximately 180 degrees.

Leaf Width:

In embodiments, the average leaf width ranges from between 1.5 inches to 12 inches. In embodiments, the average leaf width ranges from between 1.5 inches to 3 inches. In embodiments, the average leaf width ranges from between 1.5 inches to 4 inches. In embodiments, the average leaf width ranges from between 1.5 inches to 5 inches. In embodiments, the average leaf width ranges from between 1.5 inches to 6 inches. In embodiments, the average leaf width ranges from between 1.5 inches to 7 inches. In embodiments, the average leaf width ranges from between 1.5 inches to 8 inches. In embodiments, the average leaf width ranges from between 1.5 inches to 10 inches.

Leaf Length:

In embodiments, the average leaf length ranges from between 1.5 inches to 12 inches. In embodiments, the average leaf length ranges from between 1.5 inches to 3 inches. In embodiments, the average leaf length ranges from between 1.5 inches to 4 inches. In embodiments, the average leaf length ranges from between 1.5 inches to 5 inches. In embodiments, the average leaf length ranges from between 1.5 inches to 6 inches. In embodiments, the average leaf length ranges from between 1.5 inches to 7 inches. In embodiments, the average leaf length ranges from between 1.5 inches to 8 inches. In embodiments, the average leaf length ranges from between 1.5 inches to 10 inches.

Leaf Venation Pattern:

Venation of each leaf is palmately compound (digitate), with serrated leaflets. In embodiments, the lateral venation extends off the main vein to each serrated tip. In embodiments, the sublateral veins extend to the notch of each serration rather than the tip. In embodiments, each serration has a lateral vein extending to its tip from the central (primary) vein of the leaflet. In embodiments, the from each lateral vein there is usually a single spur vein (sublateral vein) extending to the notch of each serration.

Leaf Venation Color:

Leaf venation is very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Petiole Length:

Average length of petiole of fan leaves 1.5 inches to 8 inches. In embodiments, Petioles are very study and appear a light brown (166C) or light green (144C) (The Royal Horticultural Society Colour Chart, 1995 Ed.). Petioles are very study.

Petiole Color:

Petioles are very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Color of Emerging Foliage (Upper Surface):

In embodiments, the color of emerging foliage is have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Vegetative Bud (Reproductive Structure) Description:

In embodiments, the dried flower buds (reproductive structures) are a light green (144C), green (124A), or dark green (144A), small to large in nature, diffuse and airy, and coated with glandular trichomes. In embodiments, the fragrance may be quite spicy with an earthy aroma with noticeable hints of pine, clove, citrus, pepper, candy, and tropical fruit. In embodiments, the fragrance is slightly sweet, having a fruity, fresh, musky, cotton-candy, or grape-soda type smell.

Flower Description:

In embodiments, inflorescence (buds, or reproductive structures) may be conical, spherical, cylindrical, tubular, oblong, or rectangular. In embodiments, the flower, bud, or reproductive structures may be devoid of any petals. In embodiments, the flower, bud, or reproductive structures are comprised of a cluster of false spikes with single flowers. These flowers are often paired and enclosed by a bracteole. In embodiments, the wet flower buds have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.).

Seed Description:

In embodiments, the seeds typically brown (172A). In embodiments, the seeds are brown (172A) and have stripes that include one or more colors from the group consisting of light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.). In embodiments, the seeds are on average about 0.1 inches to 0.2 inches in diameter. In embodiments, the seeds are on average about 0.075 inches to 0.4 inches in diameter. The seeds have a high fat content ranging from 4 weight percent to 45 weight percent, with an energy content ranging up to or less than 65,000 British Thermal Units per pound.

Vegetative Bud (Reproductive Structure) Color:

In embodiments, the dried flower buds are very colorful and are comprised of a vast array of different colors including one or more from the group consisting of light green (144C), green (124A), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D), (The Royal Horticultural Society Colour Chart, 1995 Ed.).

Vegetative Bud (Reproductive Structure) & Pistils Color:

In embodiments, the dried flower buds (including reproductive structures) are comprised of one or more from the group consisting of: green (144C or 144A) with yellow (001A) pistils, green (144C or 144A) with yellow orange (011A) pistils, green (144C or 144A) with orange (024A) pistils, green (144C or 144A) with orange red (033B) pistils, green (144C or 144A) with orange pink (027A) pistils, green (144C or 144A) with red (033A) pistils, green (144C or 144A) with dark purple red (046A) pistils, green (144C or 144A) with light red pink (039C) pistils, green (144C or 144A) with red pink (043C) pistils, green (144C or 144A) with dark pink red (045D) pistils, green (144C or 144A) with purple red (054A) pistils, green (144C or 144A) with light blue pink (055C) pistils, green (144C or 144A) with purple (058A) pistils, green (144C or 144A) with purple red (059D) pistils, green (144C or 144A) with blue pink (062A) pistils, green (144C or 144A) with light blue violet (069C) pistils, green (144C or 144A) with violet blue (089A) pistils, green (144C or 144A) with violet (075A) pistils, green (144C or 144A) with dark violet (079A) pistils, green (144C or 144A) with blue violet (083D) pistils, green (144C or 144A) with blue (100A) pistils, green (144C or 144A) with dark blue (103A) pistils, green (144C or 144A) with light blue (104D) pistils, green (144C or 144A) with light green blue (110C) pistils, green (144C or 144A) with green blue (111A) pistils, green (144C or 144A) with grey blue (115C) pistils, green (144C or 144A) with green (124A) pistils, green (144C or 144A) with green blue (125C) pistils, green (144C or 144A) with green (130A) pistils, green (144C or 144A) with dark green (132A) pistils, green (144C or 144A) with light green (149B) pistils, green (144C or 144A) with white (155A) pistils, green (144C or 144A) with orange brown (169A) pistils, green (144C or 144A) with brown (172A) pistils, green (144C or 144A) with brown purple (178A) pistils, green (144C or 144A) with orange pink (179D) (The Royal Horticultural Society Colour Chart, 1995 Ed.).

Bud (Reproductive Structures) Length:

In embodiments, the bud spike length ranges from 0.75 inches to 10 inches. In embodiments, the bud spike length ranges from 0.75 inches to 20 inches. In embodiments, the bud spike length ranges from 0.75 inches to 30 inches. In embodiments, the bud spike length ranges from 0.75 inches to 40 inches.

Bud (Reproductive Structures) Diameter:

Flower size is approximately: 0.25 inches to 3 inches in diameter; and approximately 0.35 to 10 inches in height.

Flowering Time:

In embodiments, flowering time ranges from 5 weeks to 18 weeks. In embodiments, flowering time ranges from 5 weeks to 28 weeks. In embodiments, flowering time ranges from 25 weeks to 37 weeks. In embodiments, flowering time ranges from 35 weeks to 60 weeks. In embodiments, flowering time ranges from 45 weeks to 101 weeks.

Peduncles:

Peduncle strength is weak to medium to strong. In embodiments, they can bend horizontally from weight of flower buds. In embodiments, the average diameter of the peduncles ranges from between 0.2 to 0.5 inches in diameter. In embodiments, the average diameter of the peduncles ranges from between 0.1 to 0.3 inches in diameter. In embodiments, the average diameter of the peduncles ranges from between 0.3 to 1 inches in diameter. In embodiments, the average diameter of the peduncles ranges from between 1 to 2 inches in diameter. In embodiments, texture is smooth with few hairs. In embodiments, texture is moderately smooth, glabrous. In embodiments, texture is coarse with many hairs. In embodiments, pedicels are short to medium length, with visible hairs. They may be scabrid with sessile glands. In embodiments, pedicels are short to medium length, scabrid with sessile glands and visible hairs.

Peduncles Color:

In embodiments, peduncles are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Pedicel Color:

Pedicels are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Seed production on this plant is difficult. Seed production can be induced using colloidal silver solution but even with this step male inflorescence production is marginal. Pollen generated from this procedure may then be collected and used to self-cross with a non-treated female. The relative proportion of male plants is medium/high.

The inflorescences (e.g.—flowers, buds, reproductive structures) of the female plant are used for medical purposes. This plant is very versatile. It can be used to treat a wide range of health disorders. It has many beneficial medicinal qualities. Some uses include: stimulant, anti-inflammatory, pain management, sleep disorders, Tourette syndrome, Parkinson's disease, spasms, post-traumatic stress disorder (PTSD), epilepsy, multiple sclerosis, digestive disorders, Grass Weedly Junior prefers water having an electrical conductivity ranging from 0.10 microsiemens to 100 microsiemens. Other water sources with other electrical conductivity may be suitable but just not as efficient. Grass Weedly Junior prefers water having an electrical conductivity ranging from 0.10 microsiemens to 100 microsiemens is provided by:

(a1) a first water treatment unit (A1) including a cation,
(a2) a second water treatment unit (A2) including an anion, and
(a3) a third water treatment unit (A3) including a membrane.

In embodiments, Grass Weedly Junior is grown using a method by providing water having an electrical conductivity ranging from 0.10 microsiemens to 100 microsiemens, the method includes:

(a) providing:
(a1) a first water treatment unit (A1) including a cation configured to remove positively charged ions from water to form a positively charged ion depleted water (06A), the positively charged ions are comprised of one or more from the group consisting of calcium, magnesium, sodium, and iron;
(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) a third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
(b) providing a source of water;
(c) removing positively charged ions from the water of step (b) to form a positively charged ion depleted water;
(d) removing negatively charged ions from the water after step (c) to form a negatively charged ion depleted water;
(e) removing undesirable compounds from the water after step (d) to form an undesirable compound depleted water;
(f) mixing the undesirable compounds depleted water after step (e) with one or more from the group consisting of macro-nutrients, micro-nutrients, and a pH adjustment to form a liquid mixture;
(g) pressurizing the liquid mixture of step (f) to form a pressurized liquid mixture;
(h) splitting the pressurized liquid mixture into a plurality of pressurized liquid mixtures;
(i) transferring the plurality of pressurized liquid mixtures to each growing assembly;
wherein:
the macro-nutrients are comprised of one or more from the group consisting of nitrogen, phosphorus, potassium, calcium, magnesium, and sulfur;
the micro-nutrients are comprised of one or more from the group consisting of iron, manganese, boron, molybdenum, copper, zinc, sodium, chlorine, and silicon;
the pH adjustment solution is comprised of one or more from the group consisting acid, nitric acid, phosphoric acid, potassium hydroxide, sulfuric acid, organic acids, citric acid, and acetic acid.

This new and remarkable variety of plant prefers that lights illuminate the plant at an illumination on-off ratio ranging from between 0.5 and 5, the illumination on-off ratio is defined as the duration of time when the lights are on and illuminate the plant in hours divided by the subsequent duration of time when the lights are off and are not illuminating the plant in hours before the lights are turned on again. In embodiments, this variety of plant thrives at a carbon dioxide concentration that is greater than 400 parts per million and less than 30,000 parts per million.

In embodiments, the Grass Weedly Junior is grown in a farming superstructure system (FSS) as described here and is grown while the FSS system is operated in a manner that switches from one mode of operation to another mode of operation.

In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one valves (V1, V3, V4) in a cyclical manner to prevent the roots of the cannabis from receiving too much mist or spray or liquid water or water or nutrients.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100) for 5 seconds followed by not transferring water to the first growing assembly (100) for 600 seconds. In embodiments, water is transferred to the second growing assembly (200) for 5 seconds followed by not transferring water to the second growing assembly (200) for 600 seconds. In embodiments, water is transferred to both the first and second growing assemblies (100, 200) for 5 seconds followed by not transferring water to both the first and second growing assemblies (100, 200) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100) for 60 seconds followed by not transferring water to the first growing assembly (100) for 180 seconds. In embodiments, water is transferred to the second growing assembly (200) for 60 seconds followed by not transferring water to the second growing assembly (200) for 180 seconds. 60 divided by 180 is 0.333.

The duration of time when liquid is transferred to at least one growing assembly (100, 200) divided by the duration of time when liquid is not transferred to at least one growing assembly (100, 200) may be considered an open-close ratio. The open-close ratio may be the duration of time when at least one valve (V1, V3, V4) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1, V3, V4) to periodically introduce the pressurized liquid mixture into to each growing assembly with an open-close ratio ranging from between 0.008 to 0.33, the open-close ratio is defined as the duration of time when the valve (V1, V3, V4) is open in seconds divided by the subsequent duration of time when the same valve is closed in seconds before the same valve opens again. The computer (COMP) opens and closes the valves (V1, V3, V4) to periodically introduce the pressurized liquid mixture into to each growing assembly with an open-close ratio ranging from between 0.008 to 0.33.

In embodiments, the open-close ratio varies. The open-close ratio may vary throughout the life of the cannabis contained within the growing assemblies (100, 200). The open-close ratio may vary throughout the stage of development of the cannabis contained within the growing assemblies (100, 200). Stages of development of the cannabis include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be made available to Grass Weedly Junior. The carbohydrates are comprised of one or more from the group consisting of sugar, sucrose, molasses, and plant syrups.

In embodiments, enzymes may be made available to Grass Weedly Junior. The enzymes are comprised of one or more from the group consisting of amino acids, orotidine 5'-phosphate decarboxylase, OMP decarboxylase, glucanase, beta-glucanase, cellulase, xylanase, Hygrozyme®, Cannazyme®, Microzyme®, and Sensizyme®.

In embodiments, vitamins may be made available to Grass Weedly Junior. The vitamins are comprised of one or more from the group consisting of vitamin B, vitamin C, vitamin D, and vitamin E.

In embodiments, hormones may be made available to Grass Weedly Junior. The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol.

In embodiments, microorganisms may be made available to Grass Weedly Junior. The microorganisms are comprised of one or more from the group consisting of bacteria, diazotroph bacteria, diazotrop archaea, azotobacter vinelandii, clostridium pasterianu, fungi, arbuscular mycorrhizal fungi, glomus aggrefatum, glomus etunicatum, glomus intraradices, rhizophagus irregularis, and glomus mosseae.

Permits and Patent Licenses are Required for Growth of Grass Weedly Junior in the United States of America and Internationally.

The claims and specification are in conformity with 37 CFR 1.163, this specification and especially claimed ranges of elements (a) through (x) and other elements of the claims contain as full and complete a disclosure as possible of the plant and the characteristics thereof that distinguish the same over related known varieties, and its antecedents, and particularly point out where and in what manner the variety of plant has been asexually reproduced. Further, in the case of this newly found plant, this specification particularly points out the location and character of the area where the plant was discovered. Applicant is based out of Baltimore, Md., 21202.

The claims and specification are in conformity with 35 U.S.C. 112(a), since this specification and especially claimed ranges of elements (a) through (x) and other elements of the claims contain a written description of the invention, and of the manner and process of making and using it, in such full, clear, concise, and exact terms as to enable any person skilled in the art to which it pertains, or with which it is most nearly connected, to make and use the same, and shall set forth the best mode contemplated by the inventor or joint inventor of carrying out the invention.

Complete botanical description and the characteristics which distinguish over related known varieties are herein provided. The new variety differs from parents and related (similar) cultivars of *Cannabis sativa* L. ssp. *sativa* and *Cannabis sativa* L. ssp. *indica* (Lam.). The new variety differs from parents and related (similar) cultivars because Grass Weedly Junior has a precise and unique engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, as well as specific *Cannabis sativa* L. ssp.

*sativa* and *Cannabis sativa* L. ssp. *indica* (Lam.) contents and ratios. The new plant differs from its parents and related cultivars because it is engineered to more effectively alleviate inflammation, manage pain, treat post-traumatic stress disorder (PTSD), and digestive disorders, while also helping to prevent sleep disorders. It provides adequate stimulant to cure attention deficit disorder but does not so act as such a stimulating drug to prevent normal sleep, dietary, and exercise patterns. Because of this remarkable new plant, and combination of ingredients, individuals seeking to medicate with tetrahydrocannabinol can now use this plant as medicine while having little-to-no side effects at all whatsoever and at a very low dosage compared to its parents and related cultivars.

Applicant has specifically identified the characteristic of improved medicinal benefits through extensive trial and error and has a claim which is the result of quantifiable, experimental, and empirical data characterizing the difference between Grass Weedly Junior and *Cannabis sativa* L. ssp. *sativa* or *Cannabis sativa* L. ssp. *indica* (Lam.) alone. Most importantly, Grass Weedly Junior possesses a volatiles content ranging from between 20 weight percent to 92 weight percent, and a *Cannabis sativa* L. ssp. *sativa* content ranges from 15 weight percent to 85 weight percent, and a *Cannabis sativa* L. ssp. *indica* (Lam.) content ranges from 15 weight percent to 85 weight percent. Whereas the patents and cultivars possess 100 weight percent of each of *Cannabis sativa* L. ssp. *sativa* content and a *Cannabis sativa* L. ssp. *indica* (Lam.), applicant's research and development has resulted in a new and distinct plant that has an engineered amount of volatiles while mixing *Cannabis sativa* L. ssp. *sativa* content and a *Cannabis sativa* L. ssp. *indica* (Lam.) at varying ratios to achieve a preferred cannabidiol content ranging from 0.00001 weight percent to 25 weight percent. Applicant has realized that the tetrahydrocannabinol content ranging from 4 weigh percent to 66 weigh percent is specifically tailored to maximize dosage while having a volatiles content ranging from between 20 weight percent to 92 weight percent. The combination of Grass Weedly Junior having a volatiles content ranging from between 20 weight percent to 92 weight percent together with the tetrahydrocannabinol content ranging from 4 weigh percent to 66 weigh percent provides a remarkable new plant. Because of this, a user can use less of the plant to achieve the required dosage.

The application conforms to 37 CFR 1.163(a) since the specification particularly points out that Applicant is based out of Baltimore, Md., USA in zip code 21202 which was the location that Applicant realized that he can take stem cuttings and asexually reproduce plants in a manner disclosed in this specification. This disclosure conforms to 37 CFR 1.163(a) since the specification particularly points out that Baltimore, Md., USA in zip code 21202, indoor propagation, growing, and cultivation were the location and character of the area where the plant was discovered.

Applicant has generated the ranges of claimed ranges of elements (a) through (x) were discovered through comprehensive compositional analysis, particle-induced X-ray emission analysis, elemental analysis, proximate analysis, and ultimate analysis immediately available from a variety of different laboratories in the USA. Obtaining the appropriate ranges of varying concentrations of *Cannabis sativa* L. ssp. *sativa* and *Cannabis sativa* L. ssp. *indica* (Lam.) were performed on a trial and error basis. The tetrahydrocannabinol concentration is provided as a measurement of Grass Weedly Junior's leaves, seeds, stems, roots, or any reproductive structures on a dry basis.

The age and growing conditions of this plant shown in FIGS. 1-4 may be: adult plant of 14 weeks, average temperature 70 degrees F. to 80 degrees F., humidity 45 to 55 percent humidity, water pH from 5.15 to 6.75, water having an electrical conductivity ranging from 0.10 microsiemens to 100 microsiemens, an illumination on-off ratio ranging from between 0.5 and 5 (the illumination on-off ratio is defined as the duration of time when the lights are on and illuminate the cannabis in hours divided by the subsequent duration of time when the lights are off and are not illuminating the cannabis in hours before the lights are turned on again), a carbon dioxide concentration that is greater than 400 parts per million and less than 3,000 parts per million. LED lighting wavelength ranging from 400 nm to 700 nm, air velocity ranging from 5 feet per second to 50 feet per second.

The parents of the instant plant are known and are comprised of *Cannabis sativa* L. ssp. *sativa* X *Cannabis sativa* L. ssp. *indica* (Lam.). Seeds from either are commercially available from many vendors throughout the USA. Applicant devised various plant hybrids of *Cannabis sativa* L. ssp. *sativa* X *Cannabis sativa* L. ssp. *indica* (Lam.) to create a plant best suited to accommodate industrial, commercial, recreation and medicinal popular demand.

The idea of a superior and precisely engineered composition that embodies Grass Weedly Junior as described and disclosed herein was discovered by the applicant's in his garden where the inventor was asexually reproducing and cultivating many plants, in many different containers, of many different species. Applicant's work with plants has resulted in the discovery of a cross between *Cannabis sativa* L. ssp. *sativa* X *Cannabis sativa* L. ssp. *indica* (Lam.) described herein. Applicant has discovered that Grass Weedly Junior can be reproduced asexually, by taking cuttings of the plants of origin resulting in a remarkable new plant. The discovered female plant can be asexually reproduced by cuttings.

The invention employs a novel plant variety. Since the plant is essential to the claimed invention it must be obtainable by the following method. A method to asexually clone a plurality of Grass Weedly Junior plants, the method includes:
  (a) providing:
    (a0) a plurality of Grass Weedly Junior (107, 207) plants;
    (a1) a cutting tool (CT1);
    (a2) a liquid, powder, or gel rooting solution (RS), the rooting solution includes one or more from the group consisting of water, carbohydrates, enzymes, vitamins, hormones, and microorganisms;
    (a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene; and
    (a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);

(a5) the cloning enclosure (CHD) has an interior (CHD-1), the cloning enclosure (CHD) is configured to contain water vapor within the interior (CHD-1) to provide a humid environment for plants within the interior (CHD-1);

(b) introducing the rooting solution and the growing medium to the plurality of containers;

(c) using the cutting tool to sever the tips from a plurality of Grass Weedly Junior plants to form a plurality of severed plants (107X, 207X);

(d) inserting the plurality of severed plants (107X, 207X) of step (c) into the plurality of containers;

(e) placing the plurality of containers within the interior of the cloning enclosure;

(f) illuminating the plants after step (e);

(g) growing the plants for 4 to 20 days or until roots are formed; and (h) optionally venting the interior of the clear humidly dome;

wherein:

the carbohydrates are comprised of one or more from the group consisting of sugar, sucrose, molasses, and plant syrups;

the enzymes are comprised of one or more from the group consisting of amino acids, orotidine 5'-phosphate decarboxylase, OMP decarboxylase, glucanase, beta-glucanase, cellulase, xylanase, Hygrozyme®, Cannazyme®, Microzyme®, and Sensizyme®;

the vitamins are comprised of one or more from the group consisting of vitamin B, vitamin C, vitamin D, and vitamin E;

the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotrop archaea, azotobacter vinelandii, clostridium pasteurianu, fungi, arbuscular mycorrhizal fungi, mycorrhiza, glomus aggrefatum, glomus etunicatum, glomus intraradices, rhizophagus irregularis, and glomus mosseae.

TABLE 1

USDA Plants Growth Habit Code: FB;
Vigor: 5;
Productivity: Good;
Flowering timing: 5 weeks to 18 weeks;
Flowering score: 7.5;
Branches: strong to medium to weak;
cannabidiol content ranging from 0.00001 weight percent to 25 weight percent;
tetrahydrocannabinol content ranging from 4 weigh percent to 66 weigh percent;
energy content ranging from between 2,500 BTU per pound to 65,000 BTU per pound;
carbon content: 15 weight percent to 66 weight percent;
oxygen content: 10 weight percent to 60 weight percent;
hydrogen content: 2 weight percent to 25 weight percent;
ash content: 2 weight percent to 35 weight percent; and
volatiles content: 20 weight percent to 92 weight percent;
nitrogen content: 0.5 weight percent to 20 weight percent;
sulfur content: 0.01 weight percent to 10 weight percent;
chlorine content: 0.01 weight percent to 15 weight percent;
sodium content: 0.01 weight percent to 20 weight percent;
potassium content: 0.01 weight percent to 15 weight percent;
iron content: 0.005 weight percent to 15 weight percent;
magnesium content: 0.01 weight percent to 11 weight percent;
phosphorous content: 0.02 weight percent to 14 weight percent;
calcium content: 0.02 weight percent to 12 weight percent;

TABLE 1-continued zinc content: 0.01 weight percent to 7 weight percent;
cellulose content: 15 weight percent to 77 weight percent;
lignin content: 2 weight percent to 40 weight percent;
hemicellulose content: 2 weight percent to 36 weight percent;
fat content: 4 weight percent to 45 weight percent;
fiber content: 5 weight percent to 75 weight percent;
protein content: 5 weight percent to 35 weight percent;
*Cannabis sativa* L. ssp. *Sativa* content ranges from 15 weight percent to 85 weight percent;
*Cannabis sativa* L. ssp. *Indica* (Lam.) content ranges from 15 weight percent to 85 weight percent, It will be appreciated that the foregoing examples, given for purposes of illustration, are not to be construed as limiting the scope of this disclosure. Although only a few exemplary embodiments of this disclosure have been described in detail above, those skilled in the art will readily appreciate that many variation of the theme are possible in the exemplary embodiments without materially departing from the novel teachings and advantages of this disclosure. Accordingly, all such modifications are intended to be included within the scope of this disclosure that is defined in the following claims and all equivalents thereto. Further, it is recognized that many embodiments may be conceived in the design of a given system that do not achieve all of the advantages of some embodiments, yet the absence of a particular advantage shall not be construed to necessarily mean that such an embodiment is outside the scope of the present disclosure.

Thus, specific systems and methods of an automated fluidized bed level and density measurement system have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C ... and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

FIG. 23

FIG. 17 shows one non-limiting embodiment of a cannabis cloning assembly (CA).

In embodiments, the cannabis cloning assembly (CA) includes a plurality of containers (TY1, TY2, TY3, $TY^N$, $TY^{N+1}$) connected to at least one cloning enclosure (CHD). The cloning enclosure (CHD) when placed upon the plurality of containers (TY1, TY2, TY3, $TY^N$, $TY^{N+1}$) forms an interior (CHD-1). In embodiments, the cloning enclosure (CHD) does not let humidity, water vapor, carbon dioxide, or air to escape from within the interior (CHD-1). The cloning enclosure (CHD) is configured to contain humidity in the interior (CHD-1) above the plurality of containers (TY1, TY2, TY3, $TY^N$, $TY^{N+1}$).

The cannabis cloning assembly (CA) is configured to asexually reproduce Grass Weedly Junior (107, 207) that grow within in each growing assembly (100, 200). The present disclosure provides for a method to asexually clone a plurality of Grass Weedly Junior (107, 207) plants, the method includes:

(a) providing:
  (a0) a plurality of Grass Weedly Junior (107, 207) plants;
  (a1) a cutting tool (CT1);
  (a2) a liquid, powder, or gel rooting solution (RS), the rooting solution includes one or more from the group consisting of water, carbohydrates, enzymes, vitamins, hormones, and microorganisms;
  (a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene; and
  (a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);
  (a5) the cloning enclosure (CHD) has an interior (CHD-1), the cloning enclosure (CHD) is configured to contain water vapor within the interior (CHD-1) to provide a humid environment for plants within the interior (CHD-1);
(b) introducing the rooting solution and the growing medium to the plurality of containers;
(c) using the cutting tool to sever the tips from a plurality of Grass Weedly Junior plants to form a plurality of severed plants (107X, 207X);
(d) inserting the plurality of severed plants (107X, 207X) of step (c) into the plurality of containers;
(e) placing the plurality of containers within the interior of the cloning enclosure;
(f) illuminating the plants after step (e);
(g) growing the plants for 4 to 20 days or until roots are formed; and
(h) optionally venting the interior of the clear humidly dome;

wherein:
the carbohydrates are comprised of one or more from the group consisting of sugar, sucrose, molasses, and plant syrups;
the enzymes are comprised of one or more from the group consisting of amino acids, orotidine 5'-phosphate decarboxylase, OMP decarboxylase, glucanase, beta-glucanase, cellulase, xylanase, Hygrozyme®, Cannazyme®, Microzyme®, and Sensizyme®;
the vitamins are comprised of one or more from the group consisting of vitamin B, vitamin C, vitamin D, and vitamin E;
the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotrop archaea, azotobacter vinelandii, clostridium pasteurianu, fungi, arbuscular mycorrhizal fungi, mycorrhiza, glomus aggrefatum, glomus etunicatum, glomus intraradices, rhizophagus irregularis, and glomus mosseae.

LISTING OF REFERENCE NUMERALS farming superstructure system (FSS)
liquid distribution module (LDM)
plant growing module (PGM)
first growing assembly (100, 100', 100", 100''')
first interior (101)
top (102, 102')
bottom (103, 103')
longitudinal axis (AX1)
fabric (104, 104')
upper-section (105)
lower-section (106)
cannabis (107)
lights (L1)
controller (CL1)
signal (XL1)
fan (FN1)
controller (CF1)
signal (XF1)
liquid distributor (108)
restrictions (109)
drain port (110, 110')
drain conduit (111, 111')
support connection (111X)
first drain connection (112, 112')
first liquid supply conduit (113, 113')
support connection (113X, 113X')
liquid input (114, 114')
first smaller diameter (D2)
first connection (X1)
first reducer (R1)
first growing assembly liquid supply valve (V3, V3')
controller (CV3)
signal (XV3)
back-flow prevention valve (BF1)
temperature sensor (T1)
signal (XT1)
upper temperature sensor (T1C)
signal (XT1C)
partition temperature sensor (T1B)
signal (XT1B)
lower temperature sensor (T1A)
signal (XT1A)
CO2 input (115)
CO2 header connection (115X)
CO2 supply conduit (116)
second carbon dioxide supply valve (V8)
controller (CV8)
signal (XV8)
CO2 flow sensor (FC1)
signal (XFC1)
gas quality sensor (GC1)
signal (XGC1)
second growing assembly (200, 200', 200", 200''')
second interior (201)
top (202, 202')
bottom (203, 203')
longitudinal axis (AX2)
fabric (204, 204')
upper-section (205)
lower-section (206)
cannabis (207)
lights (L2)
controller (CL2)
signal (XL2)
fan (FN2)
controller (CF2)
signal (XF2)
liquid distributor (208)
restrictions (209)
drain port (210, 210')
drain conduit (211, 211')
support connection (211X)
second drain connection (212, 212')
second liquid supply conduit (213, 213')
support connection (213X, 213X')
liquid input (214, 214')
second smaller diameter (D3)
second connection (X2)
second reducer (R2)
second growing assembly liquid supply valve (V4, V4')
controller (CV4)
signal (XV4)
back-flow prevention valve (BF2)
temperature sensor (T2)
signal (XT2)
upper temperature sensor (T2C)
signal (XT2C)
partition temperature sensor (T2B)
signal (XT2B)
lower temperature sensor (T2A)
signal (XT2A)
CO2 input (215)
CO2 header connection (215X)
CO2 supply conduit (216)
third carbon dioxide supply valve (V9)
controller (CV9)
signal (XV9)
CO2 flow sensor (FC2)
signal (XFC2)
gas quality sensor (GC2)
signal (XGC2)
carbon dioxide tank (CO2T)
carbon dioxide (CO2)
first carbon dioxide supply valve (V10)
carbon dioxide pressure sensor (CO2P)
carbon dioxide supply header (CO2H)
common drain conduit (517)
drain input (518)
common reservoir (500, 500')
reservoir pH sensor (PH0)
signal (XPH0)
reservoir temperature sensor (T0)
signal (XT0)
reservoir oxygen emitter (EZ)
signal (XEZ)
reservoir electrical conductivity sensor (E1)
signal (XE1)
upper level switch (LH)
signal (XLH)
lower level switch (LL)
signal (XLL)
reservoir recirculation pump (P0)

reservoir recirculation outlet (510)
reservoir recirculation pump suction conduit (512)
reservoir recirculation pump discharge conduit (514)
reservoir recirculation filter (F3)
reservoir heat exchanger (HX2)
reservoir recirculation inlet (516)
liquid supply header (300, 300')
diameter (D1)
reservoir transfer outlet (302)
pump suction conduit (303)
pump discharge conduit (304)
pump (P1)
motor (MP1)
controller (CP1)
signal (XP1)
pump (P1')
first filter (F1)
first filter inlet valve (FV1)
first filter outlet valve (FV2)
second filter (F2)
second filter inlet valve (FV3)
second filter outlet valve (FV4)
filter back-flush supply valve (FV5)
filter back-flush discharge valve (FV6)
filter back-flush supply conduit (306)
filter back-flush outlet (307)
filter back-flush pump (308)
filter back-flush discharge conduit (309)
level control valve (LCV)
controller (CCV)
signal (XCV)
level control discharge conduit (310)
connection (311)
filter (F4)
waste treatment unit (312)
ozone unit (313)
filter inlet pressure sensor (P2)
signal (XP2)
filter discharge pressure sensor (P3)
signal (XP3)
pressure tank (PT)
growing assembly liquid supply valve (V1)
controller (CV1)
signal (XV1)
liquid flow sensor (F0)
signal (XF0)
electrical conductivity sensor (E2)
signal (XE2)
first oxygen emitter (EZ1)
signal (XEZ1)
second oxygen emitter (EZ2)
signal (XEZ2)
third oxygen emitter (EZ3)
signal (XEZ3)
liquid heat exchanger (HX3)
liquid temperature sensor (T3)
signal (XT3)
water supply (01)
water supply conduit (02)
first water inlet (03)
second water inlet (03')
third water inlet (03")
fourth water inlet (03")
first water treatment unit (A1)
first input (04)
first output (05)
first contaminant depleted water (06)
positively charged ion depleted water (06A)
filter (y1)
activated carbon (y2)
adsorbent (y3)
cation (y4)
anion (y5)
polishing unit (y6)
low voltage shut-off switch (LVV-1)
low voltage shut-off switch (LVV-2)
second water treatment unit (A2)
second input (07)
second output (08)
second contaminant depleted water (09)
negatively charged ion depleted water (09A)
third water treatment unit (A3)
third input (10)
third output (11)
third contaminant depleted water (12)
undesirable compounds depleted water (12A)
first water pressure sensor (13)
water input conduit (14)
contaminant-laden water (15)
water supply valve (16)
controller (17)
solution tank (18)
interior (19)
water input (20)
diptube (20a)
water supply conduit (21)
water output (22)
water discharge conduit (23)
water supply pump (24)
high level sensor (25)
low level sensor (26)
second water pressure sensor (27)
pressurized liquid transfer conduit (28)
first pressurized liquid transfer conduit (28A)
second pressurized liquid transfer conduit (28B)
third pressurized liquid transfer conduit (28C)
fourth pressurized liquid transfer conduit (28D)
pressurized liquid (29)
first split pressurized liquid (29A)
second split pressurized liquid (29B)
third split pressurized liquid (29C)
fourth split pressurized liquid (29D)
flow sensor (30)
water quality sensor (33)
oxygen emitter (35)
oxygen emitter connection (36)
mixer (38)
motor (39)
load cell (40)
contaminant depleted water valve (V0A)
controller (CV0A)
signal (XV0A)
contaminant depleted water valve (V0B)
controller (CV0B)
signal (XV0B)
contaminant depleted water valve (V0C)
controller (CV0C)
signal (XV0C)
contaminant depleted water valve (V0D)
controller (CV0D)
signal (XV0D)
water heat exchanger (HX1)
macro-nutrient supply tank (600)
macro-nutrients (601)

macro-nutrient transfer conduit (602)
macro-nutrient supply valve (V5)
controller (CV5)
signal (XV5)
macro-nutrient flow sensor (F5)
signal (XF5)
macro-nutrient reservoir input (Z1)
input (603)
load cell (604)
mixer (605)
diptube (606)
micro-nutrient supply tank (700)
micro-nutrients (701)
micro-nutrient transfer conduit (702)
micro-nutrient supply valve (V6)
controller (CV6)
signal (XV6)
micro-nutrient flow sensor (F6)
signal (XF6)
micro-nutrient reservoir input (Z2)
input (703)
load cell (704)
mixer (705)
diptube (706) (not shown)
pH adjustment solution supply tank (800)
pH adjustment solution (801)
pH adjustment solution transfer conduit (802)
pH adjustment solution supply valve (V7)
controller (CV7)
signal (XV7)
pH adjustment solution flow sensor (F7)
signal (XF7)
pH adjustment solution reservoir input (Z3)
input (803)
load cell (804)
mixer (805)
diptube (806) (not shown)
first vertically stacked system (1500)
second vertically stacked system (1500')
third vertically stacked system (1500")
fourth vertically stacked system (1500''')
first vertical support structure (VSS1)
first vertical support structure (VSS1')
second vertical support structure (VSS2)
second vertical support structure (VSS2')
first horizontal support structure (SS1)
first horizontal support structure (SS1')
second horizontal support structure (SS2)
second horizontal support structure (SS2')
base height (H0)
liquid level (LIQ)
reservoir height (H500)
first base height (H100A)
first partition height (H100B)
first growing assembly height (H100C)
second base height (H200A)
second partition height (H200B)
second growing assembly height (H200C)
total height (HT)
width (W1500)
spacing (1500S)
enclosure (ENC)
interior (ENC1)
liquid level (LIQ')
reservoir height (H500')
first base height (H100A')
first partition height (H100B')
first top height (H100C')
second base height (H200A')
second partition height (H200B')
second top height (H200C')
total height (HT')
temperature control unit (TCU)
first side wall (1W)
second side wall (2W)
third side wall (3W)
fourth side wall (4W)
top (5W)
floor (1FL)
air input (Q1)
air supply entry conduit (Q2)
air supply (Q3)
inlet distributor (Q4)
air heater (HXA)
heat transfer medium input (Q5)
heat transfer medium output (Q6)
first humidity sensor (Q8)
signal (Q9)
second humidity sensor (Q10)
signal (Q11)
air supply fan (Q12)
air supply fan motor (Q13)
controller (Q14)
signal (Q15)
water (Q16)
water transfer conduit (Q17)
water input valve (Q18)
water flow sensor (Q19)
signal (Q20)
water and gas mixing section (Q21)
air output (Q22)
air discharge exit conduit (Q23)
air filter (Q24)
condensate (Q25)
enclosure condensate input (Q26)
condensate conduit (Q27)
common tank condensate input (Q28)
first undesirable compounds-laden condensate (Q29)
humidity control unit (HCU)
compressor (Q30)
refrigerant (Q31)
condenser (Q32)
metering device (Q33)
evaporator (Q34)
fan (Q35)
motor (Q36)
controller (Q37)
signal (Q38)
condensate (Q39)
second undesirable compounds-laden condensate (Q40)
enclosure temperature sensor (QT0)
signal (QXT0)
enclosure humidity sensor (QH0)
signal (QXH0)
heat exchanger inlet gas temperature sensor (QT1)
signal (QXT1)
heat exchanger outlet gas temperature sensor (QT2)
signal (QXT2)
heat exchanger heat transfer medium inlet temperature (QT3)
signal (QXT3)
heat exchanger heat transfer medium outlet temperature (QT4)
signal (QXT4)

computer (COMP)
memory (MEM)
code (CODE)
I/O (input output interface)
processor (PROC)
width (104W)
length (104L)
supports (104A)
multi-point temperature sensor (MPT100)
first signal (XMPT1)
second signal (XMPT2)
third signal (XMPT3)
fourth signal (XMPT4)
fifth signal (XMPT5)
sixth signal (XMPT6)
seventh signal (XMPT7)
eighth signal (XMPT8)
base width (104W0)
first distance (104W1)
second distance (104W2)
third distance (104W)
fourth distance (104W4)
fifth distance (104W5)
sixth distance (104W6)
seventh distance (104W7)
eighth distance (104W8)
analyzer (AZ0
analyzer signal (XAZ)
growing medium (GM1, GM2)
cannabis cloning assembly (CA)
containers (TY1, TY2, TY3, TY$^N$, TY$^{N+1}$)
cloning enclosure (CHD)
interior (CHD-1)
cutting tool (CT1)
rooting solution (RS)
growing medium (GM)
severed plants (107X, 207X)
heater (HTR1)
heated cannabis (HT1)
conveyor (CVR1)
heater temperature sensor (HTR1T)
signal (HTR1X)
carbon dioxide depleted cannabis (CO2-1)
decarboxylated cannabis (DCX)
carbon dioxide (CO2R)
vacuum (VAC)
motor (MT1)
blade (CT2)

What is claimed is:

1. A method to produce concentrated volatiles from cannabis, the method includes:
    (a) providing a source of cannabis, the cannabis includes volatiles, the volatiles include terpenes, wax, and oil;
    (b) after step (a), extracting the volatiles from the cannabis with $CO_2$ to form a $CO_2$ and volatiles mixture according to a method including:
        (b1) separating the terpenes from the cannabis at a first temperature and a first pressure; and
        (b2) after step (b1), separating the oil and the wax from the cannabis at a second temperature and a second pressure, the second temperature is greater than the first temperature, the second pressure is greater than the first pressure, the $CO_2$ and volatiles mixture includes $CO_2$, oil, and wax;
    (c) after step (b), removing the $CO_2$ from the $CO_2$ and volatiles mixture to produce extracted volatiles, the extracted volatiles includes oil and wax;
    (d) after step (c), mixing the extracted volatiles with ethanol to produce an ethanol and volatiles mixture;
    (e) after step (d), cooling the ethanol and volatiles mixture to form a cooled ethanol and volatiles mixture;
    (f) after step (e), filtering the cooled ethanol and volatiles mixture to form a filtered ethanol and volatiles mixture;
    (g) after step (f), evaporating the ethanol from the filtered ethanol and volatiles mixture under vacuum conditions to produce concentrated volatiles and vaporized ethanol;
    (h) after step (g), condensing the vaporized ethanol to produce liquid ethanol and non-condensable gas, the non-condensable gas has a reduced amount of ethanol vapor relative to the vaporized ethanol; and
    (i) after step (h), introducing the non-condensable gas to a vacuum system.

2. The method according to claim 1, comprising:
in step (g), evaporating the ethanol with a wiped-film evaporator.

3. The method according to claim 1, comprising:
in step (g), evaporating the ethanol with a falling film tubular evaporator.

4. The method according to claim 1, comprising:
in step (g), evaporating the ethanol with a rising film tubular evaporator.

5. The method according to claim 1, comprising:
in step (g), evaporating the ethanol with a forced circulation evaporator.

6. The method according to claim 1, comprising:
in step (g), evaporating the ethanol with a thermal vapor recompression evaporator.

7. The method according to claim 1, comprising:
in step (g), evaporating the ethanol with a mechanical vapor recompression evaporator.

8. The method according to claim 1, comprising:
in step (g), evaporating the ethanol with a distillation column.

9. The method according to claim 1, comprising:
in step (g), evaporating the ethanol from the filtered ethanol and volatiles mixture with an electrically-heated evaporator.

10. The method according to claim 1, comprising:
in step (g), evaporating the ethanol from the filtered ethanol and volatiles mixture with an electrically-heated evaporator; wherein the evaporator includes a falling film tubular evaporator and/or a rising film tubular evaporator.

11. The method according to claim 1, wherein:
the concentrated volatiles are essentially free from tetrahydrocannabinolic acid and include active tetrahydrocannabinol.

12. The method according to claim 1, wherein:
the concentrated volatiles include two or more selected from the group consisting of hexane, pentane, acetone, and isopropanol.

13. The method according to claim 1, wherein:
in step (a), the cannabis includes bacteria and fungi.

14. The method according to claim 1, wherein:
in step (a), the cannabis includes ground cannabis, the ground cannabis includes bacteria and fungi.

15. The method according to claim 14, wherein:
the ground cannabis includes vitamin E.

16. The method according to claim 1, wherein:
in step (a), the source of cannabis includes ground hybrid asexually cloned cannabis comprising a hybrid between *Cannabis sativa* L. ssp. *sativa* and *Cannabis*

*sativa* L. ssp. *indica* (Lam.); the ground hybrid asexually cloned cannabis includes the terpenes; and the terpenes include three or more terpenes selected from the group consisting of limonene, humulene, pinene, linalool, caryophyllene, eucalyptol, nerolidol, and phytol.

17. The method according to claim 16, wherein:
the ground hybrid asexually cloned cannabis includes bacteria and fungi.

18. The method according to claim 1, wherein:
in step (a), the source of cannabis includes ground hybrid asexually cloned cannabis comprising a hybrid between *Cannabis sativa* L. ssp. *sativa* and *Cannabis sativa* L. ssp. *indica* (Lam.).

19. The method according to claim 1, wherein:
in step (a), the source of cannabis includes asexually cloned cannabis.

20. The method according to claim 1, wherein:
in step (a), the source of cannabis includes ground cannabis.

21. The method according to claim 20, wherein:
in step (a), the source of ground cannabis is derived from cannabis plants grown indoors.

22. The method according to claim 20, wherein:
in step (a), the source of ground cannabis is derived from cannabis plants grown outdoors.

23. The method according to claim 20, wherein:
in step (a), the source of ground cannabis includes ground cannabis flowers.

24. The method according to claim 20, wherein:
in step (a), the source of ground cannabis includes ground cannabis leaves; wherein:
the ground cannabis leaves are derived from cannabis leaves comprising palmately compound leaves with 5 to 11 serrated leaflets per leaf.

25. The method according to claim 1, wherein:
in step (b), the $CO_2$ includes liquid $CO_2$.

26. The method according to claim 1, wherein:
in step (b), the $CO_2$ includes supercritical $CO_2$ and/or subcritical $CO_2$.

27. The method according to claim 1, wherein:
in step (h), the non-condensable gas includes nitrogen.

28. The method according to claim 1, wherein:
in step (h), the non-condensable gas includes air.

29. The method according to claim 1, wherein:
in step (i), the vacuum system includes a liquid-ring vacuum pump.

30. The method according to claim 1, wherein:
the concentrated volatiles include cannabidiol.

31. The method according to claim 1, wherein:
the concentrated volatiles include tetrahydrocannabinolic acid.

32. The method according to claim 1, wherein:
the concentrated volatiles include active tetrahydrocannabinol.

* * * * *